(12) United States Patent
Tada et al.

(10) Patent No.: US 9,120,825 B2
(45) Date of Patent: Sep. 1, 2015

(54) HYDROSILANE DERIVATIVE, METHOD FOR PRODUCING SAME, AND METHOD FOR PRODUCING SILICON-CONTAINING THIN FILM

(75) Inventors: Ken-ichi Tada, Kanagawa (JP); Kohei Iwanaga, Kanagawa (JP); Toshiki Yamamoto, Kanagawa (JP); Atsushi Maniwa, Kanagawa (JP)

(73) Assignees: TOSOH CORPORATION, Yamaguchi (JP); SAGAMI CHEMICAL RESEARCH INSTITUTE, Kanagawa (JP)

( * ) Notice: Subject to any disclaimer, the term of this patent is extended or adjusted under 35 U.S.C. 154(b) by 233 days.

(21) Appl. No.: 13/702,723

(22) PCT Filed: May 30, 2011

(86) PCT No.: PCT/JP2011/062320
§ 371 (c)(1),
(2), (4) Date: Jan. 23, 2013

(87) PCT Pub. No.: WO2011/155353
PCT Pub. Date: Dec. 15, 2011

(65) Prior Publication Data
US 2013/0123528 A1   May 16, 2013

(30) Foreign Application Priority Data

Jun. 10, 2010 (JP) .................................. 2010-132539
Sep. 8, 2010 (JP) .................................. 2010-200542
Nov. 22, 2010 (JP) .................................. 2010-259888

(51) Int. Cl.
| C07F 7/00 | (2006.01) |
| C07F 7/02 | (2006.01) |
| C23C 16/34 | (2006.01) |
| C23C 16/40 | (2006.01) |
| H01L 21/02 | (2006.01) |

(52) U.S. Cl.
CPC .............. *C07F 7/025* (2013.01); *C23C 16/345* (2013.01); *C23C 16/401* (2013.01); *H01L 21/0217* (2013.01); *H01L 21/02164* (2013.01); *H01L 21/02271* (2013.01)

(58) Field of Classification Search
CPC ........................................................ C07F 7/025
USPC ........................................................ 556/407
See application file for complete search history.

(56) References Cited

U.S. PATENT DOCUMENTS

| 5,866,471 A | 2/1999 | Beppu et al. |
| 2007/0299274 A1 | 12/2007 | Meiere |
| 2008/0081106 A1 | 4/2008 | Wang et al. |
| 2010/0112211 A1 | 5/2010 | Xu et al. |
| 2013/0047890 A1 | 2/2013 | Meiere |
| 2013/0052349 A1 | 2/2013 | Meiere |

FOREIGN PATENT DOCUMENTS

| CN | 101472931 | 7/2009 |
| JP | 2007-294818 | 11/2007 |
| JP | 2008-7471 | 1/2008 |
| JP | 2008-135633 | 6/2008 |
| JP | 2010-504958 | 2/2010 |
| WO | 2009/045964 | 4/2009 |

OTHER PUBLICATIONS

Walker et al., Organometallics (2009), 28(9), 2744-2755.*
Randon H. Walker et al., "Silylene and Germylene-Medicated C—H Activation: Reaction with Alkanes, Ethers, and Amines", Ogranometallics, vol. 28, 2009, pp. 2744-2755.
Search report from International Application No. PCT/JP2011/062320, mail date is Aug. 9, 2011.
International Preliminary Report on Patentability PCT/JP2011/062320, mail date is Aug. 9, 2011.
E.P.O. Office Action in EP 11792310.2, mail date is Feb. 5, 2014.
China Office action in corresponding Chinese Office Action, dated Aug. 27, 2014 along with an English translation thereof.
N. Sievert et al., "2,2-Difluor-1,3-diaza-2-sila-cyclopentene—Synthesis and Reactions", Z. Anorg. Allg. Chem., vol. 663, Feb. 28, 2007, pp. 1223-1232.
Taiwanese Office Action issued with respect to application No. 100119594, mail date is Jan. 7, 2015.

\* cited by examiner

*Primary Examiner* — Porfirio Nazario Gonzalez
*Assistant Examiner* — Kofi Adzamli
(74) *Attorney, Agent, or Firm* — Greenblum & Bernstein, P.L.C.

(57) ABSTRACT

This invention aims at providing a material from which a silicon-containing thin film can be efficiently produced at a low temperature of 500° C. or less without using plasma or the like. The invention relates to produce a hydrosilane derivative represented by the general formula (1') by reacting a chlorosilane derivative (3) with a compound $M^2Z$ (4) and produce the silicon-containing thin film by using the hydrosilane derivative as the material.

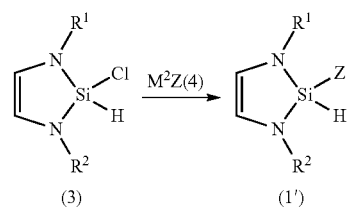

In the formulae, $R^1$, $R^2$ are defined in the specification.

11 Claims, 32 Drawing Sheets

HYDROSILANE DERIVATIVE, METHOD FOR PRODUCING SAME, AND METHOD FOR PRODUCING SILICON-CONTAINING THIN FILM

CROSS REFERENCE TO RELATED APPLICATIONS

The present application is a National Stage §371 entry of PCT/JP2011/062320 filed May 30, 2011, which claims priority to: JP 2010-259888 filed on Nov. 22, 2010, JP 2010-200542 filed on Sep. 8, 2010, and JP 2010-132539 filed Jun. 10, 2010, the contents of each being incorporated herein in their entirety.

TECHNICAL FIELD

The present invention relates to a hydrosilane derivative useful, for example, as the material for the production of a semiconductor device, a method for producing the same, and a method for producing a silicon-containing thin film.

BACKGROUND ART

A silicon simple substance and a silicon-containing compound is used as a thin film in many parts constituting a semiconductor device, because electrical properties such as electrical resistivity and relative permittivity can be adjusted by changing the type and/or proportion of the constituent element, and their application in industry is expected to more expand in the future. The silicon-containing compound used in applications to a semiconductor device includes various substances such as silicon dioxide, silicon oxynitride, silicon nitride and metal silicate. Furthermore, in proceeding with high integration of a semiconductor device, it is very important to establish a three-dimensional formation of the device structure, that is, a technique for producing a thin film on a three-dimensionally shaped substrate surface. From this viewpoint, a chemical vapor deposition method (CVD method) and an atomic layer deposition method (ALD method) are particularly attracting attention as a thin-film production process suitable for the process of producing a semiconductor device of future generations. As the material for producing a silicon-containing thin film by using a CVD method or an ALD method, studies are being made on use of various silicon compounds. However, a silane gas explosively reacts with an oxygen gas, which limits its use, and tetraethoxysilane (TEOS) is limited in its use, because a high temperature or a plasma is indispensable for the production of a thin film. Tris(dimethylamino)silane (TDMAS) is also being studied as the material for producing a silicon-containing thin film by the CVD method or ALD method. For example, Patent Document 1 describes a method for producing a silicon dioxide thin film by a plasma-enhanced chemical vapor deposition method (PECVD method) using TDMAS as the material. Also, Patent Document 2 describes a method for producing a silicon dioxide thin film by the ALD method using TDMAS and ozone or an oxygen gas.

With respect to the substance analogous to the hydrosilane derivative (1) of the present invention, Non-Patent Document 1 describes, as Compounds 8 and 10, 1,3-di-tert-butyl-2-diethylamino-1,3-diaza-2-silacyclopent-4-ene (Si($^t$BuNCHCHN$^t$Bu)(H)NEt$_2$) and 1,3-di-tert-butyl-2-dipropylamino-1,3-diaza-2-silacyclopent-4-ene (Si($^t$BuNCHCHN$^t$Bu)(H)NPr$_2$), respectively, but is absolutely silent on using such a compound as the material for producing a silicon-containing thin film. Also, there are not found at all description about a derivative having a dialkylamino group except for diethylamino group and dipropylamino group, or a derivative having an amino group, a monoalkylamino group, an isocyanato group, a thioisocyanato group or an alkenyl group.

RELATED ART

Patent Document

Patent Document 1: International Publication No. 2009-045964, pamphlet
Patent Document 2: JP-A-2008-135633

Non-Patent Document

Non-Patent Document 1: *Organometallics*, Vol. 28, page 2744 (2009)

SUMMARY OF THE INVENTION

Problems that the Invention is to Solve

In the case of producing a semiconductor device, thin films formed of a plurality of different compounds must be stacked. However, there is a problem in using existing silicon compounds as the practical material for producing a silicon-containing thin film. For example, in producing a silicon dioxide thin film by using only TDMAS and an oxygen gas, a high substrate temperature is indispensable for accelerating the reaction of TDMAS with oxygen. Also, in Patent Document 2, it is stated that in the case of producing a silicon dioxide thin film by the ALD method using only TDMAS and an oxygen gas, a thin film can be produced at 550° C. but if the substrate temperature is low, a film is not deposited. Furthermore, the present inventors have tried to produce a silicon dioxide thin film by the CVD method using TDMAS and an oxygen gas and confirmed that deposition of a film scarcely proceeds at a substrate temperature of 500° C. or less (see, Comparative Example-1, Comparative Example-2 and Comparative Example-3). When the substrate temperature at the production of a thin film is high, there may arise a trouble such as interdiffusion or delamination between respective layers, and therefore, it is required to produce a thin film at a temperature as low as possible. In addition, a PECVD method using a plasma and a method using ozone are also studied as the means to accelerate the reaction of TDMAS with oxygen, but both are of narrow application as a practical thin-film production method, because the PECVD method has a problem of damage to the substrate by a plasma and the method using ozone has a problem of oxidation of the substrate by ozone. That is, a silicon compound capable of forming a thin film only by heating without use of an auxiliary agent such as plasma and ozone, at a temperature as low as possible is required, but such a compound has not been found yet. For solving these problems, it is necessary to develop a new silicon material for thin film production, which makes it possible to efficiently produce a silicon-containing thin film such as silicon dioxide or silicon nitride even at a low temperature of 500° C. or less without using a plasma or ozone.

Means for Solving the Problems

As a result of intensive studies to solve the above-described problems, the present inventors have found that a hydrosilane derivative having a cyclic structure represented by formula (1) or (1') is an excellent compound capable of efficiently producing a silicon-containing thin film such as silicon dioxide or silicon nitride even at a low temperature of 500° C. or less without using a plasma or ozone. The present invention has been accomplished based on this finding.

That is, the present invention relates to a hydrosilane derivative represented by formula (1):

[Chem. 1]

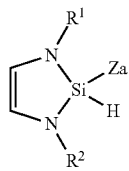
(1)

(wherein each of $R^1$ and $R^2$ independently represents an alkyl group having a carbon number of 3 to 12, Za represents an isocyanato group, an isothiocyanato group, an amino group, a monosubstituted amino group represented by $NHR^3$, an N-methyl-alkylamino group represented by $N(CH_3)R^4$, or an alkenyl group having a carbon number of 2 to 6, $R^3$ represents an alkyl group having a carbon number of 1 to 12, which may be substituted with a fluorine atom, and $R^4$ represents an alkyl group having a carbon number of 1 to 4).

Also, the present invention relates to a method for producing a hydrosilane derivative, comprising reacting a chlorosilane derivative represented by formula (3):

[Chem. 2]

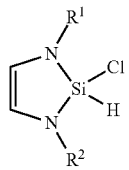
(3)

(wherein each of $R^1$ and $R^2$ independently represents an alkyl group having a carbon number of 3 to 12) with a compound represented by formula (4):

[Chem. 3]

$M^2Z$ (4)

(wherein Z represents an isocyanato group, an isothiocyanato group, an amino group, a monosubstituted amino group represented by $NHR^3$, a disubstituted amino group represented by $NR^4R^5$, or an alkenyl group having a carbon number of 2 to 6, $R^3$ represents an alkyl group having a carbon number of 1 to 12, which may be substituted with a fluorine atom, each of $R^4$ and $R^5$ independently represents an alkyl group having a carbon number of 1 to 4, $M^2$ represents a sodium atom or a potassium atom when Z is an isocyanato group or an isothiocyanato group, $M^2$ represents a hydrogen atom or a lithium atom when Z is an amino group, a monosubstituted amino group represented by $NHR^3$ or a disubstituted amino group represented by $NR^4R^5$, and $M^2$ represents a magnesium halide group when Z is an alkenyl group having a carbon number of 2 to 6) to produce a hydrosilane derivative represented by formula (1'):

[Chem. 4]

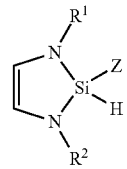
(1')

(wherein each of $R^1$ and $R^2$ independently represents an alkyl group having a carbon number of 3 to 12, Z represents an isocyanato group, an isothiocyanato group, an amino group, a monosubstituted amino group represented by $NHR^3$, a disubstituted amino group represented by $NR^4R^5$, or an alkenyl group having a carbon number of 2 to 6, $R^3$ represents an alkyl group having a carbon number of 1 to 12, which may be substituted with a fluorine atom, and each of $R^4$ and $R^5$ independently represents an alkyl group having a carbon number of 1 to 4).

Furthermore, the present invention relates to a method for producing a hydrosilane derivative, comprising reacting a vinylenediaminide alkali metal salt represented by formula (2):

[Chem.5]

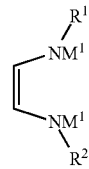
(2)

(wherein each of $R^1$ and $R^2$ independently represents an alkyl group having a carbon number of 3 to 12, and $M^1$ represents a lithium atom or a sodium atom) with trichlorosilane to produce a chlorosilane derivative represented by formula (3):

[Chem. 6]

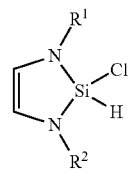
(3)

(wherein each of $R^1$ and $R^2$ independently represents an alkyl group having a carbon number of 3 to 12), and further reacting the chlorosilane derivative (3) with a compound represented by formula (4):

[Chem. 7]

$M^2Z$ (4)

(wherein Z represents an isocyanato group, an isothiocyanato group, an amino group, a monosubstituted amino group represented by $NHR^3$, a disubstituted amino group represented by $NR^4R^5$, or an alkenyl group having a carbon number of 2 to 6, $R^3$ represents an alkyl group having a carbon number of 1 to 12, which may be substituted with a fluorine atom, each of $R^4$ and $R^5$ independently represents an alkyl group having a carbon number of 1 to 4, $M^2$ represents a sodium atom or a potassium atom when Z is an isocyanato group or an isothiocyanato group, $M^2$ represents a hydrogen atom or a lithium atom when Z is an amino group, a monosubstituted amino group represented by $NHR^3$ or a disubstituted amino group represented by $NR^4R^5$, and $M^2$ represents a magnesium halide group when Z is an alkenyl group having a carbon number of 2 to 6) to produce a hydrosilane derivative represented by formula (1'):

[Chem. 8]

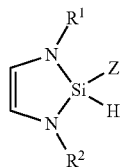

(1')

(wherein each of $R^1$ and $R^2$ independently represents an alkyl group having a carbon number of 3 to 12, Z represents an isocyanato group, an isothiocyanato group, an amino group, a monosubstituted amino group represented by $NHR^3$, a disubstituted amino group represented by $NR^4R^5$, or an alkenyl group having a carbon number of 2 to 6, $R^3$ represents an alkyl group having a carbon number of 1 to 12, which may be substituted with a fluorine atom, and each of $R^4$ and $R^5$ independently represents an alkyl group having a carbon number of 1 to 4).

Furthermore, the present invention relates to a method for producing a silicon-containing thin film, comprising using, as the material, a hydrosilane derivative represented by formula (1'):

[Chem. 9]

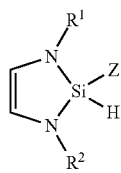

(1')

(wherein each of $R^1$ and $R^2$ independently represents an alkyl group having a carbon number of 3 to 12, Z represents an isocyanato group, an isothiocyanato group, an amino group, a monosubstituted amino group represented by $NHR^3$, a disubstituted amino group represented by $NR^4R^5$, or an alkenyl group having a carbon number of 2 to 6, $R^3$ represents an alkyl group having a carbon number of 1 to 12, which may be substituted with a fluorine atom, and each of $R^4$ and $R^5$ independently represents an alkyl group having a carbon number of 1 to 4).

That is, the gist of the present invention resides in the following (1) to (9).

(1) A hydrosilane derivative represented by formula (1):

[Chem. 10]

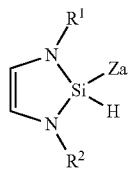

(1)

(wherein each of $R^1$ and $R^2$ independently represents an alkyl group having a carbon number of 3 to 12, Za represents an isocyanato group, an isothiocyanato group, an amino group, a monosubstituted amino group represented by $NHR^3$, an N-methyl-alkylamino group represented by $N(CH_3)R^4$, or an alkenyl group having a carbon number of 2 to 6, $R^3$ represents an alkyl group having a carbon number of 1 to 12, which may be substituted with a fluorine atom, and $R^4$ represents an alkyl group having a carbon number of 1 to 4).

(2) The hydrosilane derivative as described in (1), wherein, preferably, each of $R^1$ and $R^2$ is independently an alkyl group having a carbon number of 3 to 8, Za is an isocyanato group, an amino group, a monosubstituted amino group represented by $NHR^3$, or an alkenyl group having a carbon number of 2 to 4, and $R^3$ is an alkyl group having a carbon number of 1 to 8, which may be substituted with a fluorine atom.

(3) The hydrosilane derivative as described in (1) or (2), wherein, preferably, each of $R^1$ and $R^2$ is independently a tert-butyl group or a tert-pentyl group, Za is an amino group or a monosubstituted amino group represented by $NHR^3$, and $R^3$ is an alkyl group having a carbon number of 1 to 4.

(4) A method for producing a hydrosilane derivative, comprising reacting a chlorosilane derivative represented by formula (3):

[Chem. 11]

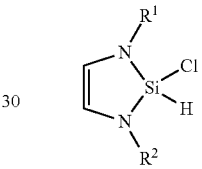

(3)

(wherein each of $R^1$ and $R^2$ independently represents an alkyl group having a carbon number of 3 to 12) with a compound represented by formula (4):

[Chem. 12]

$M^2Z$ (4)

(wherein Z represents an isocyanato group, an isothiocyanato group, an amino group, a monosubstituted amino group represented by $NHR^3$, a disubstituted amino group represented by $NR^4R^5$, or an alkenyl group having a carbon number of 2 to 6, $R^3$ represents an alkyl group having a carbon number of 1 to 12, which may be substituted with a fluorine atom, each of $R^4$ and $R^5$ independently represents an alkyl group having a carbon number of 1 to 4, $M^2$ represents a sodium atom or a potassium atom when Z is an isocyanato group or an isothiocyanato group, $M^2$ represents a hydrogen atom or a lithium atom when Z is an amino group, a monosubstituted amino group represented by $NHR^3$ or a disubstituted amino group represented by $NR^4R^5$, and $M^2$ represents a magnesium halide group when Z is an alkenyl group having a carbon number of 2 to 6) to produce a hydrosilane derivative represented by formula (1'):

[Chem. 13]

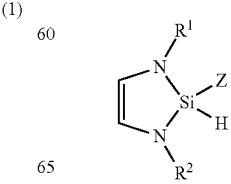

(1')

(wherein each of $R^1$ and $R^2$ independently represents an alkyl group having a carbon number of 3 to 12, Z represents an isocyanato group, an isothiocyanato group, an amino group, a monosubstituted amino group represented by $NHR^3$, a disubstituted amino group represented by $NR^4R^5$, or an alkenyl group having a carbon number of 2 to 6, $R^3$ represents an alkyl group having a carbon number of 1 to 12, which may be substituted with a fluorine atom, and each of $R^4$ and $R^5$ independently represents an alkyl group having a carbon number of 1 to 4).

(5) The production method as described in (4), wherein, preferably, Z is an isocyanato group, an amino group, a monosubstituted amino group represented by $NHR^3$, or an alkenyl group having a carbon number of 2 to 4, each of $R^1$ and $R^2$ is independently an alkyl group having a carbon number of 3 to 8, and $R^3$ is an alkyl group having a carbon number of 1 to 8, which may be substituted with a fluorine atom.

(6) The production method as described in (4) or (5), wherein, preferably, Z is an amino group or a monosubstituted amino group represented by $NHR^3$, $M^2$ is a hydrogen atom, each or $R^1$ and $R^2$ is independently a tert-butyl group or a tert-pentyl group, and $R^3$ is an alkyl group having a carbon number of 1 to 4.

(7) A method for producing a hydrosilane derivative, comprising reacting a vinylenediaminide alkali salt represented by formula (2):

[Chem. 14]

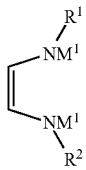

(2)

(wherein each of $R^1$ and $R^2$ independently represents an alkyl group having a carbon number of 3 to 12, and $M^1$ represents a lithium atom or a sodium atom) with trichlorosilane to produce a chlorosilane derivative represented by formula (3):

[Chem. 15]

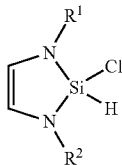

(3)

(wherein each of $R^1$ and $R^2$ independently represents an alkyl group having a carbon number of 3 to 12), and further reacting the chlorosilane derivative (3) with a compound represented by formula (4):

[Chem. 16]

$M^2Z$ (4)

(wherein Z represents an isocyanato group, an isothiocyanato group, an amino group, a monosubstituted amino group represented by $NHR^3$, a disubstituted amino group represented by $NR^4R^5$, or an alkenyl group having a carbon number of 2 to 6, $R^3$ represents an alkyl group having a carbon number of 1 to 12, which may be substituted with a fluorine atom, each of $R^4$ and $R^5$ independently represents an alkyl group having a carbon number of 1 to 4, $M^2$ represents a sodium atom or a potassium atom when Z is an isocyanato group or an isothiocyanato group, $M^2$ represents a hydrogen atom or a lithium atom when Z is an amino group, a monosubstituted amino group represented by $NHR^3$ or a disubstituted amino group represented by $NR^4R^5$, and $M^2$ represents a magnesium halide group when Z is an alkenyl group having a carbon number of 2 to 6) to produce a hydrosilane derivative represented by formula (1'):

[Chem. 17]

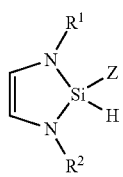

(1')

(wherein each of $R^1$ and $R^2$ independently represents an alkyl group having a carbon number of 3 to 12, Z represents an isocyanato group, an isothiocyanato group, an amino group, a monosubstituted amino group represented by $NHR^3$, a disubstituted amino group represented by $NR^4R^5$, or an alkenyl group having a carbon number of 2 to 6, $R^3$ represents an alkyl group having a carbon number of 1 to 12, which may be substituted with a fluorine atom, and each of $R^4$ and $R^5$ independently represents an alkyl group having a carbon number of 1 to 4).

(8) A method for producing a silicon-containing thin film, comprising using, as the material, a hydrosilane derivative represented by formula (1'):

[Chem. 18]

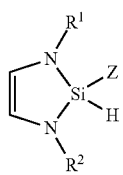

(1')

(wherein each of $R^1$ and $R^2$ independently represents an alkyl group having a carbon number of 3 to 12, Z represents an isocyanato group, an isothiocyanato group, an amino group, a monosubstituted amino group represented by $NHR^3$, a disubstituted amino group represented by $NR^4R^5$, or an alkenyl group having a carbon number of 2 to 6, $R^3$ represents an alkyl group having a carbon number of 1 to 12, which may be substituted with a fluorine atom, and each of $R^4$ and $R^5$ independently represents an alkyl group having a carbon number of 1 to 4).

(9) The production method as described in (8), wherein, preferably, Z is an amino group or a monosubstituted amino group represented by $NHR^3$ and $R^3$ is an alkyl group having a carbon number of 1 to 4.

Advantage of the Invention

By virtue of using the hydrosilane derivative (1') of the present invention as the material, a silicon-containing thin film such as silicon dioxide or silicon nitride can be efficiently produced even at a low temperature of 500° C. or less without using a plasma or ozone.

MODE FOR CARRYING OUT THE INVENTION

Figure 1:
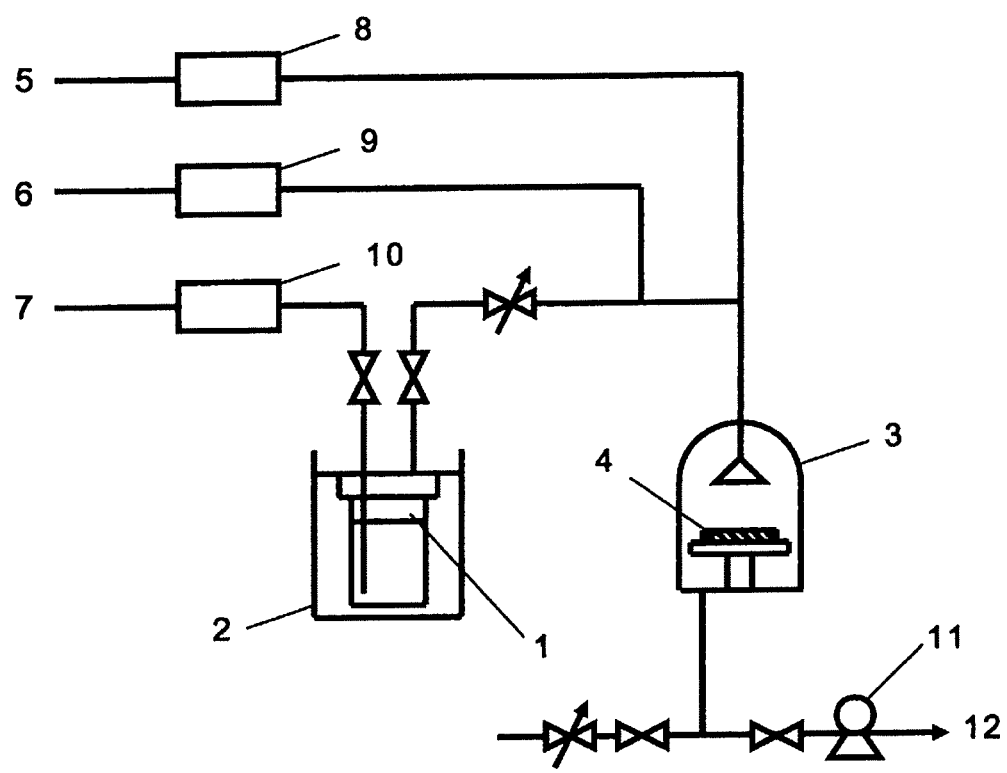
FIG. 1 is a schematic view of the thin-film producing apparatus used in Example-39 to Example-52, Example-57 to Example-65, and Comparative Example-1 to Comparative Example-4.
Figure 2:
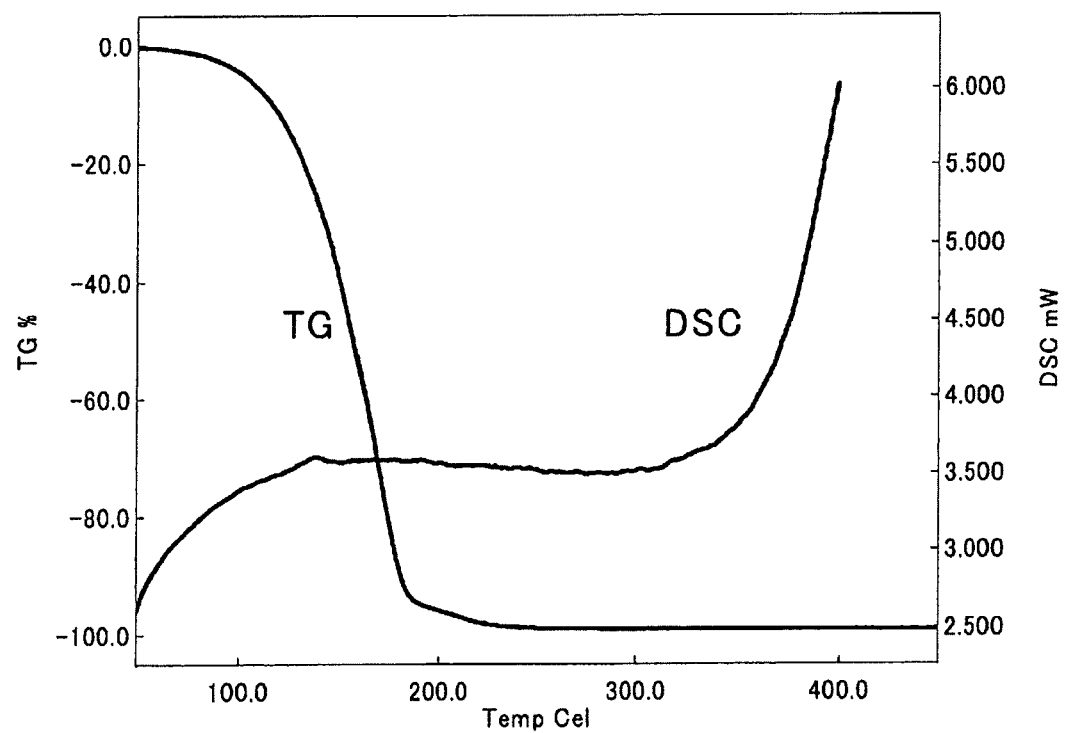
FIG. 2 is TG and DSC charts of Si($^i$PrNCHCHN$^i$Pr)(H)NHEt.
Figure 3:
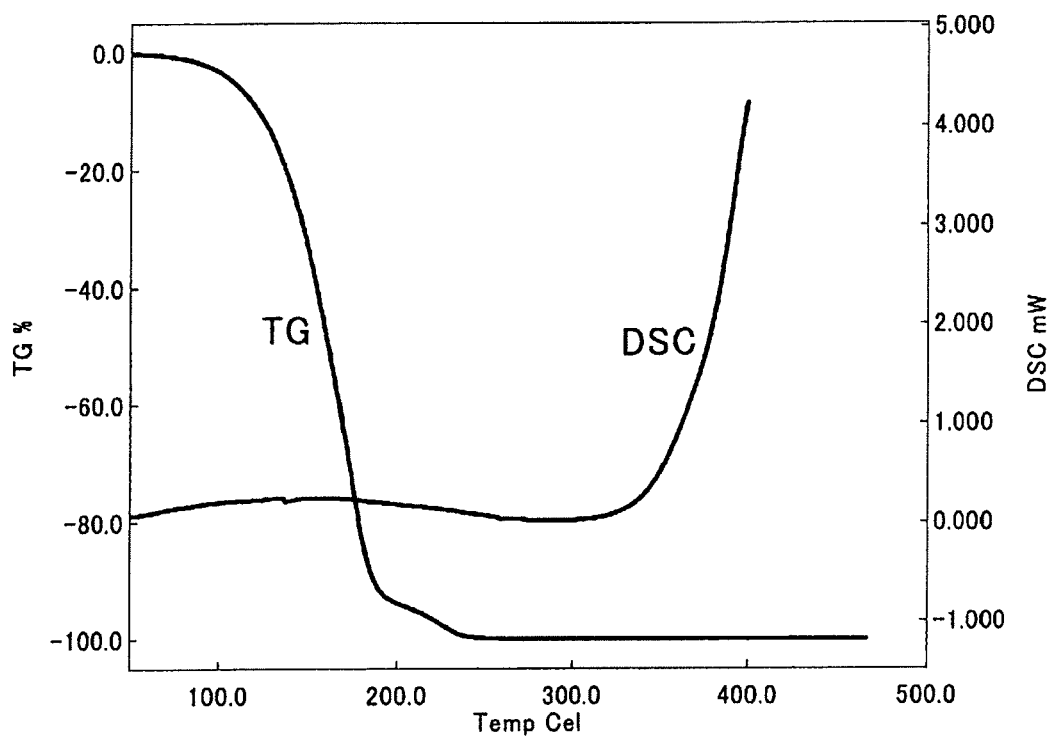
FIG. 3 is TG and DSC charts of Si($^i$PrNCHCHN$^i$Pr)(H)NH$^i$Pr.
Figure 4:
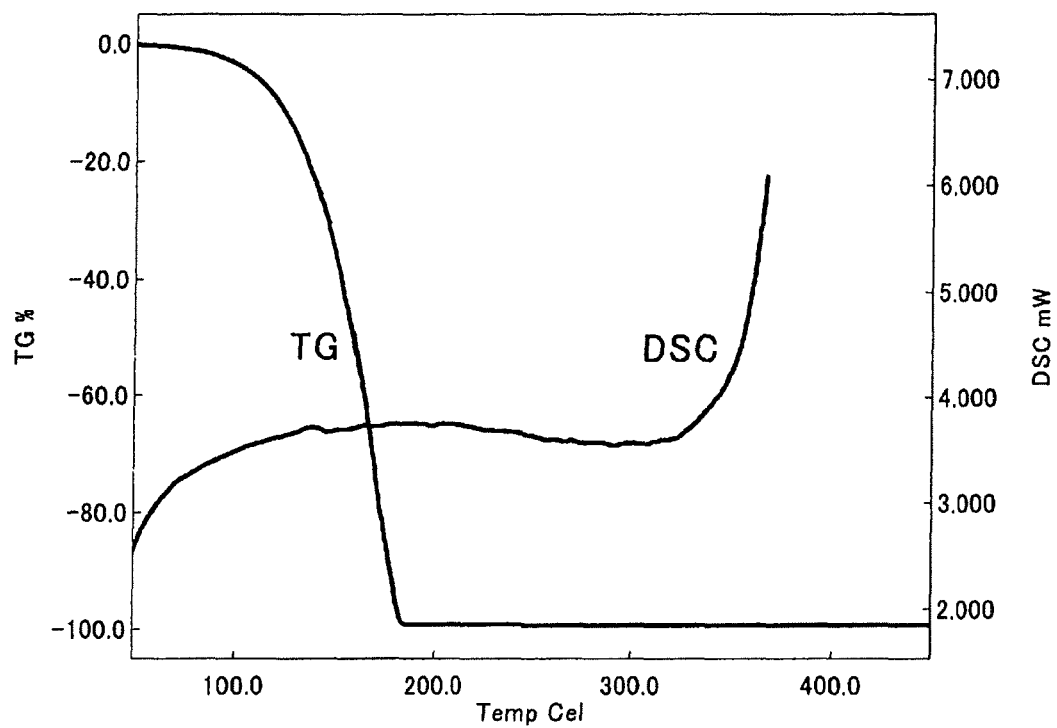
FIG. 4 is TG and DSC charts of Si($^t$BuNCHCHN$^t$Bu)(H)NH$_2$.
Figure 5:
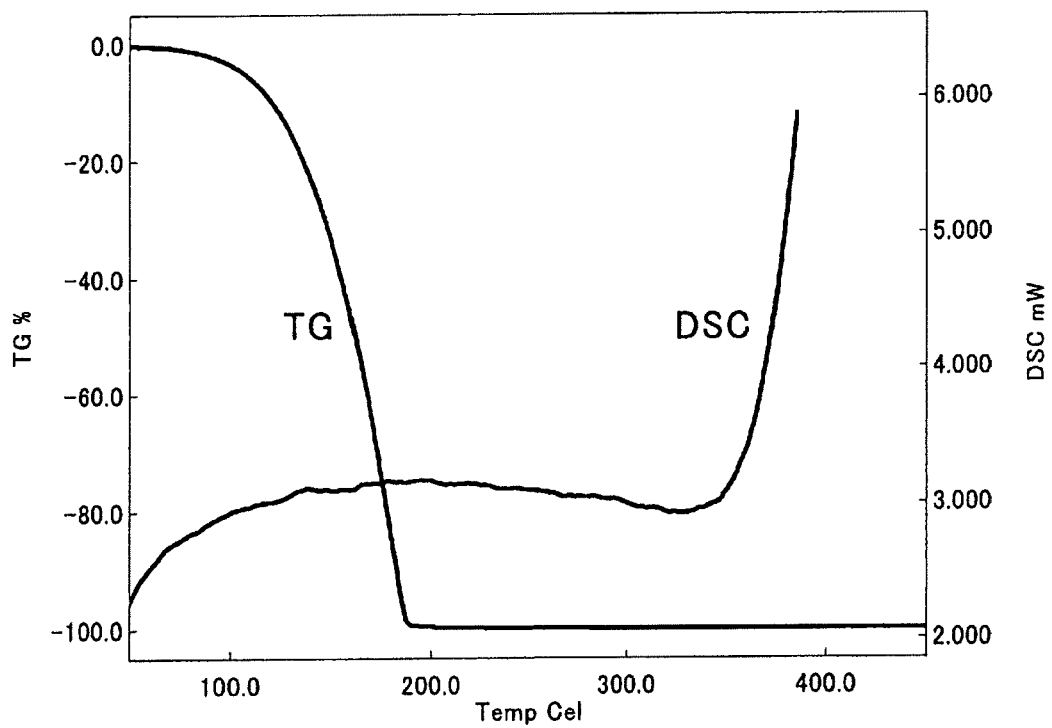
FIG. 5 is TG and DSC charts of Si($^t$BuNCHCHN$^t$Bu)(H)NHMe.
Figure 6:
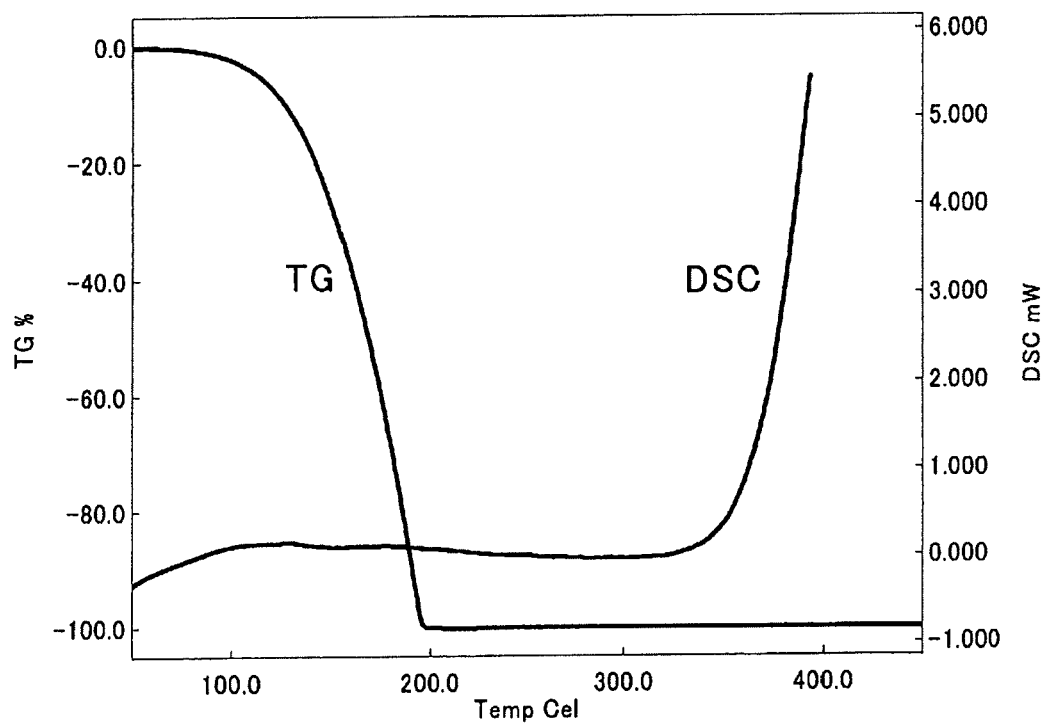
FIG. 6 is TG and DSC charts of Si($^t$BuNCHCHN$^t$Bu)(H)NHEt.
Figure 7:
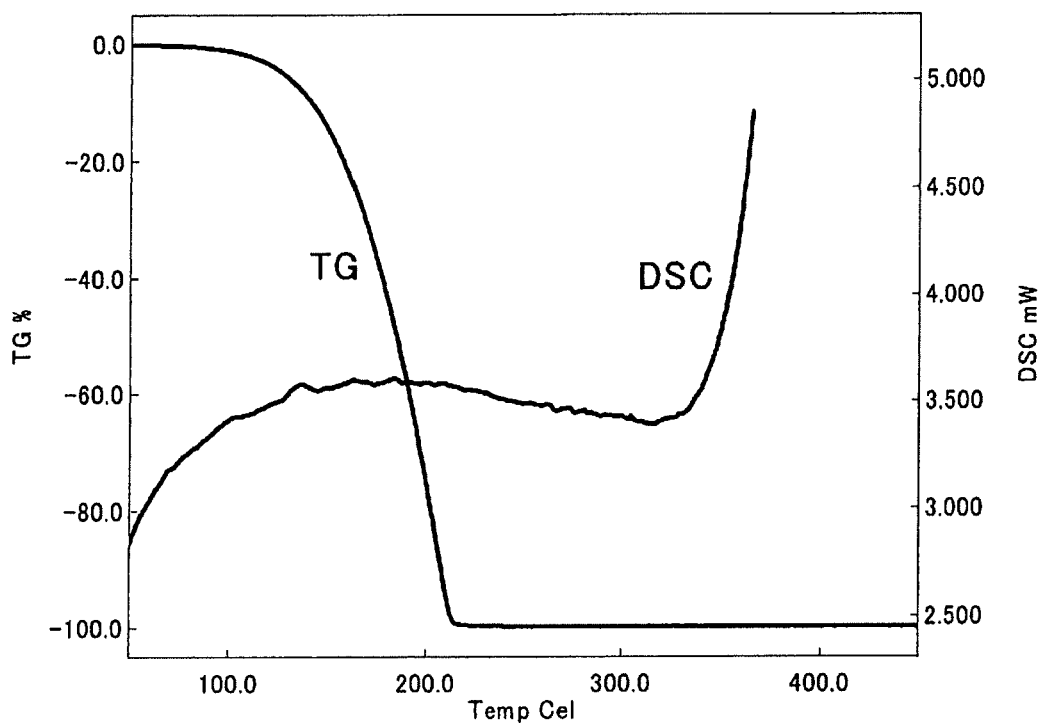
FIG. 7 is TG and DSC charts of Si($^t$BuNCHCHN$^t$Bu)(H)NH$^c$Pr.
Figure 8:
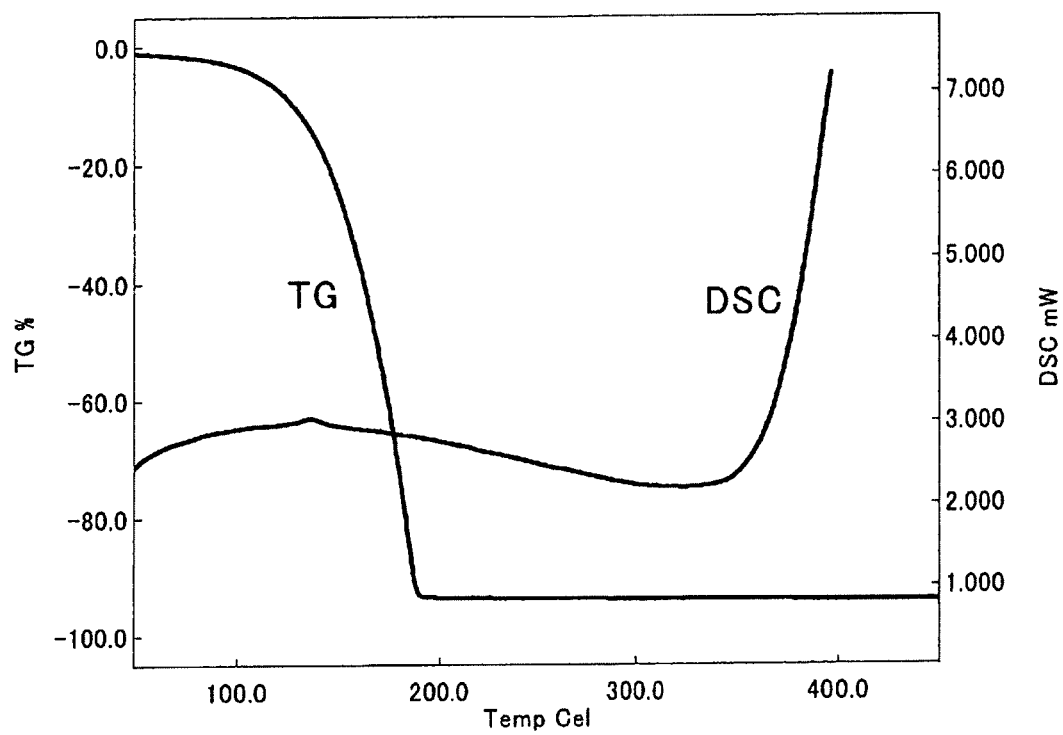
FIG. 8 is TG and DSC charts of Si($^t$BuNCHCHN$^t$Bu)(H)NH$^i$Pr.
Figure 9:
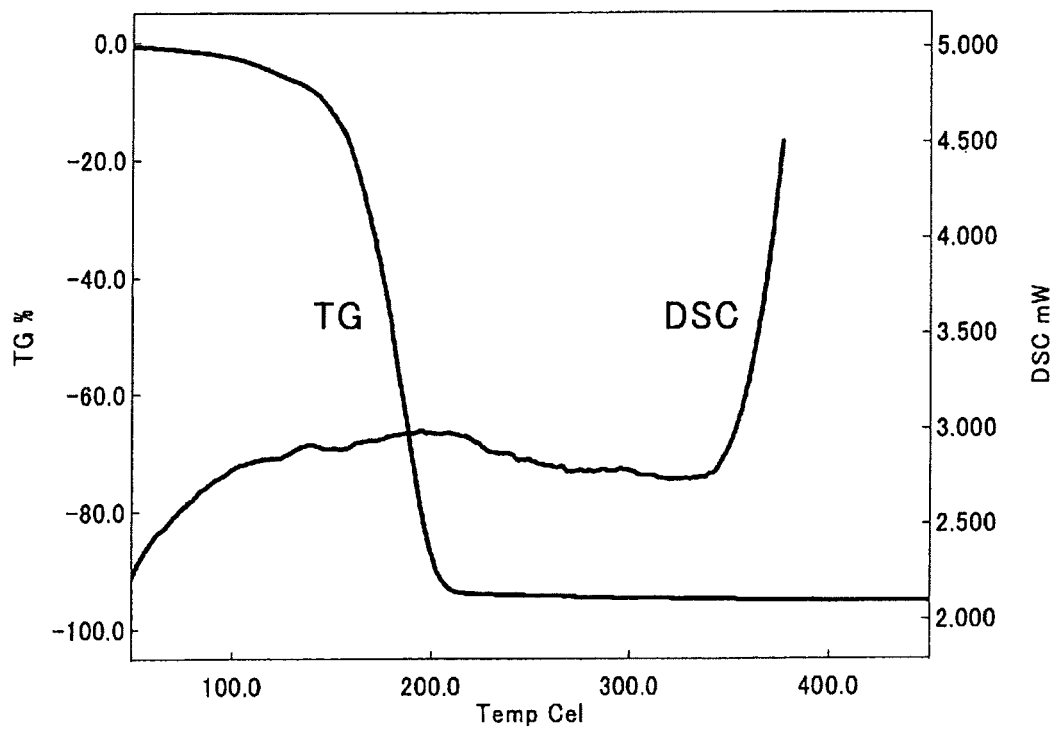
FIG. 9 is TG and DSC charts of Si($^t$BuNCHCHN$^t$Bu)(H)NHPr.
Figure 10:
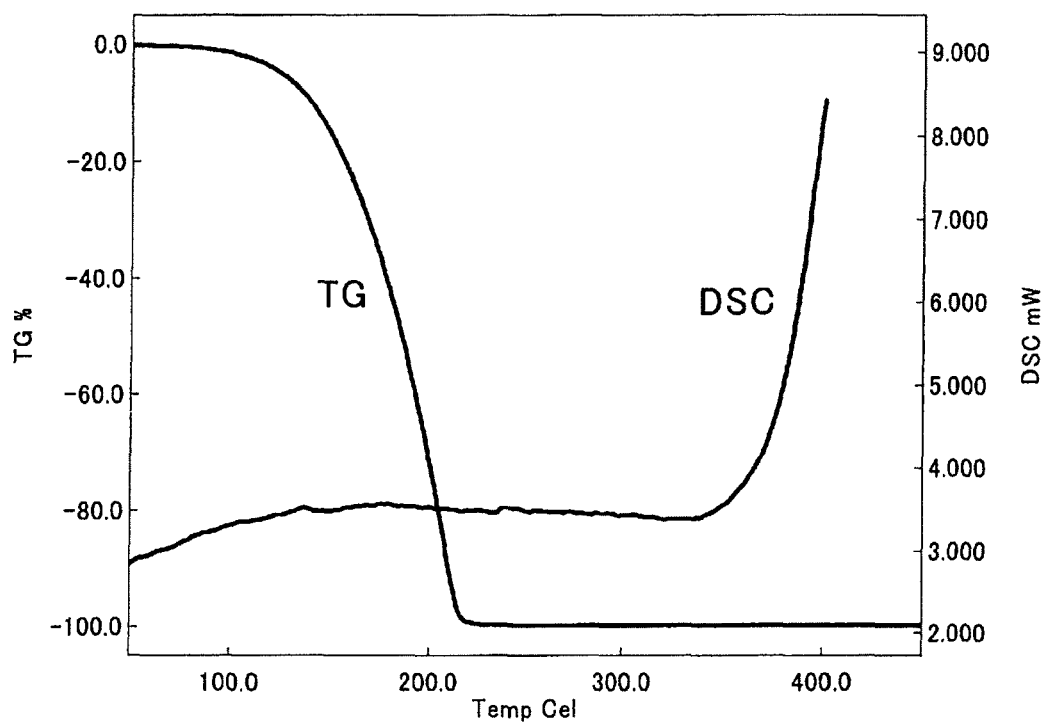
FIG. 10 is TG and DSC charts of Si($^t$BuNCHCHN$^t$Bu)(H)NH$^s$Bu.
Figure 11:
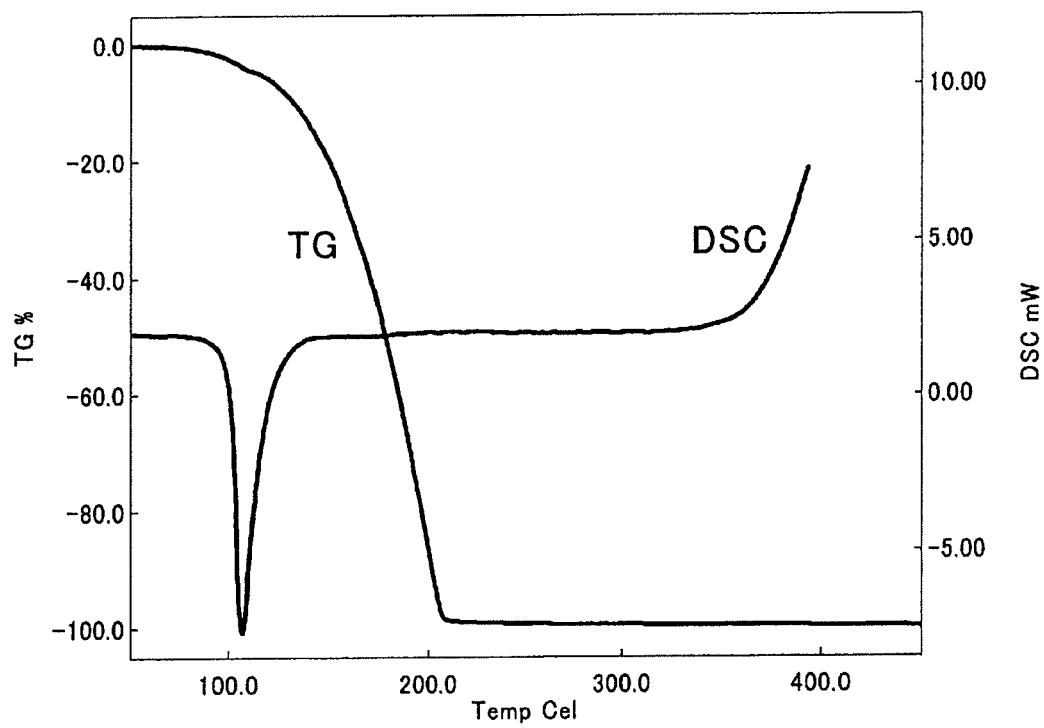
FIG. 11 is TG and DSC charts of Si($^t$BuNCHCHN$^t$Bu)(H)NH$^t$Bu.
Figure 12:
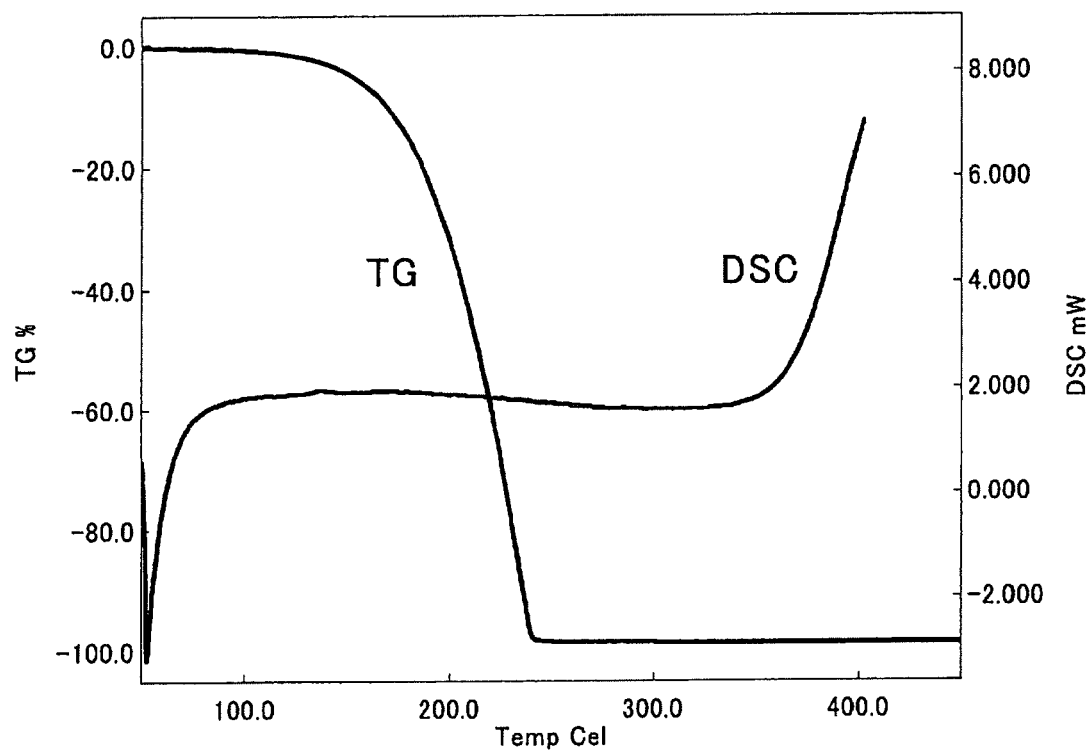
FIG. 12 is TG and DSC charts of Si($^t$BuNCHCHN$^t$Bu)(H)NHCy.
Figure 13:
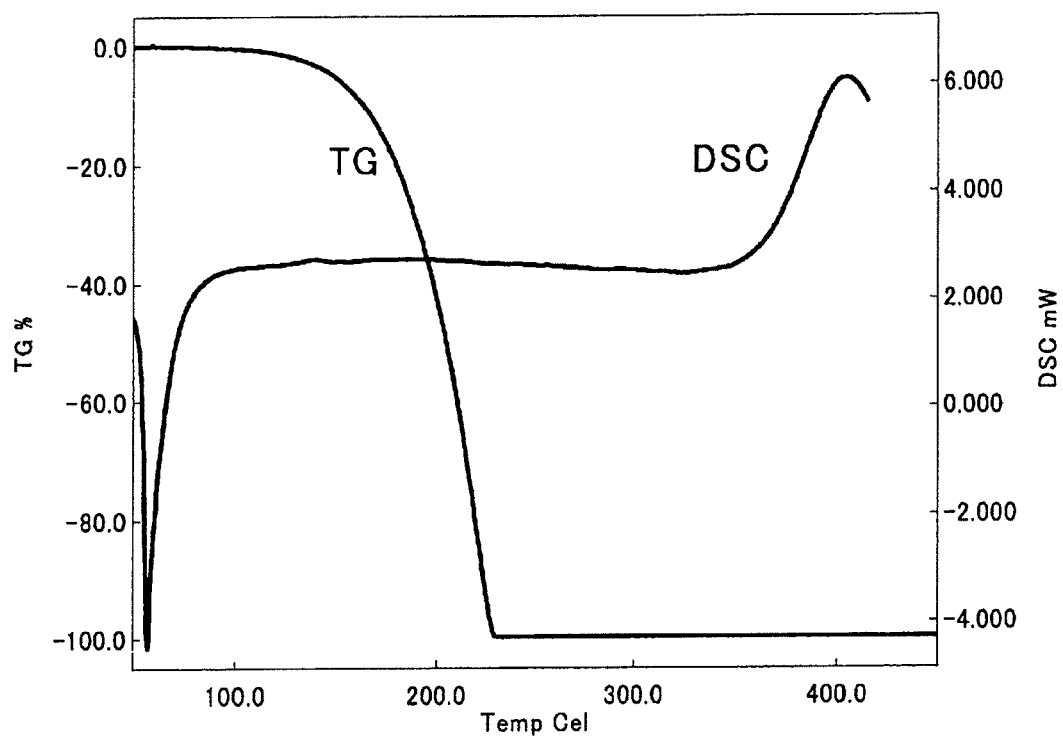
FIG. 13 is TG and DSC charts of Si($^t$BuNCHCHN$^t$Bu)(H)NH$^t$Oct.
Figure 14:
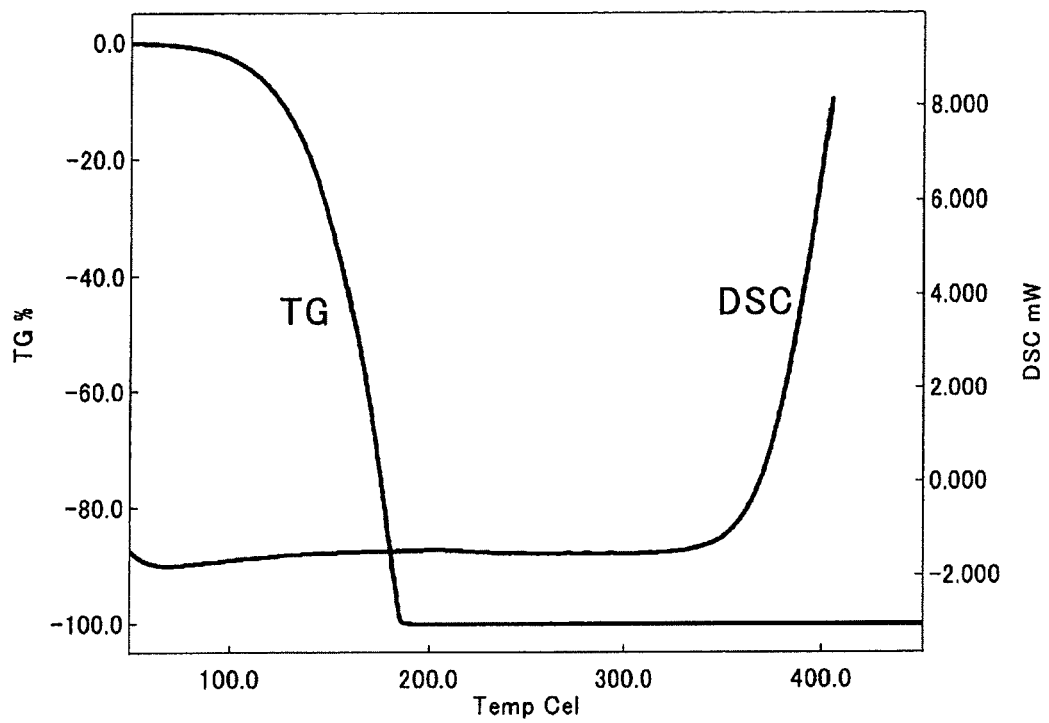
FIG. 14 is TG and DSC charts of Si($^t$BuNCHCHN$^t$Bu)(H)NHCH$_2$CF$_3$.
Figure 15:
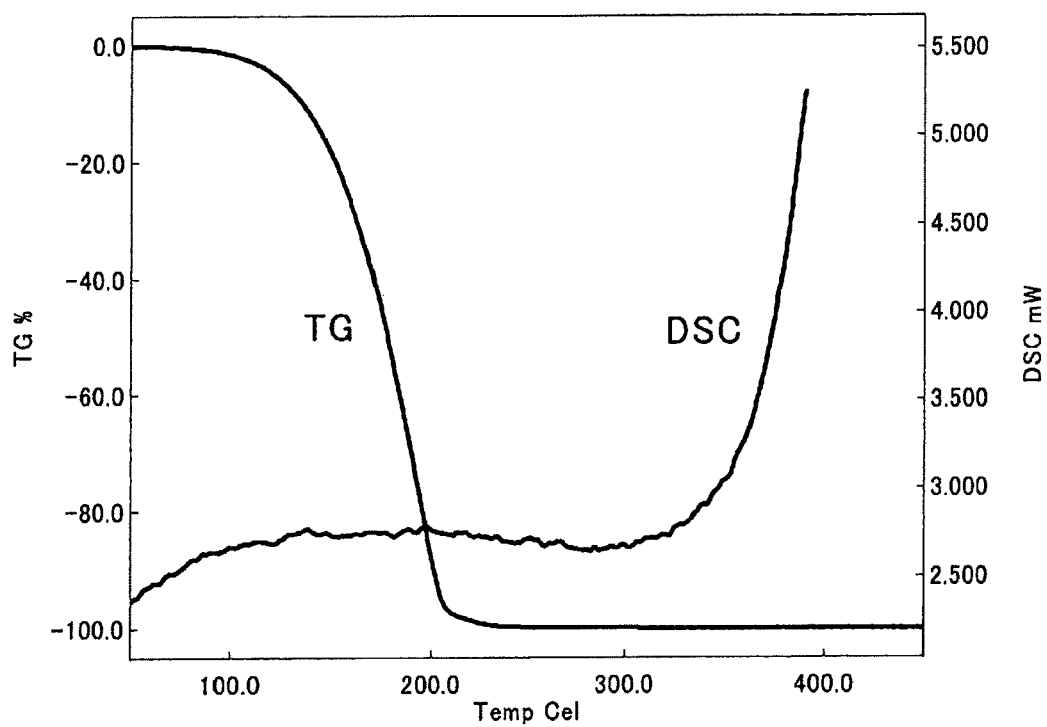
FIG. 15 is TG and DSC charts of Si($^s$BuNCHCHN$^s$Bu)(H)NHEt.
Figure 16:
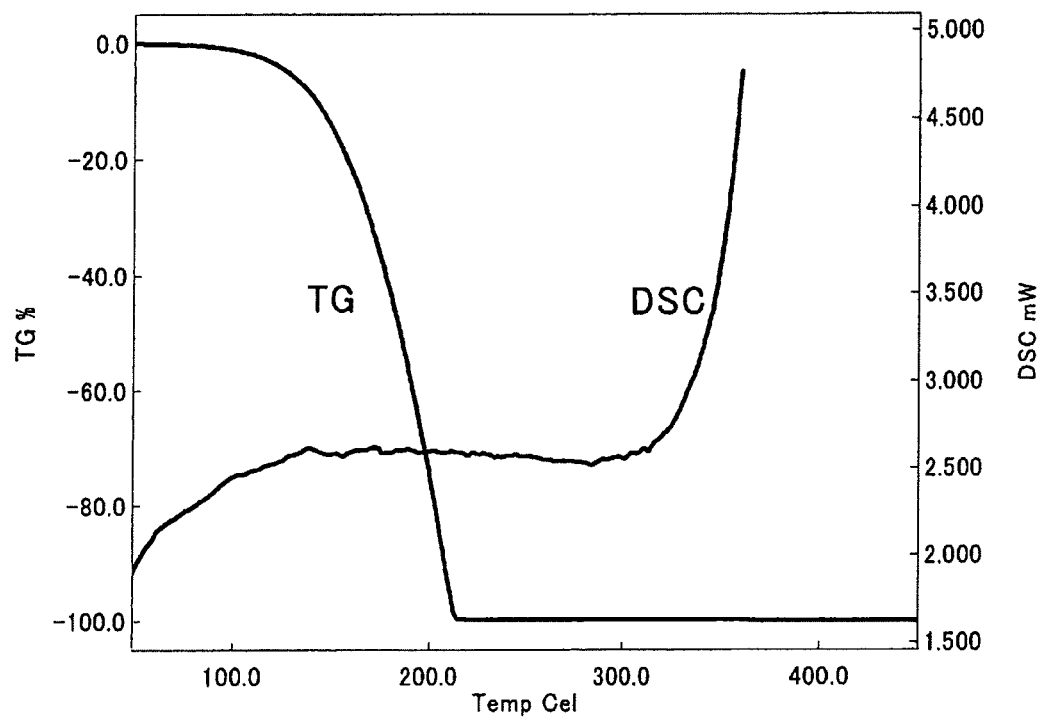
FIG. 16 is TG and DSC charts of Si($^t$PeNCHCHN$^t$Pe)(H)NH$_2$.
Figure 17:
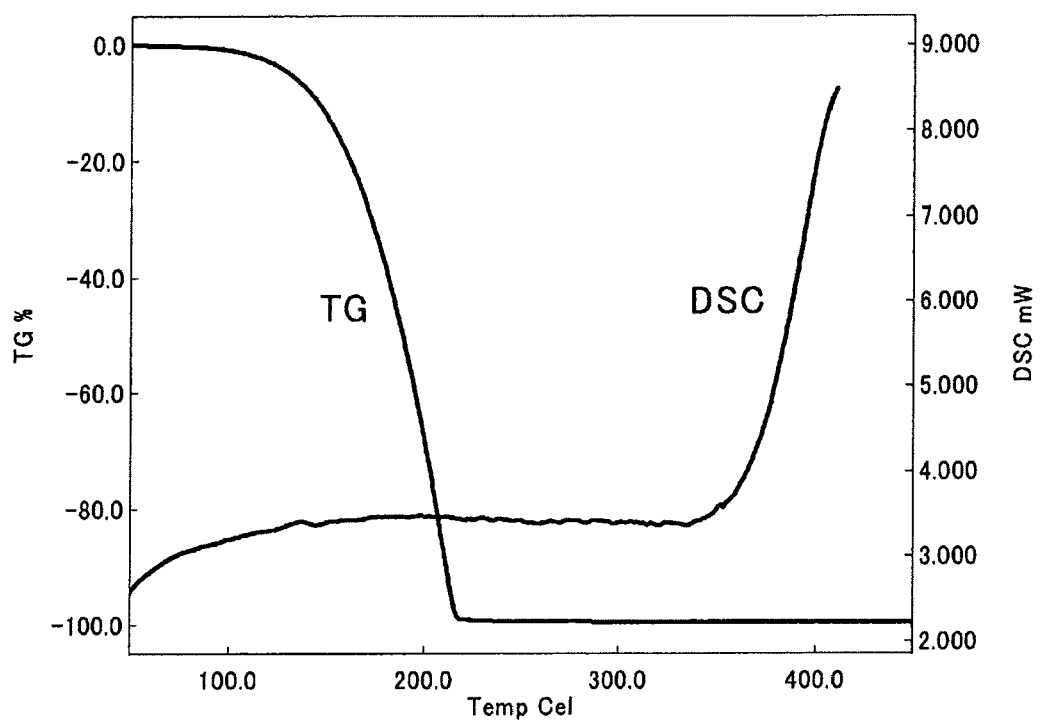
FIG. 17 is TG and DSC charts of Si($^t$PeNCHCHN$^t$Pe)(H)NHMe.
Figure 18:
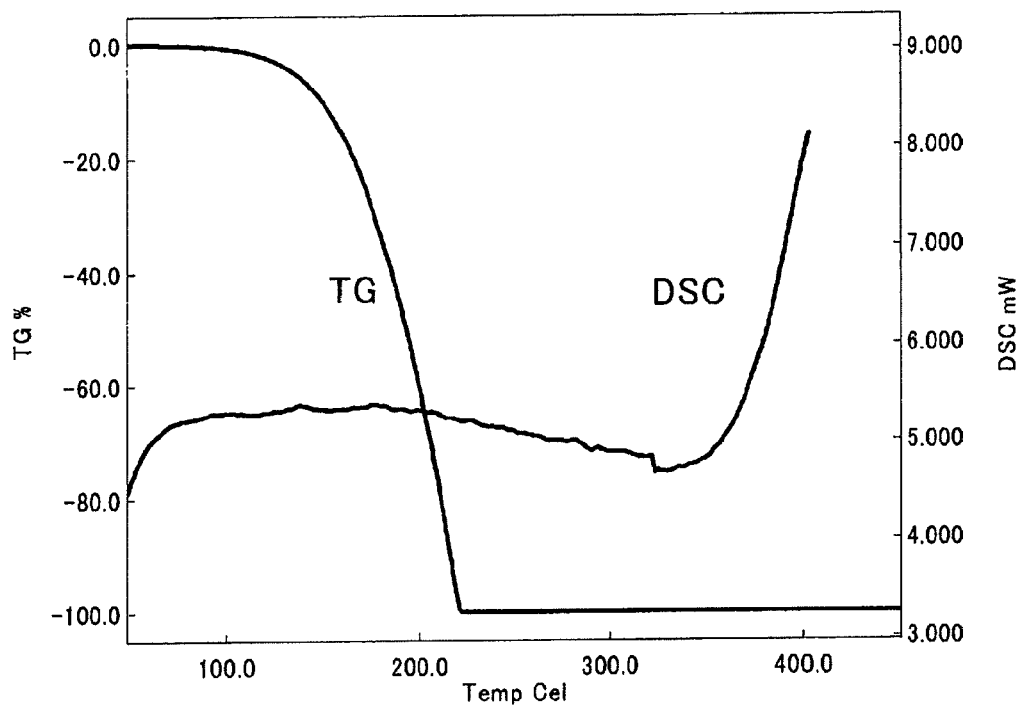
FIG. 18 is TG and DSC charts of Si($^t$PeNCHCHN$^t$Pe)(H)NHEt.
Figure 19:
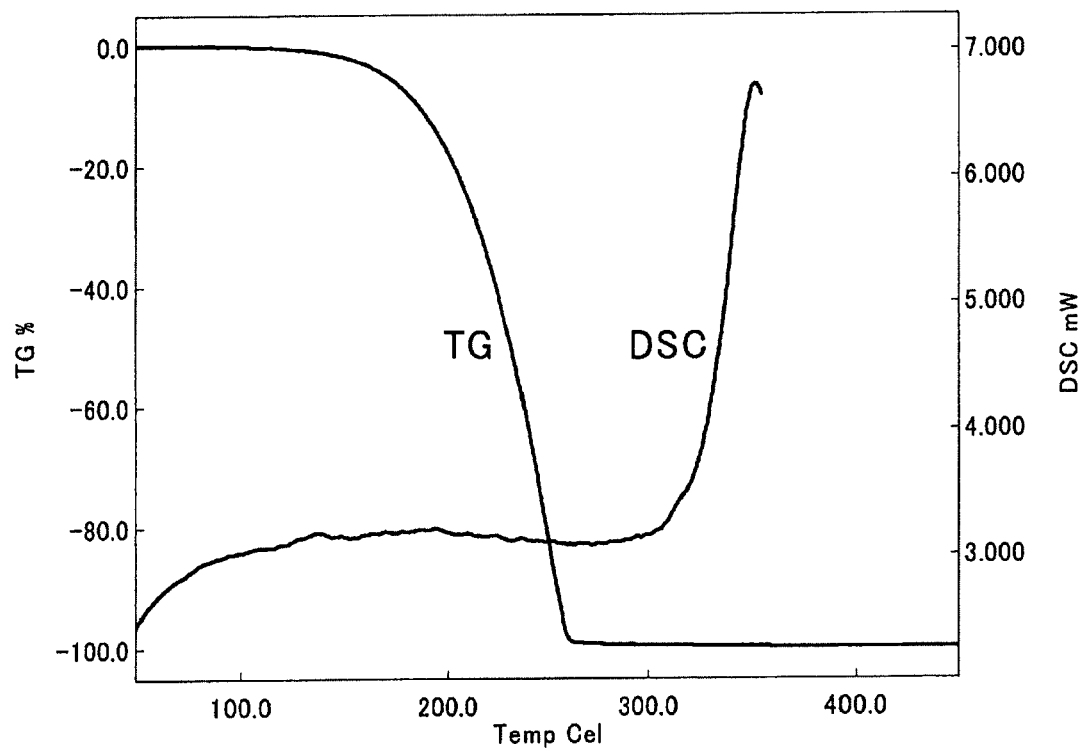
FIG. 19 is TG and DSC charts of Si($^t$OctNCHCHN$^t$Oct)(H)NH$_2$.
Figure 20:
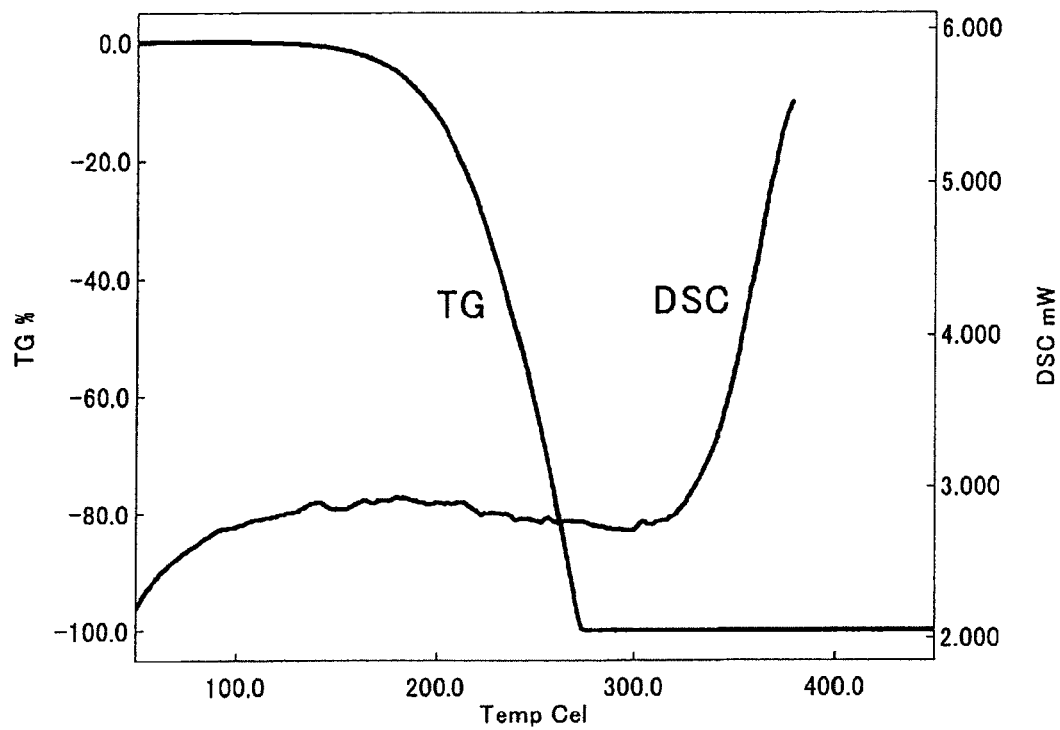
FIG. 20 is TG and DSC charts of Si($^t$OctNCHCHN$^t$Oct)(H)NHEt.
Figure 21:
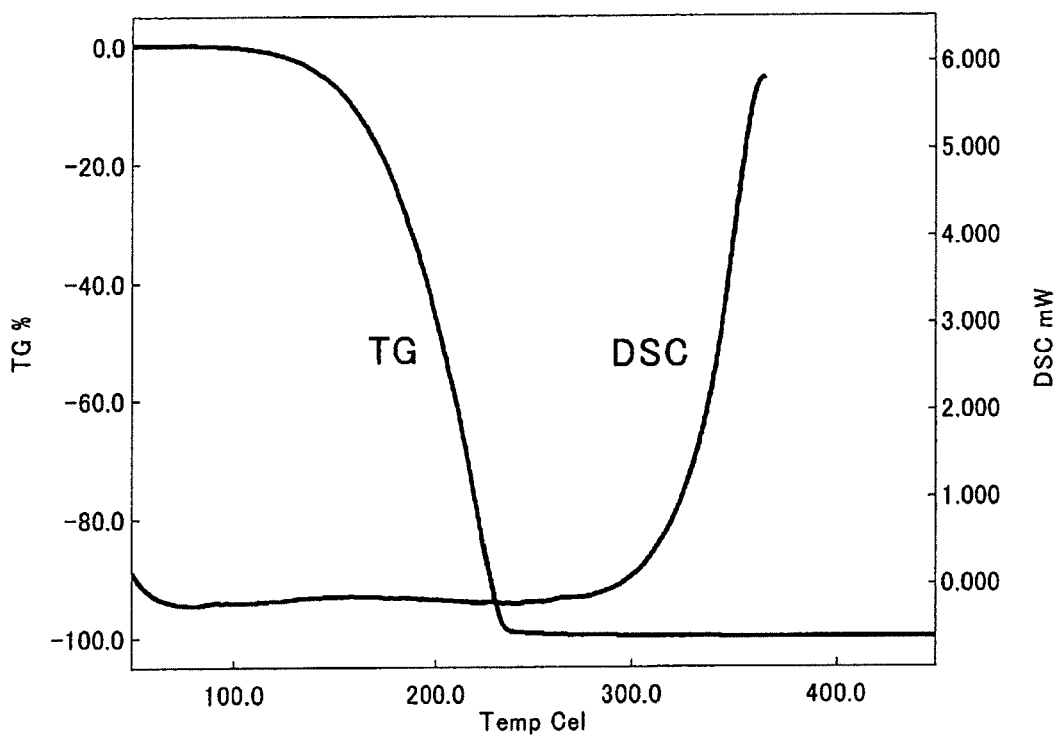
FIG. 21 is TG and DSC charts of Si($^t$BuNCHCHN$^t$Oct)(H)NH$_2$.
Figure 22:
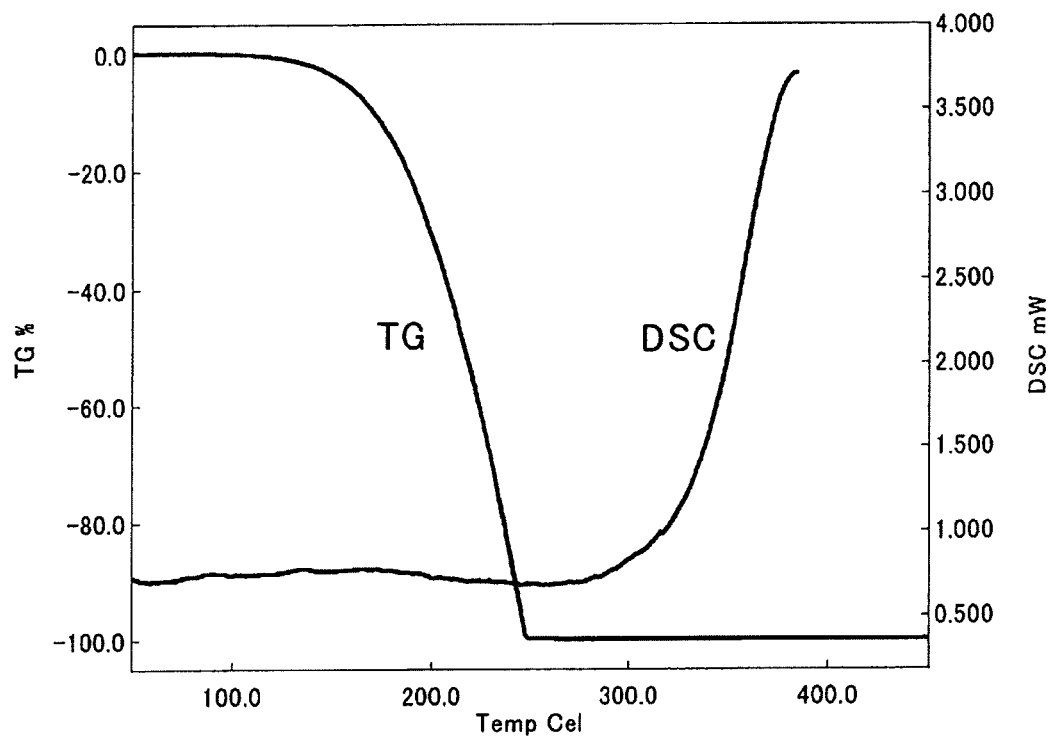
FIG. 22 is TG and DSC charts of Si($^t$BuNCHCHN$^t$Oct)(H)NHPr.
Figure 23:
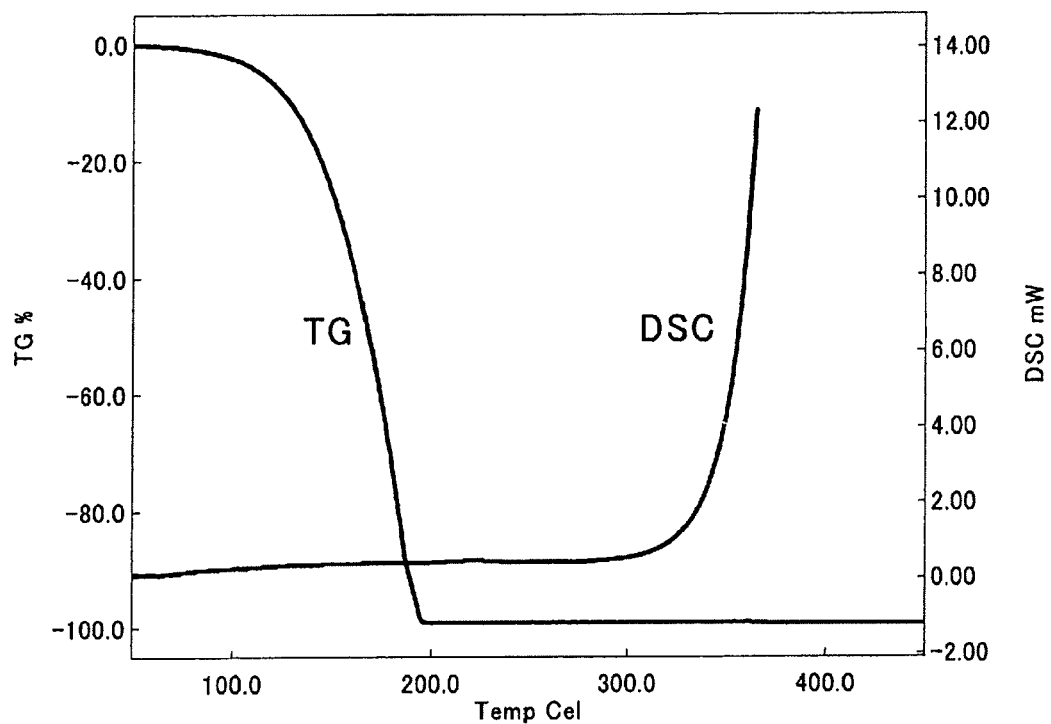
FIG. 23 is TG and DSC charts of Si($^t$BuNCHCHN$^t$Bu)(H)NCO.
Figure 24:
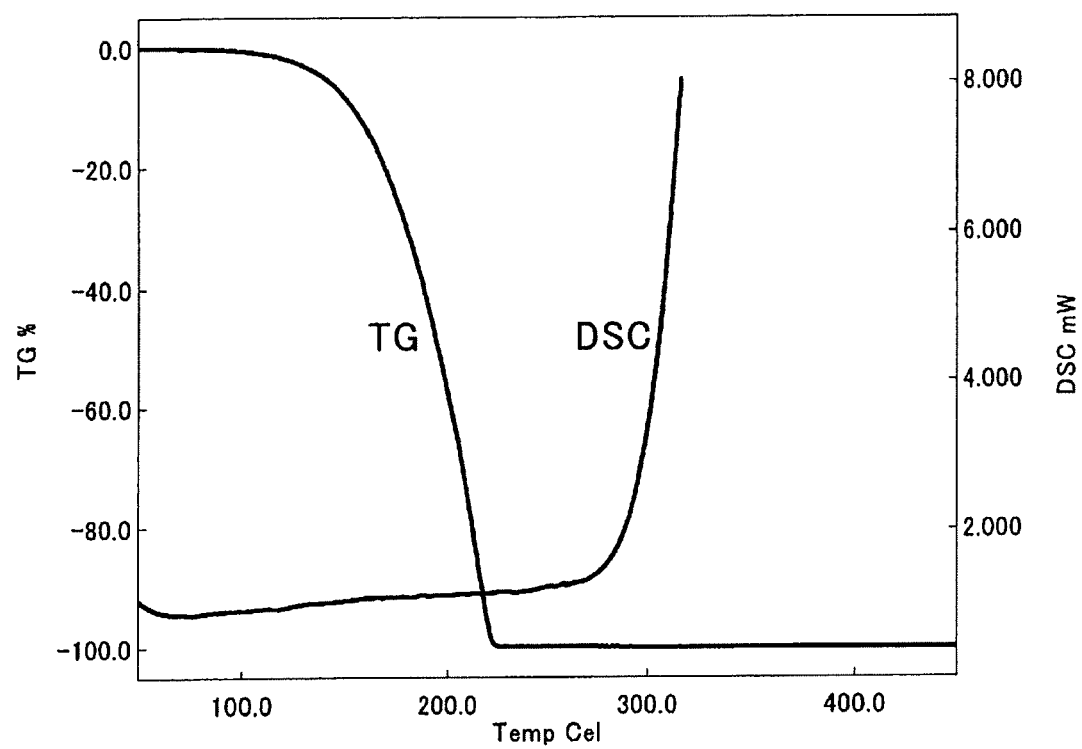
FIG. 24 is TG and DSC charts of Si($^t$BuNCHCHN$^t$Bu)(H)NCS.
Figure 25:
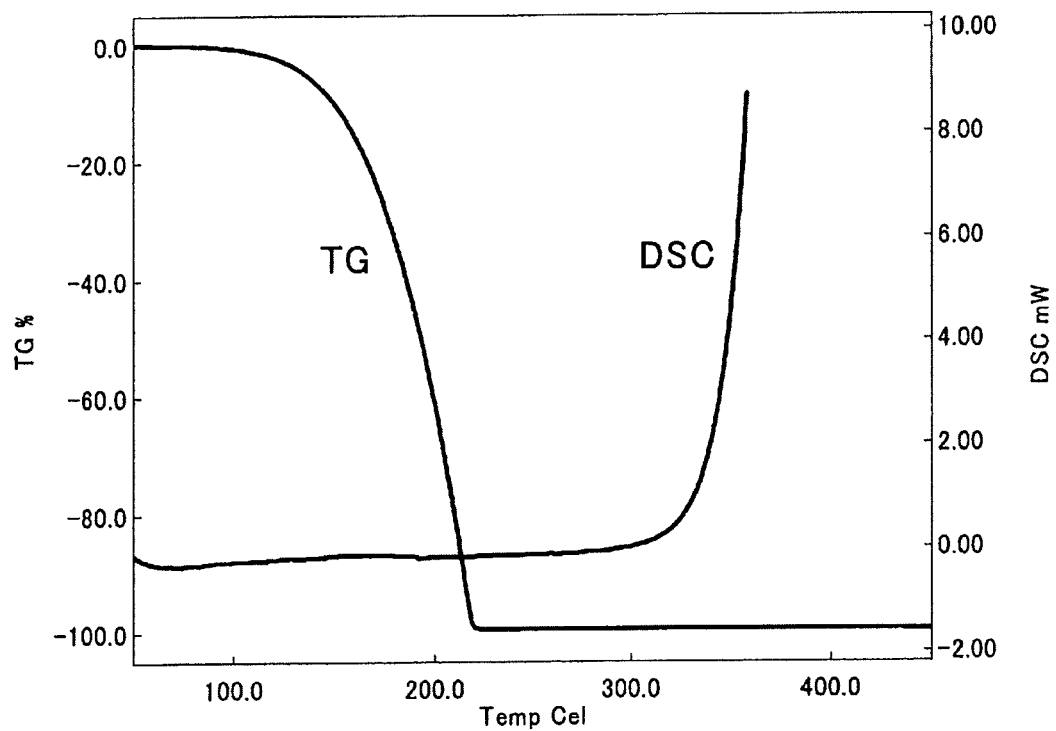
FIG. 25 is TG and DSC charts of Si($^t$PeNCHCHN$^t$Pe)(H)NCO.
Figure 26:
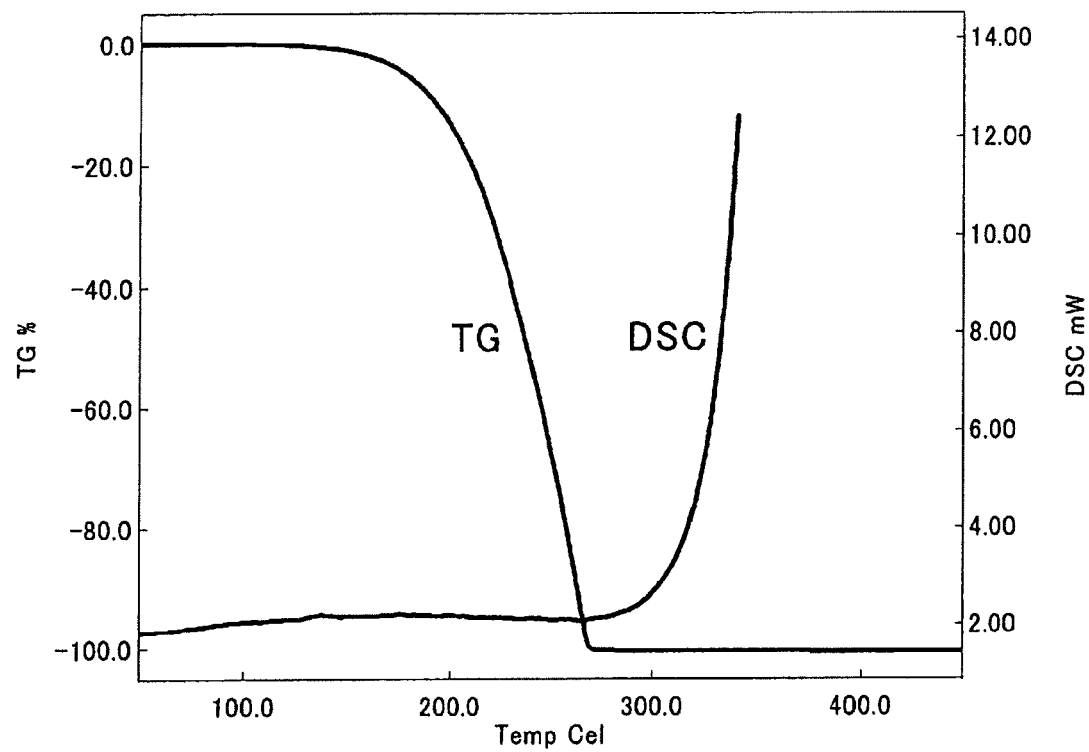
FIG. 26 is TG and DSC charts of Si($^t$OctNCHCHN$^t$Oct)(H)NCO.
Figure 27:
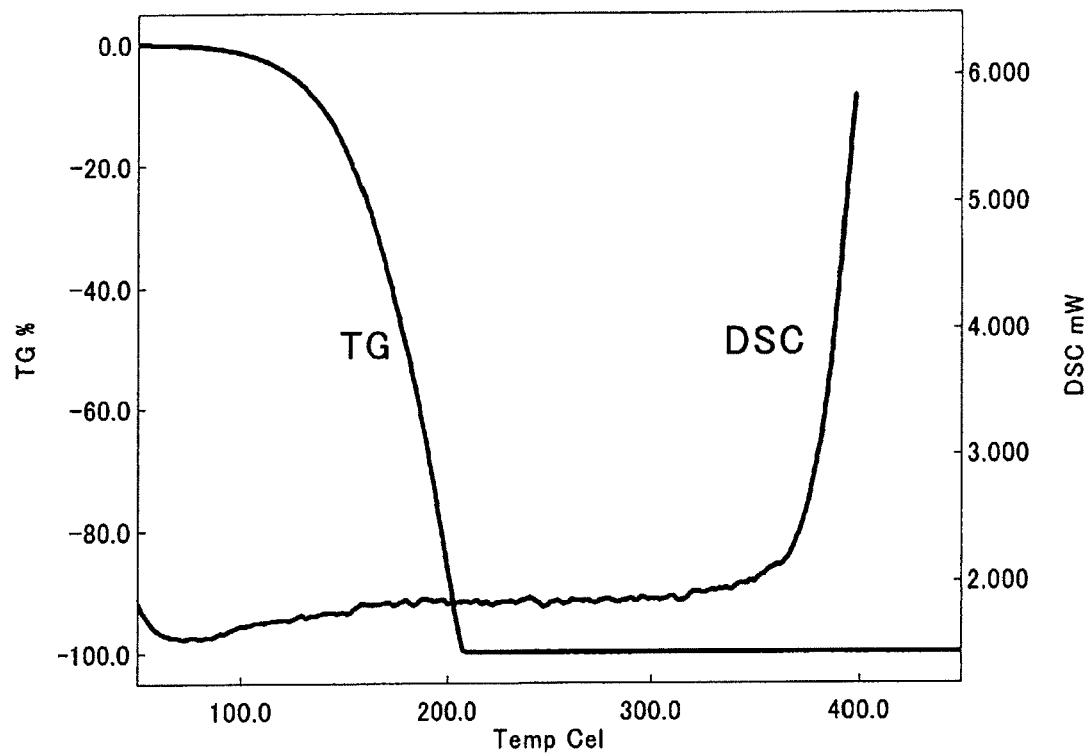
FIG. 27 is TG and DSC charts of Si($^t$BuNCHCHN$^t$Bu)(H)NEt$_2$.
Figure 28:
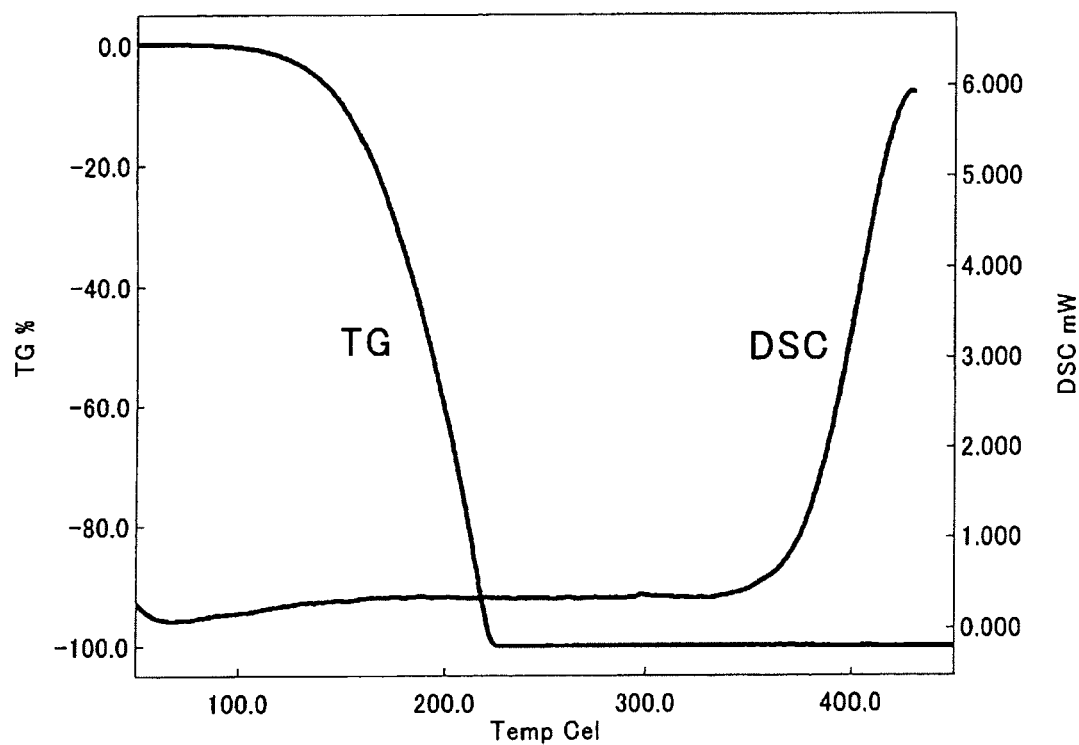
FIG. 28 is TG and DSC charts of Si($^t$BuNCHCHN$^t$Bu)(H)NBuMe.
Figure 29:
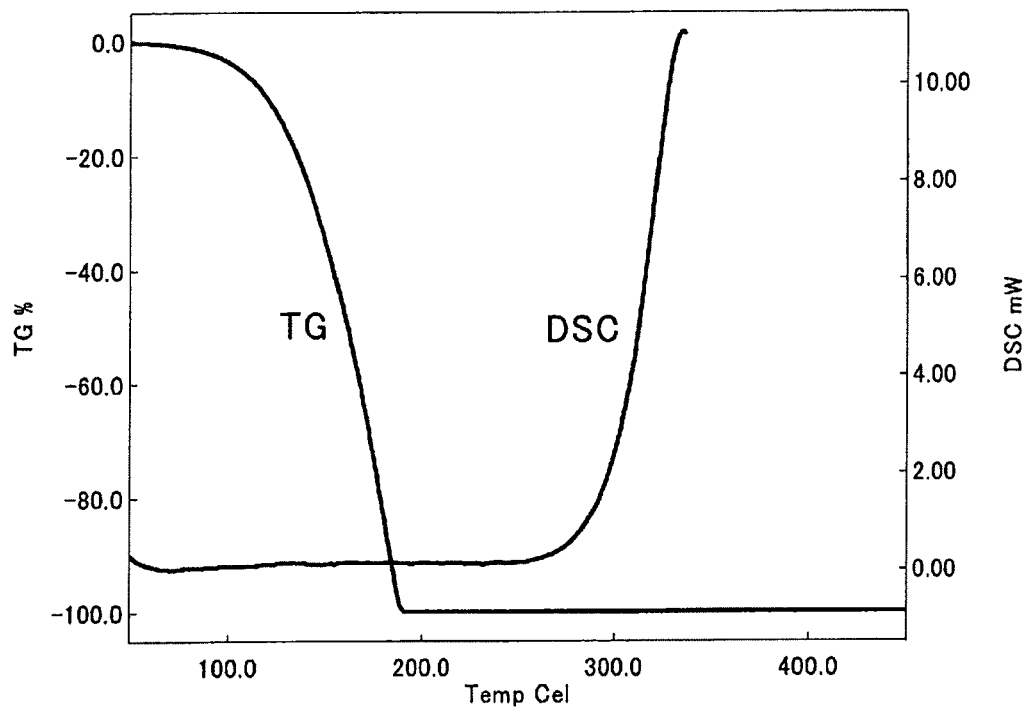
FIG. 29 is TG and DSC charts of Si($^t$BuNCHCHN$^t$Bu)(H)CHCH$_2$.
Figure 30:
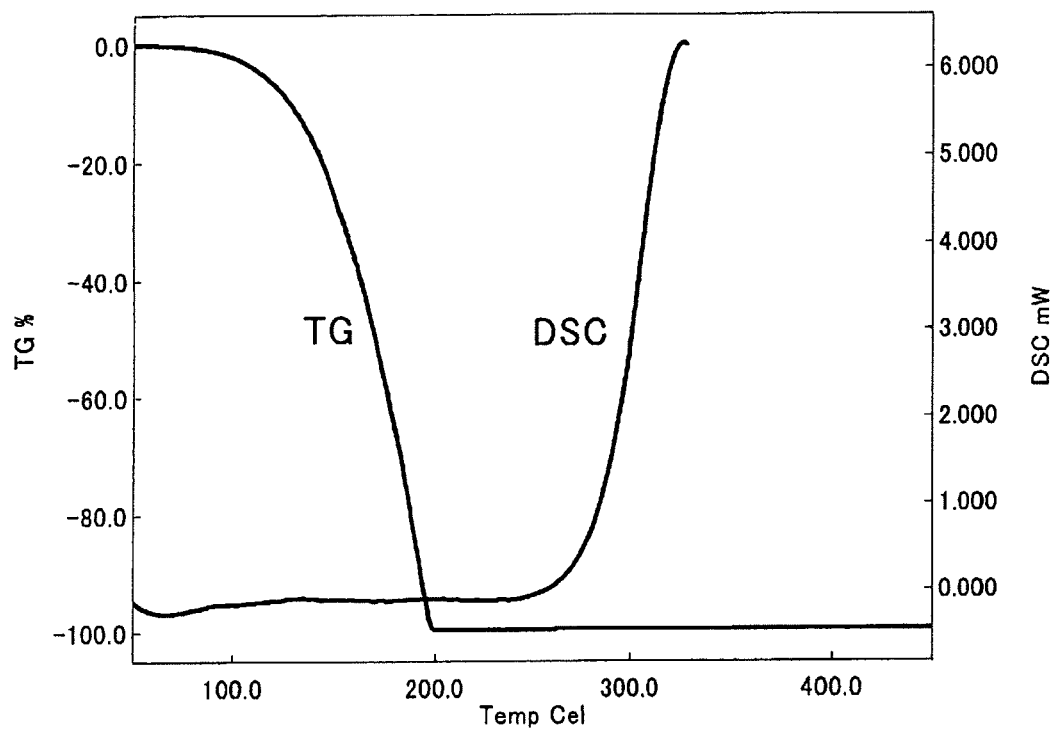
FIG. 30 is TG and DSC charts of Si($^t$BuNCHCHN$^t$Bu)(H)CH$_2$CHCH$_2$.
Figure 31:
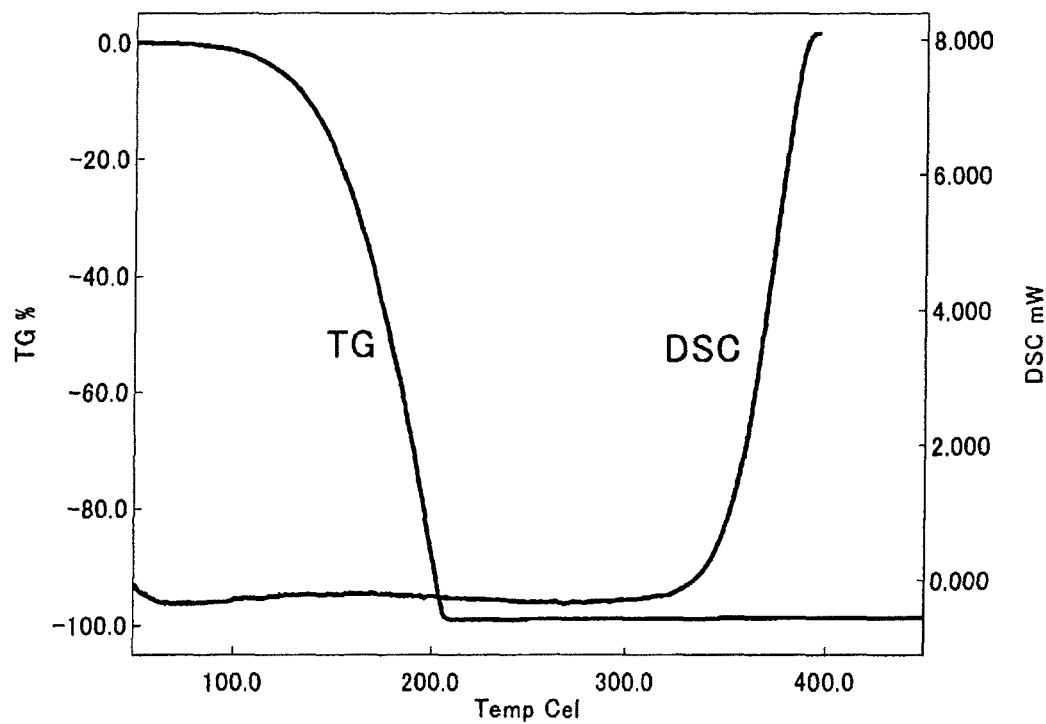
FIG. 31 is TG and DSC charts of Si($^t$BuNCHCHN$^t$Bu)(H)CHC(CH$_3$)$_2$.
Figure 32:
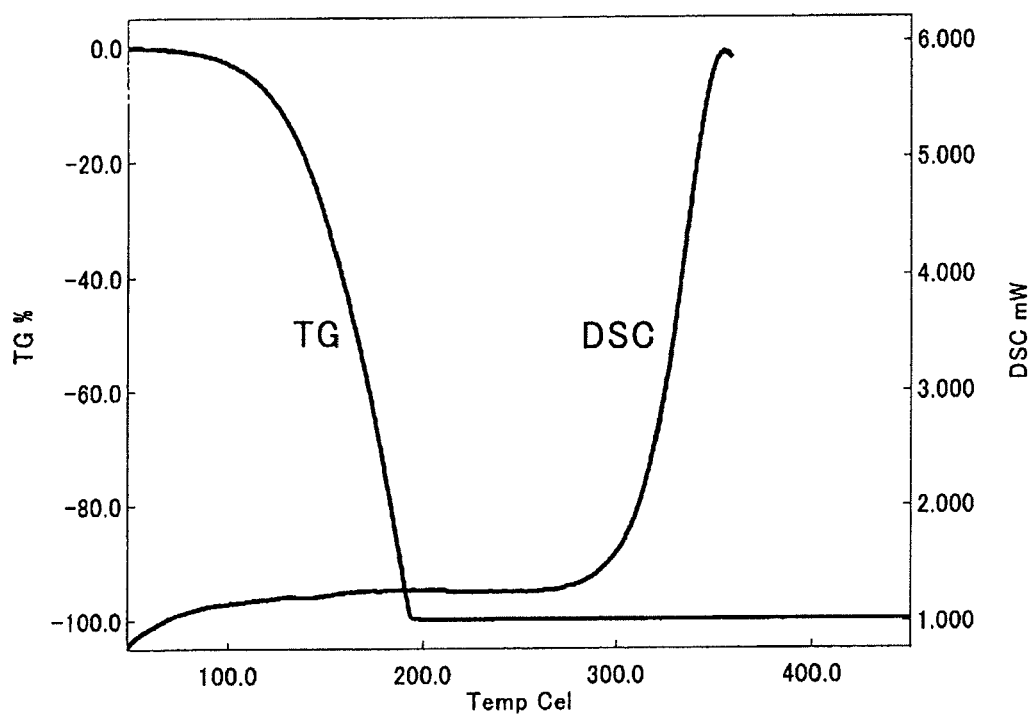
FIG. 32 is TG and DSC charts of Si($^t$BuNCHCHN$^t$Bu)(H)C(CH$_3$)CH$_2$.

The present invention is described in more detail below. First, definitions of $R^1$, $R^2$, $R^3$, $R^4$ and $R^5$ are described. The alkyl group having a carbon number of 3 to 12 represented by $R^1$ and $R^2$ may be linear, branched or cyclic, and specific examples include propyl group, isopropyl group, cyclopropyl group, butyl group, isobutyl group, sec-butyl group, tert-butyl group, cyclobutyl group, pentyl group, isopentyl group, neopentyl group, tert-pentyl group, 1-methylbutyl group, 2-methylbutyl group, 1,2-dimethylpropyl group, 1-ethylpropyl group, cyclopentyl group, hexyl group, isohexyl group, 1-methylpentyl group, 2-methylpentyl group, 3-methylpentyl group, 1,1-dimethylbutyl group, 1,2-dimethylbutyl group, 2,2-dimethylbutyl group, 1,3-dimethylbutyl group, 2,3-dimethylbutyl group, 3,3-dimethylbutyl group, 1-ethylbutyl group, 2-ethylbutyl group, 1,1,2-trimethylpropyl group, 1,2,2-trimethylpropyl group, 1-ethyl-1-methylpropyl group, 1-ethyl-2-methylpropyl group, cyclohexyl group, cyclopropylmethyl group, cyclopropylethyl group, cyclobutylmethyl group, heptyl group, cyclohexylmethyl group, 1,1-diethylpropyl group, 2-methylcyclohexyl group, 4-methylcyclohexyl group, octyl group, 1,1-diethyl-2-methylpropyl group, 2,5-dimethylcyclohexyl group, 3,5-dimethylcyclohexyl group, 1,1,3,3-tetramethylbutyl group, 1-methyl-1-propylbutyl group, 1,1,2,3,3-pentamethylbutyl group, 1,1-diethyl-3,3-dimethylbutyl group, adamantyl group, 1,1-dimethyloctyl group, 1,1-dipropylbutyl group, 1,1-dimethyldecyl group, 1,1-diethyloctyl group, and 1-butyl-1-propylpentyl group.

From the standpoint that the hydrosilane derivative (1') has a high vapor pressure and is easy to handle as a thin-film forming material and that when a film is deposited using the hydrosilane derivative (1') as the material, the deposition rate of a silicon-containing thin film is high, each of $R^1$ and $R^2$ is independently, preferably an alkyl group having a carbon number of 3 to 8, more preferably a secondary or tertiary alkyl group having a carbon number of 3 to 5, still more preferably a tert-butyl group or a tert-pentyl group.

Examples of the alkyl group having a carbon number of 1 to 12 represented by $R^3$ include methyl group, ethyl group, propyl group, isopropyl group, cyclopropyl group, butyl group, isobutyl group, sec-butyl group, tert-butyl group, cyclobutyl group, pentyl group, isopentyl group, neopentyl group, tert-pentyl group, 1-methylbutyl group, 2-methylbutyl group, 1,2-dimethylpropyl group, 1-ethylpropyl group, cyclopentyl group, hexyl group, isohexyl group, 1-methylpentyl group, 2-methylpentyl group, 3-methylpentyl group, 1,1-dimethylbutyl group, 1,2-dimethylbutyl group, 2,2-dimethylbutyl group, 1,3-dimethylbutyl group, 2,3-dimethylbutyl group, 3,3-dimethylbutyl group, 1-ethylbutyl group, 2-ethylbutyl group, 1,1,2-trimethylpropyl group, 1,2,2-trimethylpropyl group, 1-ethyl-1-methylpropyl group, 1-ethyl-2-methylpropyl group, cyclohexyl group, cyclopropylmethyl group, cyclopropylethyl group, cyclobutylmethyl group, heptyl group, cyclohexylmethyl group, 1,1-diethylpropyl group, 2-methylcyclohexyl group, 4-methylcyclohexyl group, octyl group, nonyl group, decyl group, undecyl group, dodecyl group, 1,1-diethyl-2-methylpropyl group, 2,5-dimethylcyclohexyl group, 3,5-dimethylcyclohexyl group, 1,1,3,3-tetramethylbutyl group, 1-methyl-1-propylbutyl group, 1,1,2,3, 3-pentamethylbutyl group, 1,1-diethyl-3,3-dimethylbutyl group, adamantyl group, 1,1-dimethyloctyl group, 1,1-dipropylbutyl group, 1,1-dimethyldecyl group, 1,1-diethyloctyl group, and 1-butyl-1-propylpentyl group.

These alkyl groups may be substituted with a fluorine atom, and examples of the substituted alkyl group include fluoromethyl group, difluoromethyl group, trifluoromethyl group, 1-fluoroethyl group, 2-fluoroethyl group, 1,1-difluoroethyl group, 2,2-difluoroethyl group, 2,2,2-trifluoroethyl group, perfluoroethyl group, 1-fluoropropyl group, 2-fluoropropyl group, 3-fluoropropyl group, 1,1-difluoropropyl group, 2,2-difluoropropyl group, 3,3-difluoropropyl group, 3,3,3-trifluoropropyl group, perfluoropropyl group, 1-trifluoromethyl-2,2,2-trifluoroethyl group, perfluoroisopropyl group, perfluorobutyl group, perfluoroisobutyl group, perfluoro-sec-butyl group, perfluoro-tert-butyl group, perfluoropentyl group, perfluoroisopentyl group, perfluoroneopentyl group, perfluoro-tert-pentyl group, perfluorohexyl group, perfluorocyclohexyl group, perfluoroheptyl group, perfluorooctyl group, perfluorononyl group, perfluorodecyl group, perfluoroundecyl group, and perfluorododecyl group.

From the standpoint that the hydrosilane derivative (1') has a high vapor pressure and is a liquid and easy to handle as a thin-film forming material and that when a film is deposited using the hydrosilane derivative (1') as the material, the deposition rate of a silicon-containing thin film is high, $R^3$ is preferably an alkyl group having a carbon number of 1 to 8, which may be substituted with fluorine, more preferably an alkyl group having a carbon number of 1 to 4, and specifically, still more preferably a methyl group, an ethyl group, a propyl group, an isopropyl group, a cyclopropyl group, a butyl group, an isobutyl group, a sec-butyl group, a tert-butyl group, a cyclobutyl group, or the like.

Examples of the alkyl group having a carbon number of 1 to 4 represented by $R^4$ and $R^5$ include methyl group, ethyl group, propyl group, isopropyl group, cyclopropyl group, butyl group, isobutyl group, sec-butyl group, tert-butyl group, and cyclobutyl group.

Definitions of the substituents represented by Z and Za in the description of the present invention are described below. Za represents an isocyanato group, an isothiocyanato group, an amino group, a monosubstituted amino group represented by $NHR^3$, an N-methyl-alkylamino group represented by $N(CH_3)R^4$, or an alkenyl group having a carbon number of 2 to 6 (wherein $R^3$ and $R^4$ have the same meanings as above). Z is a broader term of Za and represents an isocyanato group, an isothiocyanato group, an amino group, a monosubstituted amino group represented by $NHR^3$, a disubstituted amino group represented by $NR^4R^5$, or an alkenyl group having a carbon number of 2 to 6 (wherein $R^3$, $R^4$ and $R^5$ have the same meanings as above).

The alkenyl group having a carbon number of 2 to 6 may be linear, branched or cyclic, and specific examples thereof include vinyl group, prop-1-en-1-yl group, prop-1-en-2-yl group, prop-2-en-1-yl group, cycloprop-1-enyl group, cycloprop-2-enyl group, but-1-en-1-yl group, but-1-en-2-yl group, but-3-en-2-yl group, but-3-en-1-yl group, but-2-en-1-yl group, but-2-en-2-yl group, 2-methylprop-1-en-1-yl group, cyclobut-1-enyl group, cyclobut-2-enyl group, pent-1-en-1-yl group, pent-1-en-2-yl group, pent-1-en-3-yl group, pent-4-en-2-yl group, pent-4-en-1-yl group, pent-2-en-1-yl group, pent-2-en-2-yl group, pent-2-en-3-yl group, pent-3-en-2-yl group, pent-3-en-1-yl group, 2-methylbut-1-en-1-yl group, 2-methylbut-3-en-2-yl group, 3-methylbut-2-en-1-yl group, 3-methylbut-2-en-2-yl group, 2-methylenebutyl group, 2-methylbut-2-en-1-yl group, cyclopent-1-enyl group, cyclopent-2-enyl group, cyclopent-3-enyl group, hex-1-en-1-yl group, hex-1-en-2-yl group, hex-1-en-3-yl group, hex-5-en-1-yl group, hex-5-en-2-yl group, hex-5-en-3-yl group, 2-methylpent-4-en-2-yl group, 4-methylpent-1-en-3-yl group, 3-methylpent-1-en-3-yl group, 2-methylpent-1-en-3-yl group, 4-methylpent-4-en-1-yl group, 3-methylenepentyl group, 2-methylenepentyl group, 3-methylene-2-methylenebutyl group, 2,3-dimethylbut-3-en-2-yl group, cyclohex-1-enyl group, cyclohex-2-enyl group, and cyclohex-3-enyl group.

From the standpoint that the hydrosilane derivative (1') has a high vapor pressure, an alkenyl group having a carbon number of 2 to 4 is preferred. Specifically, vinyl group, prop-1-en-1-yl group, prop-1-en-2-yl group, prop-2-en-1-yl group, cycloprop-1-enyl group, cycloprop-2-enyl group, but-1-en-1-yl group, but-1-en-2-yl group, but-3-en-2-yl group, but-3-en-1-yl group, but-2-en-1-yl group, but-2-en-2-yl group, 2-methylprop-1-en-1-yl group, cyclobut-1-enyl group and cyclobut-2-enyl group are preferred, and vinyl group, prop-1-en-1-yl group, prop-1-en-2-yl group and prop-2-en-1-yl group are more preferred.

From the standpoint that in the case of producing a silicon oxide thin film by using the hydrosilane derivative (1) as the material in the co-presence of an oxygen gas, the deposition rate of the silicon-containing thin film is high, Za is preferably an amino group, a monosubstituted amino group represented by $NHR^3$, an N-methyl-alkylamino group represented by $N(CH_3)R^4$, or an alkenyl group having a carbon number of 2 to 4, more preferably an amino group or a monosubstituted amino group represented by $NHR^3$, still more preferably an amino group, a methylamino group, an ethylamino group, a propylamino group, an isopropylamino group, a cyclopropylamino group, a butylamino group, an isobutylamino group, a sec-butylamino group or a tert-butyl amino group. Also, from the standpoint that the material has a low thermal decomposition temperature and is suited for the production of a silicon-containing thin film at a low temperature, Za is preferably an amino group, a monosubstituted amino group represented by $NHR^3$, an isocyanato group, or an alkenyl group having a carbon number of 2 to 4. Furthermore, from the standpoint that the deposition rate of the silicon-containing thin film is high even at a low temperature, Za is more preferably an amino group.

From the standpoint that in the case of producing a silicon oxide thin film by using the hydrosilane derivative (1') as the material in the co-presence of an oxygen gas, the deposition rate of the silicon-containing thin film is high, Z is preferably an amino group, a monosubstituted amino group represented by $NHR^3$, an N-methyl-alkylamino group represented by $N(CH_3)R^4$, or an alkenyl group having a carbon number of 2 to 4, more preferably an amino group or a monosubstituted amino group represented by $NHR^3$, still more preferably an amino group, a methylamino group, an ethylamino group, a propylamino group, an isopropylamino group, a cyclopropylamino group, a butylamino group, an isobutylamino group, a sec-butylamino group or a tert-butyl amino group. Also, from the standpoint that the material has a low thermal decomposition temperature and is suited for the production of a silicon-containing thin film at a low temperature, Z is preferably an amino group, a monosubstituted amino group represented by $NHR^3$, an isocyanato group, or an alkenyl group having a carbon number of 2 to 4. Furthermore, from the standpoint that the deposition rate of the silicon-containing thin film is high even at a low temperature, Z is more preferably an amino group.

The production method of the present invention is described below. The hydrosilane derivative (1') of the present invention can be produced through the step A shown in the following reaction formula.

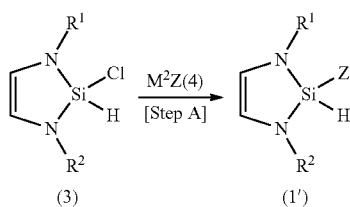

[Chem. 19]

The compound $M^2Z$ (4) for use in the step A can be used by determining $M^2$ as described above according to the type of the substituent Z of a desired hydrosilane derivative (1'). Specifically, the compound $M^2Z$ (4) used is appropriately selected from ammonia, lithium amide, a primary amine represented by $NH_2R^3$, a secondary amine represented by $NHR^4R^5$, a lithium(alkylamide) represented by $LiNHR^3$, a lithium(dialkylamide) represented by $LiNR^4R^5$, sodium cyanate, potassium cyanate, sodium thiocyanate, potassium thiocyanate, and an alkenyl magnesium halide having a carbon number of 2 to 6 ($R^3$, $R^4$ and $R^5$ have the same meanings as above). More specifically, sodium cyanate or potassium cyanate is used as the compound (4) when Z is an isocyanato group; sodium thiocyanate or potassium thiocyanate is used as the compound (4) when Z is an isothiocyanato group; ammonia or lithium amide is used as the compound (4) when Z is an amino group; a primary amine $NH_2R^3$ or a lithium (alkylamide) $LiNHR^3$ is used as the compound (4) when Z is a monosubstituted amino group $NHR^3$; a secondary amine $NHR^4R^5$ or a lithium(dialkylamide) represented by $LiNR^4R^5$ is used as the compound (4) when Z is a disubstituted amino group $NR^4R^5$; and an alkenyl magnesium halide is used as the compound (4) when Z is an alkenyl group having a carbon number of 2 to 6 ($R^3$, $R^4$ and $R^5$ have the same meaning as above). Examples of the halogen atom of the alkenyl magnesium halide include a chlorine atom, a bromine atom and an iodine atom, and in view of good yield of the hydrosilane derivative (1'), the halogen atom is preferably a chlorine atom or a bromine atom, more preferably a bromine atom. In the step A, if desired, tertiary amines such as triethylamine and diethyl(isopropyl)amine, and pyridines may be added as a reaction aid.

In view of good yield of the hydrosilane derivative (1'), the step A is preferably performed in an organic solvent. The organic solvent which can be used is not limited as long as it is a solvent not inhibiting the reaction. For example, in the case where ammonia, a primary amine $NH_2R^3$ or a secondary amine $NHR^4R^5$ is used as the compound (4), examples of the solvent include a hydrocarbon solvent such as pentane, hexane, heptane, octane, cyclohexane, methylcyclohexane, ethylcyclohexane, benzene, toluene, xylene and ethylbenzene, and an ether solvent such as diethyl ether, diisopropyl ether, cyclopentylmethyl ether, cyclopentyl ethyl ether, dioxane, tetrahydrofuran and 1,2-dimethoxyethane. One of these may be used alone, or a mixture thereof in an arbitrary ratio may be used. In view of good yield of the hydrosilane derivative (1'), hexane, heptane, tetrahydrofuran, or a mixed solvent of tetrahydrofuran and hexane or heptane is preferred. Also, in the case where lithium amide, a lithium(alkylamide) $LiNHR^3$, a lithium(dialkylamide) $LiNR^4R^5$, sodium cyanate, potassium cyanate, sodium thiocyanate, potassium thiocyanate or an alkenyl magnesium halide is used as the compound (4), examples of the solvent include an ether solvent such as diethyl ether, diisopropyl ether, cyclopentyl methyl ether, cyclopentyl ethyl ether, dioxane, tetrahydrofuran and 1,2-dimethoxyethane, and a mixed solvent of this ether solvent and a hydrocarbon solvent such as pentane, hexane, heptane, octane, cyclohexane, methylcyclohexane, ethylcyclohexane, benzene, toluene, xylene and ethylbenzene. In view of good yield of the hydrosilane derivative (1'), tetrahydrofuran or 1,2-dimethoxyethane is more preferred.

In the step A, the amount of the solvent used is not particularly limited, and a diazasilacyclopentene derivative (1') can be produced in good yield by using an appropriately selected amount of a solvent.

The mixing ratio between the chlorosilane derivative (3) and the compound (4) is described below. In the case where the compound (4) used in the step A is ammonia, a primary amine $NH_2R^3$ or a secondary amine $NHR^5R^6$, when tertiary amines or pyridines are not added as a reaction aid, the hydrosilane derivative (1') can be produced in good yield by using the compound (4) in an amount of 2 or more equivalents relative to the chlorosilane derivative. In the case of adding a reaction aid, the amount of the compound (4) used may be decreased according to the amount of the reaction aid added, and, for example, when the reaction aid is used in an amount of 1 or more equivalents relative to the chlorosilane derivative (3), the hydrosilane derivative (1') can be produced in good yield by using the compound (4) in an amount of 1 or more equivalents relative to the chlorosilane derivative (3). Also, in the case where the compound (4) used in the step A is lithium amide, lithium(alkylamide) $LiNHR^3$, lithium(dialkylamide) $LiNR^4R^5$, sodium cyanate, potassium cyanate, sodium thiocyanate, potassium thiocyanate or an alkenyl magnesium halide, the hydrosilane derivative (1') can be produced in good yield by using the compound (4) in an amount of 1 or more equivalents relative to the chlorosilane derivative (3).

In the step A, the reaction temperature and the reaction time are not particularly limited and are appropriately selected from the ranges of preferably from 0 to 200° C. and from 10 minutes to 120 hours, whereby the hydrosilane derivative (1') can be produced in good yield. Examples of the gas which can be used for the atmosphere in the step A include dry air, nitrogen, helium, neon and argon. In view of good yield of the hydrosilane derivative (1'), the step A is preferably performed in a nitrogen or argon atmosphere.

The hydrosilane derivative (1') produced through the step A may be purified, if desired, by appropriately selecting a general purification method such as filtration, extraction, distillation, sublimation and crystallization.

The hydrosilane derivative (1') of the present invention can be also produced by a method of performing two steps 1 and 2 shown in the following reaction formula.

[Chem. 20]

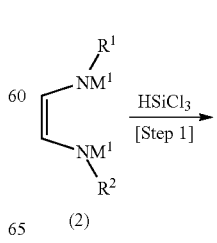

-continued

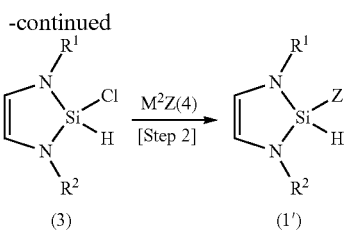

(wherein $R^1$, $R^2$, $M^1$, $Z$, $R^3$, $R^4$, $R^5$ and $M^2$ have the same meanings as above). More specifically, step 1 of reacting a vinylenediaminide alkali metal salt (2) with trichlorosilane to produce a chlorosilane derivative (3), and step 2 of reacting the chlorosilane derivative (3) with the compound (4) to produce a hydrosilane derivative (1') are performed, whereby the hydrosilane derivative (1') can be produced.

The step 1 is descried in detail below. The vinylenediaminide alkali metal salt (2) used in the step 1 or a raw material for the synthesis thereof, that is, N,N'-dialkyl-1,4-diaza-1,3-butadiene ($R^1N$=CHCH=$NR^2$), can be produced according to the method described, for example, in *Journal of the American Chemical Society*, Vol. 120, page 12714 (1998) and *Journal of Organometallic Chemistry*, Vol. 301, page 183 (1986).

In view of good yield of the chlorosilane derivative (3), $M^1$ is preferably a lithium atom.

In view of good yield of the chlorosilane derivative (3), the step 1 is preferably performed in an organic solvent. The organic solvent which can be used is not limited as long as it is a solvent not inhibiting the reaction. Examples of the solvent include an ether solvent such as diethyl ether, diisopropyl ether, cyclopentyl methyl ether, cyclopentyl ethyl ether, dioxane, tetrahydrofuran and 1,2-dimethoxyethane, and a mixed solvent of this ether solvent and a hydrocarbon solvent such as pentane, hexane, heptane, octane, cyclohexane, methylcyclohexane, ethylcyclohexane, benzene, toluene, xylene and ethylbenzene. In view of good yield of the chlorosilane derivative (3), tetrahydrofuran or a mixed solvent of tetrahydrofuran and hexane is more preferred. The amount of the solvent used is not particularly limited, and the chlorosilane derivative (3) can be produced in good yield by using the solvent in an appropriately selected amount.

The amount of the vinylenediaminide alkali metal salt (2) used in the step 1 is not particularly limited, but from the standpoint that the chlorosilane derivative (3) can be produced in good yield, it is preferred to use trichlorosilane in an amount of 0.9 to 1.1 equivalents relative to the vinylenediaminide alkali metal salt (2), and from the standpoint that the vinylenediaminide alkali metal salt (2) and trichlorosilane can be used in just proportion, it is more preferred to use trichlorosilane in an amount of 1.0 equivalents relative to the vinylenediaminide alkali metal salt (2).

In the step 1, the reaction temperature and the reaction time are not particularly limited and are appropriately selected from the ranges of preferably from 0 to 100° C. and from 10 minutes to 120 hours, whereby the chlorosilane derivative (3) can be produced in good yield. Also, in view of good yield of the chlorosilane derivative (3), examples of the gas which can be used for the atmosphere of this reaction include inert gases such as nitrogen, helium, neon and argon. In view of good yield of the chlorosilane derivative (3), the reaction is more preferably performed in a nitrogen or argon atmosphere.

The chlorosilane derivative (3) produced through the step 1 may be purified, if desired, by appropriately selecting a general purification method such as filtration, extraction, distillation, sublimation and crystallization. The chlorosilane derivative (3) need not be necessarily isolated, and the crude chlorohydrosilane derivative (3) may be directly used as the raw material in the step 2 or may be used in one-pot system for the reaction of the step 2 after the completion of reaction in the step 1.

The step 2 can be performed under the same conditions as in the step A above.

The method for producing a silicon-containing thin film, comprising using the hydrosilane derivative (1') as the material, is described in detail below. A silicon-containing thin film may be produced not only by a method using the hydrosilane derivative (1') alone as the material for thin film production, but also by using the hydrosilane derivative in combination with other silicon compounds as the material for thin film production. Furthermore, a silicon-containing thin film may be produced by using oxygen gas, ozone, nitrogen gas, hydrogen gas, water, hydrogen peroxide, ammonia, alcohols, carboxylic acids or the like as the material for thin film production in combination with the hydrosilane derivative (1'). Examples of the thin film that can be produced include thin films of silicon dioxide, silicon nitride, silicon carbide, silicon oxynitride and silicate. Among others, a silicon dioxide thin film or a silicon nitride thin film can be efficiently produced. More specifically, for example, a silicon oxide thin film can be produced by using the hydrosilane derivative (1') of the present invention as the material and using, in combination, a material for thin film production appropriately selected from the group consisting of oxygen source compounds such as oxygen, ozone, water, hydrogen peroxide, alcohols and carboxylic acids. Also, a silicon nitride thin film can be produced by using a nitrogen source compound such as ammonia, amines and hydrazine in combination as the material for thin film production. Furthermore, a silicon nitride thin film can be produced by using the hydrosilane derivative (1') alone without using another material for thin film production in combination. In addition, various metal silicide thin films can be produced by using other metal compounds, for example, a compound containing a transition metal such as scandium, yttrium, rare earth element, titanium, zirconium, hafnium, vanadium, niobium, tantalum, chromium, molybdenum, tungsten, manganese, technetium, rhenium, iron, ruthenium, osmium, cobalt, rhodium, iridium, nickel, palladium, platinum, copper, silver, gold, zinc and cadmium, or a typical metal-containing compound, as the material for thin film production in combination with the hydrosilane derivative (1'). Also, a thin film of a composite oxide with a typical metal or a transition metal may be produced.

Examples of the specific method for producing a silicon-containing thin film include a vapor deposition method such as CVD method and ALD method, and a solution method such as dip coating method, spin coating method and inkjet method. A vapor deposition method is preferred, because a uniform thin film is easily formed also on the surface of a substrate having a three-dimensionally shaped structure. For example, in the case of producing a silicon-containing thin film by the CVD method or the ALD method, the hydrosilane derivative (1') is vaporized and fed as a gas to a reaction chamber. Examples of the method for vaporizing the hydrosilane derivative (1') include a bubbling method and a liquid injection method. The bubbling method as used in the description of the present invention is a method where the hydrosilane derivative (1') is charged into a material vessel kept at a fixed temperature by being placed in a constant temperature bath and a carrier gas incapable of reacting with the hydrosilane derivative (1'), such as helium, neon, argon, krypton, xenon and nitrogen, is blown into the vessel to thereby vaporize the hydrosilane derivative (1'). The liquid injection method is a method where the hydrosilane derivative (1') in a liquid state is fed to a vaporizer and, for example, heated in the vaporizer to thereby vaporize the hydrosilane derivative (1'). In the liquid injection method, the hydrosilane derivative (1') can be used alone as the material for thin film production, or a solution obtained by dissolving the hydrosilane derivative (1') in an organic solvent may be used. The organic solvent when using the hydrosilane derivative (1') as a solution is not particularly limited as long as it is a solvent incapable of reacting with the hydrosilane derivative (1'), and examples thereof include ethers such as 1,2-dimethoxyethane, diglyme, triglyme, dioxane, tetrahydrofuran, cyclopentyl methyl ether and cyclopentyl ethyl ether, alkanes such as pentane, hexane, cyclohexane, methylcyclohexane, ethylcyclohexane, heptane, octane, nonane and decane, and aromatic hydrocarbons such as benzene, toluene, ethylbenzene and xylene. One of these solvents may be used alone, or a mixture thereof may be used as the solvent.

In the case of producing a silicon-containing thin film by the CVD method or the ALD method, the hydrosilane derivative (1') fed as a gas to the reaction chamber is decomposed, whereby a silicon-containing thin film can be produced on a substrate fixed in the reaction chamber. Examples of the method for decomposing the hydrosilane derivative (1') include a method by heat, a method using a plasma, light or the like, and a method where a reactant gas such as water, oxygen gas, ozone, hydrogen peroxide, hydrogen gas, ammonia, alcohols (e.g., methanol, ethanol, 2-propanol) and carboxylic acids (e.g., formic acid, acetic acid, propionic acid) is fed into the reaction chamber to cause a chemical reaction. These methods are used individually or in combination, whereby the hydrosilane derivative (1') can be decomposed and a silicon-containing thin film can be produced. The substrate temperature when decomposing the hydrosilane derivative (1') is appropriately selected according to the decomposition conditions. For example, in the case where a plasma or light is not used in combination and an oxygen gas is used as the reactant gas, the substrate temperature is not particularly limited and is, in view of cost advantage, preferably from 300 to 1,000° C., and in view of good deposition rate, more preferably from 400 to 750° C., still more preferably from 450 to 700° C. Also, by appropriately using a plasma, light, ozone, hydrogen peroxide, ammonia or the like, a silicon-containing thin film can be produced even in the temperature region of 300° C. or less. Furthermore, by using the hydrosilane derivative (1') of the present invention, a silicon-containing thin film such as silicon dioxide can be efficiently produced even at a low temperature of 500° C. or less without using a plasma or ozone.

The silicon-containing thin film produced using the hydrosilane derivative (1') as the material for thin film production has various electrical properties such as electrical conductivity, electrical insulation and dielectricity according to the composition and therefore, can be used not only as an electrode, an insulator or a dielectric material for a semiconductor device such as DRAM and flash memory but also, for example, as an optical material for a coating film or the like. Among others, a silicon dioxide thin film and a silicon nitride thin film can be used for an insulator, a dielectric material, a sacrificial layer, an anti-reflective film, a gas barrier film, a protective film, a hard mask or the like, and furthermore, the silicon nitride thin film can be used also for a diffusion barrier film, a durable coating or the like.

In addition, the hydrosilane derivative (1') is also useful as various silicon-containing polymers or silane coupling agents or as a synthetic intermediate thereof.

EXAMPLES

The present invention is described in greater detail below by referring to Examples, but the present invention is not limited thereto. In the description of the present invention, Me, Et, Pr, $^i$Pr, $^c$Pr, Bu, $^i$Bu, $^s$Bu, $^t$Bu, $^t$Pe, Cy and $^t$Oct stand for methyl group, ethyl group, propyl group, isopropyl group, cyclopropyl group, butyl group, isobutyl group, sec-butyl group, tert-butyl group, tert-pentyl group, cyclohexyl group and 1,1,3,3-tetramethylbutyl group (tert-octyl group), respectively.

Reference Example-1

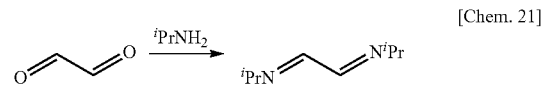

[Chem. 21]

6.06 g (41.8 mmol) of an aqueous 40% glyoxal solution was added to a mixed solution of 5.32 g (89.9 mmol) of isopropylamine and 50 mL of water, and the mixture was stirred at room temperature for 1 hour. The produced solid was separated by filtration, washed twice with 5 mL of water and then dried under reduced pressure to obtain N,N'-diisopropyl-1,4-diaza-1,3-butadiene ($^i$PrNCHCHN$^i$Pr) as a white solid (yielded amount: 4.66 g, yield: 80%).

$^1$H NMR (500 MHz, C$_6$D$_6$, δ/ppm) 7.94 (s, 2H), 3.15 (sept, J=6 Hz, 2H), 1.08 (d, J=6 Hz, 12H).

Reference Example-2

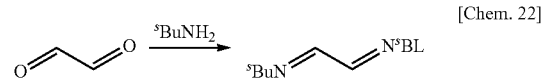

[Chem. 22]

84.45 g (582.0 mol) of an aqueous 40% glyoxal solution was added to a mixed solution of 86.07 g (1.177 mol) of sec-butylamine and 200 mL of hexane, and the mixture was stirred at room temperature for 30 minutes. Thereto, 15.00 g of sodium chloride was added and after further stirring for 15 minutes, the stirring was stopped to cause separation into two layers. The aqueous layer was removed and then, 5.00 g of magnesium sulfate was added to the hexane layer, followed by stirring at room temperature for 30 minutes. Insoluble matters were separated by filtration, and the filtrate was dried under reduced pressure to obtain N,N'-di-sec-butyl-1,4-diaza-1,3-butadiene ($^s$BuNCHCHN$^s$Bu) as a pale yellow liquid (yielded amount: 97.10 g, yield: 99%). This product was a mixture of a plurality of isomers differing in the steric configuration from each other.

$^1$H NMR (500 MHz, C$_6$D$_6$, δ/ppm) 7.98 (s, 2H), 2.88 (sext, J=6 Hz, 2H), 1.60-1.50 (m, 2H), 1.47-1.38 (m, 2H), 1.09 (d, J=6 Hz, 6H), 0.75 (d, J=7 Hz, 6H).

Reference Example-3

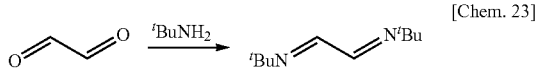
[Chem. 23]

A mixed solution of 50 mL of hexane and 20.48 g (280.0 mmol) of tert-butylamine was cooled by dipping it in an ice bath and after adding 20.30 g (139.9 mmol) of an aqueous 40% glyoxal solution, the mixture was stirred at room temperature for 1 hour. The aqueous layer was removed and then, 2.00 g of magnesium sulfate was added to the hexane layer, followed by stirring at room temperature for 30 minutes. Insoluble matters were separated by filtration, and the filtrate was dried under reduced pressure to obtain N,N'-di-tert-butyl-1,4-diaza-1,3-butadiene ($^t$BuNCHCHN$^t$Bu) as a white solid (yielded amount: 22.90 g, yield: 97%).

$^1$H NMR (500 MHz, C$_6$D$_6$, δ/ppm) 8.07 (s, 2H), 1.12 (s, 18H).

Reference Example-4

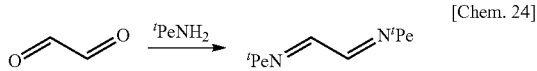
[Chem. 24]

A mixed solution of 160 mL of hexane and 118.4 g (1.358 mol) of tert-pentylamine was cooled by dipping it in an ice bath and after adding 98.04 g (675.7 mmol) of an aqueous 40% glyoxal solution, the mixture was stirred at room temperature for 1 hour. The aqueous layer was removed and then, 5.00 g of magnesium sulfate was added to the hexane layer, followed by stirring at room temperature for 30 minutes. Insoluble matters were separated by filtration, and the filtrate was dried under reduced pressure to obtain N,N'-di-tert-pentyl-1,4-diaza-1,3-butadiene ($^t$PeNCHCHN$^t$Pe) as a pale yellow liquid (yielded amount: 130.3 g, yield: 98%).

$^1$H NMR (500 MHz, C$_6$D$_6$, δ/ppm) 8.07 (s, 2H), 1.52 (q, J=7 Hz, 4H), 1.04 (s, 12H), 0.79 (t, j=7 Hz, 6H).

Reference Example-5

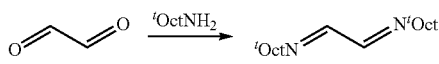
[Chem. 25]

10.66 g (73.5 mmol) of an aqueous 40% glyoxal solution was added to a mixed solution of 19.50 g (150.9 mmol) of 1,1,3,3-tetramethylbutylamine and 100 mL of water, and the mixture was stirred at room temperature for 1 hour. The produced solid was separated by filtration, washed twice with 10 mL of water and then dried under reduced pressure to obtain N,N'-bis(1,1,3,3-tetramethylbutyl)-1,4-diaza-1,3-butadiene ($^t$OctNCHCHN$^t$Oct) as a white solid (yielded amount: 19.54 g, yield: 95%).

$^1$H NMR (500 MHz, C$_6$D$_6$, δ/ppm) 8.09 (s, 2H), 1.61 (s, 4H), 1.14 (s, 12H), 0.98 (s, 18H).

Reference Example-6

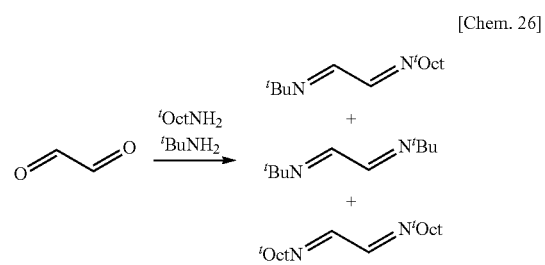
[Chem. 26]

A mixed solution of 66.00 g (510.7 mmol) of 1,1,3,3-tetramethylbutylamine and 37.35 g (510.7 mmol) of tert-butylamine was added to a mixed solution of 200 mL of hexane and 74.10 g (510.7 mmol) of an aqueous 40% glyoxal solution, and the mixture was stirred at room temperature for 1 hour. The aqueous layer was removed and then, 5.00 g of magnesium sulfate was added to the hexane layer, followed by stirring at room temperature for 30 minutes. Insoluble matters were separated by filtration, and the filtrate was dried under reduced pressure to obtain a mixture of N-tert-butyl-N'-1,1,3,3-tetramethylbutyl-1,4-diaza-1,3-butadiene ($^t$BuNCHCHN$^t$Oct), $^t$BuNCHCHN$^t$Bu and $^t$OctNCHCHN$^t$Oct as a pale yellow liquid (yielded amount: 111.4 g, yield: 97%).

$^1$H NMR (500 MHz, C$_6$D$_6$, δ/ppm) 8.094 (s), 8.091 (d, J=8 Hz), 8.08 (d, J=8 Hz), 8.07 (s), 1.61 (s), 1.60 (s), 1.14 (s), 1.12 (s), 1.11 (s), 0.979 (s), 0.976 (s).

$^{13}$C NMR (125 MHz, C$_6$D$_6$, δ/ppm) 157.80, 157.79, 157.76, 61.97, 58.10, 56.63, 56.56, 32.51, 32.47, 32.19, 32.18, 29.774, 29.69, 29.66, 29.61.

Reference Example-7

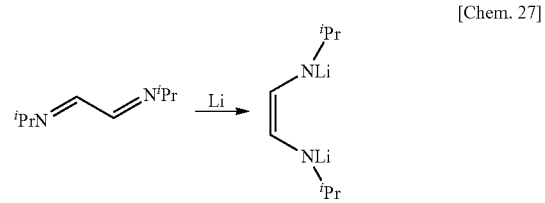
[Chem. 27]

In an argon atmosphere, 26.27 g (187.3 mmol) of $^i$PrNCHCHN$^i$Pr was dissolved in 190 mL of tetrahydrofuran and after adding 2.67 g (385 mmol) of lithium, the mixture was stirred at room temperature for 7 hours to obtain a dilithium(N,N'-diisopropyl-1,2-vinylenediaminide) solution as a dark red uniform solution.

Reference Example-8

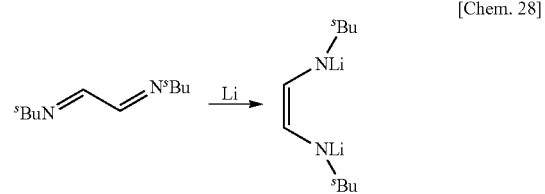
[Chem. 28]

In an argon atmosphere, 31.24 g (185.6 mmol) of
$^s$BuNCHCHN$^s$Bu was dissolved in a mixed solvent of 50 mL
of tetrahydrofuran and 200 mL of hexane and after adding
2.71 g (390 mmol) of lithium, the mixture was stirred at room
temperature for 12 hours to obtain a dilithium(N,N'-di-sec-
butyl-1,2-vinylenediaminide) solution as a dark red uniform
solution.

Reference Example-9

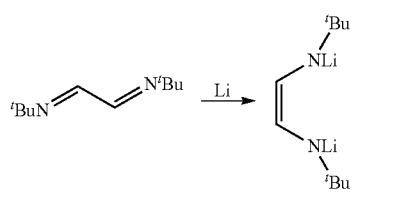
[Chem. 29]

In an argon atmosphere, 32.00 g (190.2 mmol) of
$^t$BuNCHCHN$^t$Bu was dissolved in a mixed solvent of 50 mL
of tetrahydrofuran and 150 mL of hexane and after adding
2.66 g (383 mmol) of lithium, the mixture was stirred at room
temperature for 16 hours to obtain a dilithium(N,N'-di-tert-
butyl-1,2-vinylenediaminide) solution as a dark red uniform
solution.

Reference Example-10

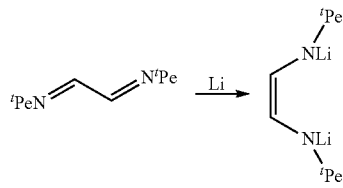
[Chem. 30]

In an argon atmosphere, 36.55 g (186.2 mmol) of
$^t$PeNCHCHN$^t$Pe was dissolved in a mixed solvent of 50 mL
of tetrahydrofuran and 190 mL of hexane and after adding
2.66 g (383 mmol) of lithium, the mixture was stirred at room
temperature for 14 hours to obtain a dilithium(N,N'-di-tert-
pentyl-1,2-vinylenediaminide) solution as a dark red uniform
solution.

Reference Example-11

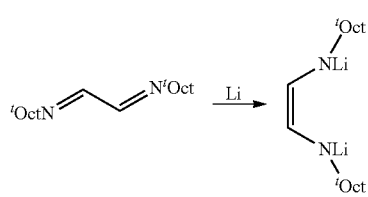
[Chem. 31]

In an argon atmosphere, 52.28 g (186.4 mmol) of $^t$Oct-
NCHCHN$^t$Oct was dissolved in a mixed solvent of 30 mL of
tetrahydrofuran and 200 mL of hexane and after adding 2.68
g (386 mmol) of lithium, the mixture was stirred at room
temperature for 16 hours to obtain a dilithium(N,N'-di(1,1,3,
3-tetramethylbutyl)-1,2-vinylenediaminide) solution as a
dark red uniform solution.

Reference Example-12

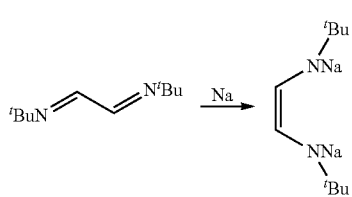
[Chem. 32]

In an argon atmosphere, 27.90 g (165.8 mmol) of
$^t$BuNCHCHN$^t$Bu was dissolved in 180 mL of tetrahydrofu-
ran and after adding 7.59 g (330 mmol) of sodium, the mix-
ture was stirred at room temperature for 12 hours to obtain a
disodium(N,N'-di-tert-butyl-1,2-vinylenediaminide) solu-
tion as a dark red uniform solution.

Reference Example-13

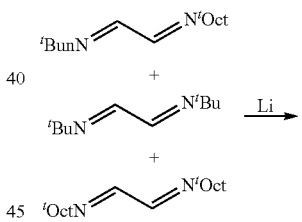
[Chem. 33]

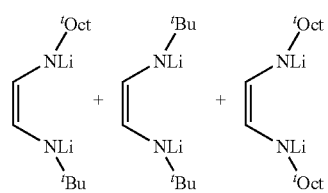

In an argon atmosphere, 41.60 g of a mixture of
$^t$BuNCHCHN$^t$Oct, $^t$BuNCHCHN$^t$Bu and $^t$OctNCHCHN$^t$Oct
obtained by the method described in Reference Example-6
was dissolved in a mixed solvent of 50 mL of tetrahydrofuran
and 150 mL of hexane and after adding 2.67 g (393 mmol) of
lithium, the mixture was stirred at room temperature for 12
hours to obtain a mixed solution of dilithium(N-tert-butyl-N'-
1,1,3,3-tetramethylbutyl-1,2-vinylenediaminide), dilithium
(N,N'-di-tert-butyl-1,2-vinylenediaminide) and dilithium(N,
N'-di(1,1,3,3-tetramethylbutyl)-1,2-vinylenediaminide) as a
dark red uniform solution.

Reference Example-14

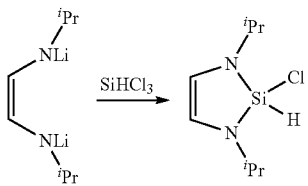

[Chem. 34]

In an argon atmosphere, a dilithium(N,N'-diisopropyl-1,2-vinylenediaminide) solution prepared according to the procedure and reagent quantities described in Reference Example-7 was added to a hexane (200 mL) solution containing 25.00 g (184.6 mmol) of trichlorosilane, and the mixture was stirred at room temperature for 16 hours. Insoluble matters produced were separated by filtration, and the solvent was removed by distillation from the filtrate under atmospheric pressure. The obtained oily material was distilled under reduced pressure (distillation temperature: 64° C./4.4×$10^2$ Pa) to obtain 2-chloro-1,3-diisopropyl-1,3-diaza-2-silacyclopent-4-ene (Si($^i$PrNCHCHN$^i$Pr)(H)Cl) as a colorless liquid (yielded amount: 12.96 g, yield: 34%).

$^1$H NMR (500 MHz, $C_6D_6$, δ/ppm) 6.36 (s, 1H), 5.59 (s, 2H), 3.20 (m, 2H), 1.13 (d, J=7 Hz, 6H), 1.10 (d, J=7 Hz, 6H).

$^{13}$C NMR (125 MHz, $C_6D_6$, δ/ppm) 115.3, 48.3, 24.7, 24.0.

Reference Example-15

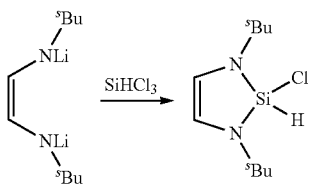

[Chem. 35]

In an argon atmosphere, a dilithium(N,N'-di-sec-butyl-1,2-vinylenediaminide) solution prepared according to the procedure and reagent quantities described in Reference Example-8 was added to a hexane (150 mL) solution containing 25.00 g (184.6 mmol) of trichlorosilane, and the mixture was stirred at room temperature for 6 hours. Insoluble matters produced were separated by filtration, and the solvent was removed by distillation from the filtrate under atmospheric pressure. The obtained residue was distilled under reduced pressure (distillation temperature: 85° C./5×$10^2$ Pa) to obtain 2-chloro-1,3-di-sec-butyl-1,3-diaza-2-silacyclopent-4-ene (Si($^s$BuNCHCHN$^s$Bu)(H)Cl) as a pale yellow liquid (yielded amount: 18.10 g, yield: 42%). This product was a mixture of a plurality of isomers differing in the steric configuration from each other.

$^1$H NMR (500 MHz, $C_6D_6$, δ/ppm) 6.39 (s, 1H), 5.61 (m)/5.58 (m) (2H as the total of integrated intensities of two signals), 2.95 (m, 2H), 1.63-1.49 (m, 2H), 1.42-1.29 (m, 2H), 1.14 (d, J=7 Hz)/1.12 (d, J=7 Hz) (6H as the total of integrated intensities of two signals), 0.80 (t, J=7 Hz)/0.78 (t, J=7 Hz) (6H as the total of integrated intensities of two signals).

$^{13}$C NMR (125 MHz, $C_6D_6$, δ/ppm) 115.4, 115.3, 114.7, 114.5, 54.4, 54.0, 31.38, 31.36, 30.82, 30.81, 22.51, 22.49, 21.6, 11.4, 11.3.

Reference Example-16

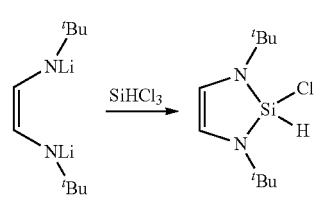

[Chem. 36]

In an argon atmosphere, a dilithium(N,N'-di-tert-butyl-1,2-vinylenediaminide) solution prepared according to the procedure and reagent quantities described in Reference Example-9 was added to a hexane (50 mL) solution containing 25.20 g (186.0 mmol) of trichlorosilane, and the mixture was stirred at room temperature for 3 hours. Insoluble matters produced were separated by filtration, and the solvent was removed by distillation from the filtrate under atmospheric pressure. The obtained residue was distilled under reduced pressure (distillation temperature: 80° C./3.8×$10^2$ Pa) to obtain 2-chloro-1,3-di-tert-butyl-1,3-diaza-2-silacyclopent-4-ene (Si($^t$BuNCHCHN$^t$Bu)(H)Cl) as a colorless liquid (yielded amount: 35.58 g, yield: 83%).

$^1$H NMR (500 MHz, $C_6D_6$, δ/ppm) 6.40 (s, 1H), 5.77 (s, 2H), 1.21 (s, 18H).

$^{13}$C NMR (125 MHz, $C_6D_6$, δ/ppm) 113.1, 51.9, 30.8.

Reference Example-17

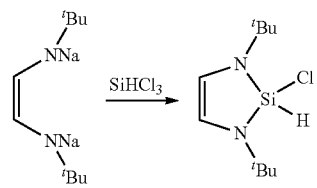

[Chem. 37]

In an argon atmosphere, a disodium(N,N'-di-tert-butyl-1,2-vinylenediaminide) solution prepared according to the procedure and reagent quantities described in Reference Example-12 was added to a hexane (50 mL) solution containing 25.20 g (186.0 mmol) of trichlorosilane, and the mixture was stirred at room temperature for 3 hours. Insoluble matters produced were separated by filtration, and the solvent was removed by distillation from the filtrate under atmospheric pressure. The obtained residue was distilled under reduced pressure (distillation temperature: 80° C./3.8×$10^2$ Pa) to obtain Si($^t$BuNCHCHN$^t$Bu)(H)Cl) as a colorless liquid (yielded amount: 20.80 g, yield: 48%). The thus-obtained Si($^t$BuNCHCHN$^t$Bu)(H)Cl was measured for the $^1$H and $^{13}$C NMR spectra, as a result, these spectra agreed with spectra of that obtained in Reference Example-16.

Reference Example-18

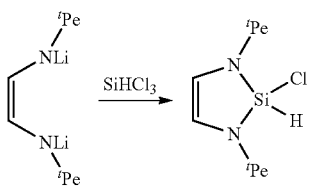

[Chem. 38]

In an argon atmosphere, a dilithium(N,N'-di-tert-pentyl-1,2-vinylenediaminide) solution prepared according to the procedure and reagent quantities described in Reference Example-10 was added to a hexane (180 mL) solution containing 25.00 g (184.6 mmol) of trichlorosilane, and the mixture was stirred at room temperature for 4 hours. Insoluble matters produced were separated by filtration, and the solvent was removed by distillation from the filtrate under atmospheric pressure. The obtained residue was distilled under reduced pressure (distillation temperature: 95° C./3.8×10$^2$ Pa) to obtain 2-chloro-1,3-di-tert-pentyl-1,3-diaza-2-silacyclopent-4-ene Si($^t$PeNCHCHN$^t$Pe)(H)Cl) as a colorless liquid (yielded amount: 44.11 g, yield: 92%).

$^1$H NMR (500 MHz, C$_6$D$_6$, δ/ppm) 6.45 (s, 1H), 5.71 (s, 2H), 1.47 (dq, J=16 Hz, 8 Hz, 2H), 1.41 (dq, J=16 Hz, 8 Hz, 2H), 1.199 (s, 6H), 1.197 (s, 6H), 0.78 (t, J=8 Hz, 6H).

$^{13}$C NMR (125 MHz, C$_6$D$_6$, δ/ppm) 112.9, 54.6, 35.2, 28.7, 28.2, 8.9.

Reference Example-19

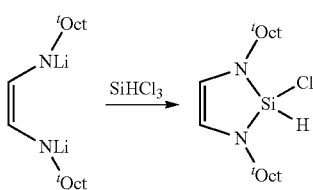

[Chem. 39]

In an argon atmosphere, a dilithium(N,N'-bis(1,1,3,3-tetramethylbutyl)-1,2-vinylenediaminide) solution prepared according to the procedure and reagent quantities described in Reference Example-11 was added to a hexane (150 mL) solution containing 25.00 g (184.6 mmol) of trichlorosilane, and the mixture was stirred at room temperature for 3 hours. Insoluble matters produced were separated by filtration, and the solvent was removed by distillation from the filtrate under atmospheric pressure. The obtained residue was distilled under reduced pressure (distillation temperature: 125° C./85 Pa) to obtain 2-chloro-1,3-bis(1,1,3,3-tetramethylbutyl)-1,3-diaza-2-silacyclopent-4-ene (Si($^t$OctNCHCHN$^t$Oct)(H)Cl) as a pale yellow liquid (yielded amount: 57.22 g, yield: 90%).

$^1$H NMR (500 MHz, C$_6$D$_6$, δ/ppm) 6.44 (s, 1H), 5.73 (s, 2H), 1.60 (d, J=15 Hz, 2H), 1.43 (s, 6H), 1.31 (d, J=15 Hz, 2H), 1.28 (s, 6H), 0.95 (s, 18H).

$^{13}$C NMR (125 MHz, C$_6$D$_6$, δ/ppm) 113.0, 55.7, 53.8, 32.7, 32.0, 31.8, 30.0.

Reference Example-20

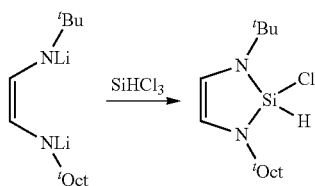

[Chem. 40]

In an argon atmosphere, a mixed solution of dilithium(N-tert-butyl-N'-1,1,3,3-tetramethylbutyl-1,2-vinylenediaminide), dilithium(N,N'-di-tert-butyl-1,2-vinylenediaminide) and dilithium(N,N'-di(1,1,3,3-tetramethylbutyl)-1,2-vinylenediaminide prepared according to the procedure and reagent quantities described in Reference Example-13 was added to a hexane (100 mL) solution containing 25.14 g (185.6 mmol) of trichlorosilane, and the mixture was stirred at room temperature for 3 hours. Insoluble matters produced were separated by filtration, and the solvent was removed by distillation from the filtrate under atmospheric pressure. The obtained residue was distilled under reduced pressure, and the fraction at a distillation temperature of 83° C./81 Pa was separated to obtain 2-chloro-3-tert-butyl-1-1,1,3,3-tetramethylbutyl-1,3-diaza-2-silacyclopent-4-ene (Si($^t$BuNCHCHN$^t$Oct)(H)Cl) as a pale yellow liquid (yielded amount: 9.84 g, yield: 18%).

$^1$H NMR (500 MHz, C$_6$D$_6$, δ/ppm) 6.44 (t, J=1 Hz, 1H), 5.77 (dd, J=4 Hz, 1 Hz, 1H), 5.72 (dd, J=4 Hz, 1 Hz, 1H), 1.59 (d, J=15 Hz, 1H), 1.41 (s, 3H), 1.35 (d, J=15 Hz, 2H), 1.28 (s, 3H), 1.21 (s, 9H), 0.95 (s, 9H).

$^{13}$C NMR (125 MHz, C$_6$D$_6$, δ/ppm) 113.4, 112.8, 55.7, 54.1, 51.9, 32.4, 32.0, 31.8, 30.8, 30.1.

Example-1

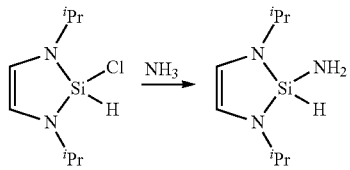

[Chem. 41]

In an argon atmosphere, 4.06 g (19.8 mmol) of Si($^i$PrNCHCHN$^i$Pr)(H)Cl was dissolved in 20 mL of hexane. The resulting solution was deaerated by Freeze-Pump-Thaw cycling and after creating an ammonia atmosphere in the reaction vessel by connecting thereto a balloon having an internal volume of 5 L and being filled with ammonia, the solution was stirred at room temperature for 3 hours. Insoluble matters produced were separated by filtration, and the solvent was removed by distillation from the filtrate under atmospheric pressure. The obtained residue was distilled under reduced pressure (distillation temperature: 80° C./8.8× 10$^2$ Pa) to obtain 2-amino-1,3-diisopropyl-1,3-diaza-2-silacyclopent-4-ene (Si($^i$PrNCHCHN$^i$Pr)(H)NH$_2$) as a colorless liquid (yielded amount: 2.11 g, yield: 58%).

$^1$H NMR (500 MHz, C$_6$D$_6$, δ/ppm) 5.66 (m, 2H), 5.62 (t, J=5 Hz, 1H), 3.35 (sept, J=7 Hz, 2H), 1.20 (d, J=7 Hz, 6H), 1.18 (d, J=7 Hz, 6H), 0.84 (br, 2H).
$^{13}$C NMR (125 MHz, C$_6$D$_6$, δ/ppm) 114.0, 48.0, 25.3, 24.3.

Example-2

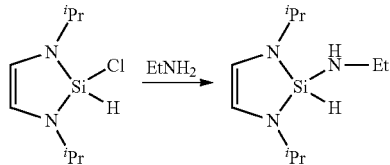

[Chem. 42]

In an argon atmosphere, 6.80 g (151 mmol) of ethylamine was dissolved in 20 mL of hexane, and a solution obtained by dissolving 5.73 g (28.0 mmol) of Si($^i$PrNCHCHN$^i$Pr)(H)Cl in 5 mL of hexane was added thereto at −20° C. After stirring at room temperature for 4 hours, insoluble matters produced were separated by filtration, and the solvent was removed by distillation from the filtrate under atmospheric pressure. The obtained residue was distilled under reduced pressure (distillation temperature: 74° C./4.3×10$^2$ Pa) to obtain 2-ethylamino-1,3-di-isopropyl-1,3-diaza-2-silacyclopent-4-ene (Si($^i$PrNCHCHN$^i$Pr)(H)NHEt) as a colorless liquid (yielded amount: 5.34 g, yield: 89%).

$^1$H NMR (500 MHz, C$_6$D$_6$, δ/ppm) 5.68 (s, 2H), 5.58 (s, 1H), 3.35 (sept, J=7 Hz, 2H), 2.70 (quint, J=7 Hz, 2H), 1.21 (d, J=7 Hz, 6H), 1.19 (d, J=7 Hz, 6H), 0.94 (br, 1H), 0.91 (t, J=7 Hz, 3H).
$^{13}$C NMR (125 MHz, C$_6$D$_6$, δ/ppm) 114.0, 47.9, 35.1, 25.0, 24.2, 20.1.

Example-3

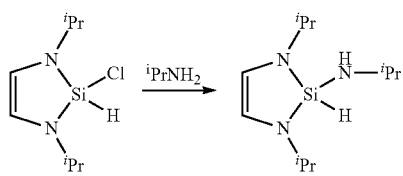

[Chem. 43]

In an argon atmosphere, 4.24 g (20.7 mmol) of Si($^i$PrNCHCHN$^i$Pr)(H)Cl was dissolved in 20 mL of hexane and after adding 2.51 g (42.4 mmol) of isopropylamine, the mixture was stirred at room temperature for 3 hours. Insoluble matters produced were separated by filtration, and the solvent was removed by distillation from the filtrate under atmospheric pressure. The obtained residue was distilled under reduced pressure (distillation temperature: 75° C./3.7×10$^2$ Pa) to obtain 1,3-diisopropyl-2-isopropylamino-1,3-diaza-2-silacyclopent-4-ene (Si($^i$PrNCHCHN$^i$Pr)(H)NH$^i$Pr) as a colorless liquid (yielded amount: 4.10 g, yield: 87%).

$^1$H NMR (500 MHz, C$_6$D$_6$, δ/ppm) 5.69 (s, 2H), 5.58 (s, 1H), 3.37 (sept, J=7 Hz, 2H), 3.18 (m, 1H), 1.21 (d, J=7 Hz, 12H), 0.94 (br, 1H), 0.96 (d, J=7 Hz, 6H).

$^{13}$C NMR (125 MHz, C$_6$D$_6$, δ/ppm) 113.6, 47.6, 42.2, 27.6, 25.0, 24.1.

Example-4

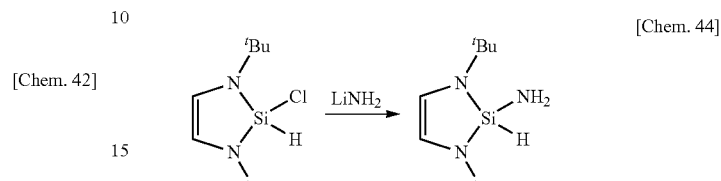

[Chem. 44]

In an argon atmosphere, 505 mg (purity: 95%, 20.9 mmol) of lithium amide was suspended in 20 mL of 1,2-dimethoxyethane and after adding 4.65 g (20.0 mmol) of Si($^t$BuNCHCHN$^t$Bu)(H)Cl, the mixture was stirred at room temperature for 2 hours. Subsequently, 20 mL of hexane was added to the reaction mixture, and the mixture was stirred at room temperature for 10 minutes. Insoluble matters produced were separated by filtration, and the solvent was removed by distillation from the filtrate under atmospheric pressure. The obtained residue was distilled under reduced pressure (distillation temperature: 78° C./3.8×10$^2$ Pa) to obtain 2-amino-1,3-di-tert-butyl-1,3-diaza-2-silacyclopent-4-ene (Si($^t$BuNCHCHN$^t$Bu)(H)NH$_2$) as a pale yellow liquid (yielded amount: 3.93 g, yield: 92%).

$^1$H NMR (500 MHz, C$_6$D$_6$, δ/ppm) 5.81 (d, J=1 Hz, 2H), 5.68 (t, J=5 Hz, 1H), 1.29 (s, 18H), 0.83 (br, 2H).
$^{13}$C NMR (125 MHz, C$_6$D$_6$, δ/ppm) 111.9, 51.4, 31.4.

Example-5

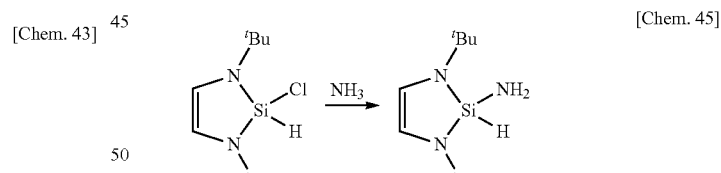

[Chem. 45]

In an argon atmosphere, 6.44 g (27.7 mmol) of Si($^t$BuNCHCHN$^t$Bu)(H)Cl was dissolved in 20 mL of hexane. The resulting solution was deaerated by Freeze-Pump-Thaw cycling and after creating an ammonia atmosphere in the reaction vessel by connecting thereto a balloon having an internal volume of 5 L and being filled with ammonia, the solution was stirred at room temperature for 3 hours. Insoluble matters produced were separated by filtration, and the solvent was removed by distillation from the filtrate under atmospheric pressure. The obtained residue was distilled under reduced pressure (distillation temperature: 78° C./3.7×10$^2$ Pa) to obtain Si($^t$BuNCHCHN$^t$Bu)(H)NH$_2$ as a pale yellow liquid (yielded amount: 5.45 g, yield: 92%). The thus-obtained Si($^t$BuNCHCHN$^t$Bu)(H)NH$_2$ was measured for the $^1$H and $^{13}$C NMR spectra, as a result, these spectra agreed with spectra of that obtained in Example-4.

Example-6

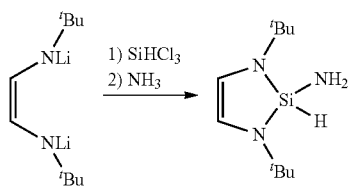

[Chem. 46]

In an argon atmosphere, a dilithium(N,N'-di-tert-butyl-1,2-vinylenediaminide) solution prepared by using 12.65 g of $^t$BuNCHCHN$^t$Bu, 20 mL of tetrahydrofuran, 60 mL of hexane and 1.05 g of lithium according to the procedure described in Reference Example-9 was added to a hexane (20 mL) solution containing 9.98 g (73.7 mmol) of trichlorosilane, and the mixture was stirred at room temperature for 3 hours. The resulting reaction mixture was deaerated by Freeze-Pump-Thaw cycling and after creating an ammonia atmosphere in the reaction vessel by connecting thereto a balloon having an internal volume of 5 L and being filled with ammonia, the mixture was stirred at room temperature for 20 hours. Insoluble matters produced were separated by filtration, and the solvent was removed by distillation from the filtrate under atmospheric pressure. The obtained residue was distilled under reduced pressure (distillation temperature: 78° C./3.7×10$^2$ Pa) to obtain Si($^t$BuNCHCHN$^t$Bu)(H)NH$_2$ as a pale yellow liquid (yielded amount: 14.09 g, yield: 90%). The thus-obtained Si($^t$BuNCHCHN$^t$Bu)(H)NH$_2$ was measured for the $^1$H and $^{13}$C NMR spectra, as a result, these spectra agreed with spectra of those obtained in Example-4 and Example-5.

Example-7

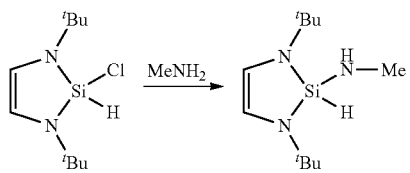

[Chem. 47]

In an argon atmosphere, 5.24 g (22.5 mmol) of Si($^t$BuNCHCHN$^t$Bu)(H)Cl was dissolved in 20 mL of hexane and after adding 25.0 mL (48.8 mmol) of a tetrahydrofuran solution (concentration: 1.95 mol/L) of methylamine, the mixture was stirred at room temperature for 1 hour. Insoluble matters produced were separated by filtration, and the solvent was removed by distillation from the filtrate under atmospheric pressure. The obtained residue was distilled under reduced pressure (distillation temperature: 80° C./3.8×10$^2$ Pa) to obtain 1,3-di-tert-butyl-2-methylamino-1,3-diaza-2-silacyclopent-4-ene (Si($^t$BuNCHCHN$^t$Bu)(H)NHMe) as a pale yellow liquid (yielded amount: 4.41 g, yield: 86%).

$^1$H NMR (500 MHz, C$_6$D$_6$, δ/ppm) 5.81 (d, J=1 Hz, 2H), 5.60 (s, 1H), 2.31 (d, J=7 Hz, 3H), 1.28 (s, 18H), 0.65 (br, 1H).

$^{13}$C NMR (125 MHz, C$_6$D$_6$, δ/ppm) 112.0, 51.3, 31.2, 26.4.

Example-8

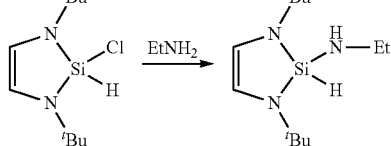

[Chem. 48]

In an argon atmosphere, 3.40 g (75.5 mmol) of ethylamine was dissolved in 30 mL of hexane, and a solution obtained by dissolving 5.78 g (24.8 mmol) of Si($^t$BuNCHCHN$^t$Bu)(H)Cl in 5 mL of hexane was added thereto at −20° C. After stirring at room temperature for 2 hours, insoluble matters produced were separated by filtration, and the solvent was removed by distillation from the filtrate under atmospheric pressure. The obtained residue was distilled under reduced pressure (distillation temperature: 86° C./4.1×10$^2$ Pa) to obtain 1,3-di-tert-butyl-2-ethylamino-1,3-diaza-2-silacyclopent-4-ene (Si($^t$BuNCHCHN$^t$Bu)(H)NHEt) as a pale yellow liquid (yielded amount: 5.77 g, yield: 96%).

$^1$H NMR (500 MHz, C$_6$D$_6$, δ/ppm) 5.83 (s, 2H), 5.65 (s, 1H), 2.69 (quint, J=7 Hz, 2H), 1.30 (s, 18H), 0.92 (t, J=7 Hz, 3H), 0.82 (br, 1H).

$^{13}$C NMR (125 MHz, C$_6$D$_6$, δ/ppm) 112.0, 51.3, 35.1, 31.3, 19.9.

Example-9

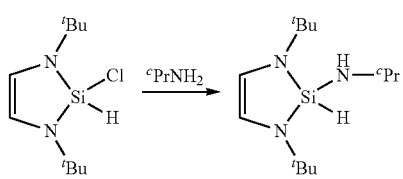

[Chem. 49]

In an argon atmosphere, 6.22 g (26.7 mmol) of Si($^t$BuNCHCHN$^t$Bu)(H)Cl was dissolved in 30 mL of hexane and after adding 3.14 g (56.0 mmol) of cyclopropylamine, the mixture was stirred at room temperature for 3 hours. Insoluble matters produced were separated by filtration, and the solvent was removed by distillation from the filtrate under atmospheric pressure. The obtained residue was distilled under reduced pressure (distillation temperature: 100° C./3.7×10$^2$ Pa) to obtain 1,3-di-tert-butyl-2-cyclopropylamino-1,3-diaza-2-silacyclopent-4-ene (Si($^t$BuNCHCHN$^t$Bu)(H)NH$^c$Pr) as a colorless liquid (yielded amount: 6.07 g, yield: 90%).

$^1$H NMR (500 MHz, C$_6$D$_6$, δ/ppm) 5.80 (s, 2H), 5.34 (s, 1H), 2.08 (m, 1H), 1.28 (s, 18H), 0.90 (br, 1H), 0.39-0.29 (m, 4H).

$^{13}$C NMR (125 MHz, C$_6$D$_6$, δ/ppm) 113.8, 51.4, 31.2, 23.8, 7.9.

Example-10

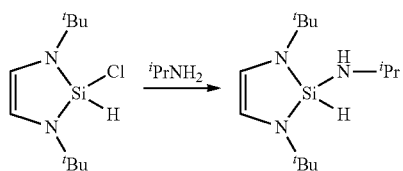

[Chem. 50]

In an argon atmosphere, 5.70 g (24.5 mmol) of Si($^t$BuNCHCHN$^t$Bu)(H)Cl was dissolved in 40 mL of hexane and after adding 2.90 g (49.1 mmol) of isopropylamine, the mixture was stirred at room temperature for 5 hours. Insoluble matters produced were separated by filtration, and the solvent was removed by distillation from the filtrate under atmospheric pressure. The obtained residue was distilled under reduced pressure (distillation temperature: 90° C./3.7× 10$^2$ Pa) to obtain 1,3-di-tert-butyl-2-isopropylamino-1,3-diaza-2-silacyclopent-4-ene (Si($^t$BuNCHCHN$^t$Bu)(H)NH$^i$Pr) as a pale yellow liquid (yielded amount: 5.65 g, yield: 90%).

$^1$H NMR (500 MHz, C$_6$D$_6$, δ/ppm) 5.80 (s, 2H), 5.64 (s, 1H), 3.20 (double septet, J=8 Hz, 7 Hz, 1H), 1.31 (s, 18H), 0.98 (d, J=7 Hz, 6H), 0.87 (br, d, J=8 Hz, 1H).

$^{13}$C NMR (125 MHz, C$_6$D$_6$, δ/ppm) 111.9, 51.4, 42.3, 31.3, 27.5.

Example-11

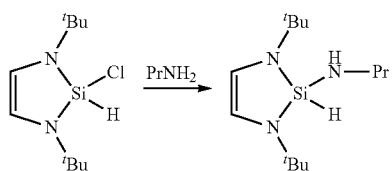

[Chem. 51]

In an argon atmosphere, 5.90 g (25.4 mmol) of Si($^t$BuNCHCHN$^t$Bu)(H)Cl was dissolved in 40 mL of hexane and after adding 3.03 g (51.3 mmol) of propylamine, the mixture was stirred at room temperature for 3 hours. Insoluble matters produced were separated by filtration, and the solvent was removed by distillation from the filtrate under atmospheric pressure. The obtained residue was distilled under reduced pressure (distillation temperature: 92° C./3.5× 10$^2$ Pa) to obtain 1,3-di-tert-butyl-2-propylamino-1,3-diaza-2-silacyclopent-4-ene (Si($^t$BuNCHCHN$^t$Bu)(H)NHPr) as a pale yellow liquid (yielded amount: 5.99 g, yield: 92%).

$^1$H NMR (500 MHz, C$_6$D$_6$, δ/ppm) 5.83 (d, J=1 Hz, 2H), 5.67 (s, 1H), 2.65 (q, J=7 Hz, 2H), 1.31 (s, 18H), 1.30 (sext, J=7 Hz, 2H), 0.94 (br, 1H), 0.75 (t, J=7 Hz, 3H).

$^{13}$C NMR (125 MHz, C$_6$D$_6$, δ/ppm) 112.0, 51.4, 42.6, 31.3, 27.7, 11.9.

Example-12

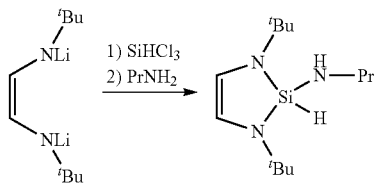

[Chem. 52]

In an argon atmosphere, a dilithium(N,N'-di-tert-butyl-1,2-vinylenediaminide) solution prepared by using 32.00 g of $^t$BuNCHCHN$^t$Bu, 50 mL of tetrahydrofuran, 150 mL of hexane and 2.67 g of lithium according to the procedure described in Reference Example-9 was added to a hexane (50 mL) solution containing 25.16 g (185.7 mmol) of trichlorosilane, and the mixture was stirred at room temperature for 3 hours. To this reaction mixture, 22.40 g (379.0 mmol) of propylamine was added, and the mixture was stirred at room temperature for 3 hours. Insoluble matters produced were separated by filtration, and the solvent was removed by distillation from the filtrate under atmospheric pressure. The obtained residue was distilled under reduced pressure (distillation temperature: 78° C./3.7×10$^2$ Pa) to obtain Si($^t$BuNCHCHN$^t$Bu)(H)NHPr as a pale yellow liquid (yielded amount: 41.46 g, yield: 87%). The thus-obtained Si($^t$BuNCHCHN$^t$Bu)(H)NHPr was measured for the $^1$H and $^{13}$C NMR spectra, as a result, these spectra agreed with spectra of that obtained in Example-11.

Example-13

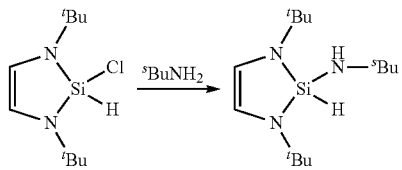

[Chem. 53]

In an argon atmosphere, 5.23 g (22.4 mmol) of Si($^t$BuNCHCHN$^t$Bu)(H)Cl was dissolved in 30 mL of hexane and after adding 3.30 g (45.1 mmol) of sec-butylamine, the mixture was stirred at room temperature for 14 hours. Insoluble matters produced were separated by filtration, and the solvent was removed by distillation from the filtrate under atmospheric pressure. The obtained residue was distilled under reduced pressure (distillation temperature: 98° C./3.5× 10$^2$ Pa) to obtain 2-sec-butylamino-1,3-di-tert-butyl-1,3-diaza-2-silacyclopent-4-ene (Si($^t$BuNCHCHN$^t$Bu)(H)NH$^s$Bu) as a pale yellow liquid (yielded amount: 5.56 g, yield: 92%).

$^1$H NMR (500 MHz, C$_6$D$_6$, δ/ppm) 5.83 (s, 2H), 5.69 (s, 1H), 3.02 (sept, J=7 Hz, 1H), 1.45-1.35 (m, 2H), 1.32 (s, 18H), 1.00 (d, J=6 Hz, 3H), 0.98 (br, 1H), 0.77 (t, J=7 Hz, 3H).

$^{13}$C NMR (125 MHz, C$_6$D$_6$, δ/ppm) 112.01, 112.00, 51.46, 51.43, 47.7, 31.3, 31.2, 23.8, 10.6.

Example-14

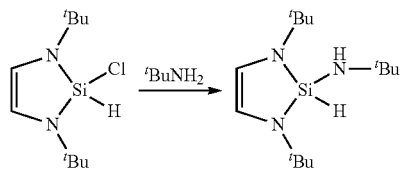

[Chem. 54]

In an argon atmosphere, 4.87 g (20.9 mmol) of Si($^t$BuNCHCHN$^t$Bu)(H)Cl was dissolved in 40 mL of hexane and after adding 3.13 g (42.8 mmol) of tert-butylamine, the mixture was stirred at room temperature for 14 hours. Insoluble matters produced were separated by filtration, and the solvent was removed by distillation from the filtrate under atmospheric pressure. The obtained residue was sublimated (heating temperature: 150° C./1.2×10$^2$ Pa) to obtain 2-tert-butyl amino-1,3-di-tert-butyl-1,3-diaza-2-silacyclopent-4-ene (Si($^t$BuNCHCHN$^t$Bu)(H)NH$^t$Bu) as a white solid (yielded amount: 5.06 g, yield: 90%).

$^1$H NMR (500 MHz, C$_6$D$_6$, δ/ppm) 5.79 (s, 2H), 5.56 (s, 1H), 1.33 (s, 18H), 1.14 (s, 9H), 1.01 (br, 1H).

$^{13}$C NMR (125 MHz, C$_6$D$_6$, δ/ppm) 111.7, 51.6, 49.5, 33.4, 31.2.

Example-15

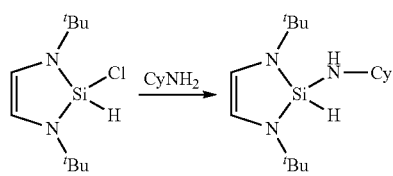

[Chem. 55]

In an argon atmosphere, 5.70 g (24.5 mmol) of Si($^t$BuNCHCHN$^t$Bu)(H)Cl was dissolved in 100 mL of hexane and after adding 4.86 g (49.0 mmol) of cyclohexylamine, the mixture was stirred at room temperature for 4 hours. Insoluble matters produced were separated by filtration, and the solvent was removed by distillation from the filtrate under atmospheric pressure. The obtained residue was sublimated (heating temperature: 160° C./7.0×10$^2$ Pa) to obtain 2-cyclohexylamino-1,3-di-tert-butyl-1,3-diaza-2-silacyclopent-4-ene (Si($^t$BuNCHCHN$^t$Bu)(H)NHCy) as a white solid (yielded amount: 6.95 g, yield: 96%).

$^1$H NMR (500 MHz, C$_6$D$_6$, δ/ppm) 5.83 (d, J=1 Hz, 2H), 5.71 (s, 1H), 2.87 (m, 1H), 1.86 (m, 2H), 1.57 (m, 2H), 1.44 (m, 1H), 1.33 (s, 18H), 1.20-0.95 (m, 6H).

$^{13}$C NMR (125 MHz, C$_6$D$_6$, δ/ppm) 112.0, 51.5, 49.8, 38.4, 31.3, 26.4, 26.0.

Example-16

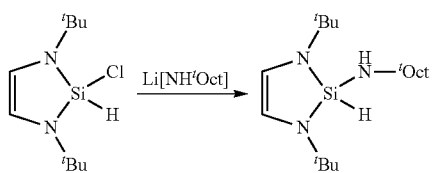

[Chem. 56]

In an argon atmosphere, a solution obtained by dissolving 5.14 g (22.1 mmol) of Si($^t$BuNCHCHN$^t$Bu)(H)Cl in 10 mL of hexane was added to a lithium(1,1,3,3-tetramethylbutylamide) solution prepared by adding 10 mL of hexane and 2.94 g (22.8 mmol) of 1,1,3,3-tetramethylbutylamine to 13.8 mL (22.8 mmol) of a hexane solution (concentration: 1.65 mol/L) of butyllithium and stirring the mixture at room temperature for 14 hours, and the resulting mixture was stirred at room temperature for 24 hours. Insoluble matters produced were separated by filtration, and the solvent was removed by distillation from the filtrate under atmospheric pressure. The obtained residue was sublimated (heating temperature: 180° C./64 Pa) to obtain 1,3-di-tert-butyl-2-(1,1,3,3-tetramethylbutyl)amino-1,3-diaza-2-silacyclopent-4-ene (Si($^t$BuNCHCHN$^t$Bu)(H)NH$^t$Oct) as a white solid (yielded amount: 5.85 g, yield: 81%).

$^1$H NMR (500 MHz, C$_6$D$_6$, δ/ppm) 5.80 (d, J=1 Hz, 2H), 5.61 (s, 1H), 1.51 (s, 2H), 1.36 (s, 18H), 1.28 (s, 6H), 1.04 (br, 1H), 1.00 (s, 9H).

$^{13}$C NMR (125 MHz, C$_6$D$_6$, δ/ppm) 111.8, 59.3, 53.9, 51.7, 32.6, 32.2, 32.1, 31.2.

Example-17

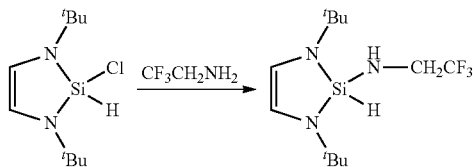

[Chem. 57]

In an argon atmosphere, 5.63 g (24.2 mmol) of Si($^t$BuNCHCHN$^t$Bu)(H)Cl was dissolved in 20 mL of hexane and after adding 5.38 g (54.3 mmol) of 2,2,2-trifluoroethylamine, the mixture was stirred at room temperature for 15 hours. Insoluble matters produced were separated by filtration, and the solvent was removed by distillation from the filtrate under atmospheric pressure. The obtained residue was distilled under reduced pressure (distillation temperature: 80° C./4.7×10$^2$ Pa) to obtain 1,3-di-tert-butyl-2-(2,2,2-trifluoroethyl)amino-1,3-diaza-2-silacyclopent-4-ene (Si($^t$BuNCHCHN$^t$Bu)(H)NHCH$_2$CF$_3$) as a pale yellow liquid (yielded amount: 4.74 g, yield: 66%).

$^1$H NMR (500 MHz, C$_6$D$_6$, δ/ppm) 5.73 (d, J=1 Hz, 2H), 5.47 (s, 1H), 2.89 (quint, J=9 Hz, 2H), 1.19 (s, 18H), 1.02 (br, 1H).

$^{13}$C NMR (125 MHz, C$_6$D$_6$, δ/ppm) 114.8 (q, J=269 Hz), 112.2, 42.7 (q, J=33 Hz), 51.4, 31.1.

Example-18

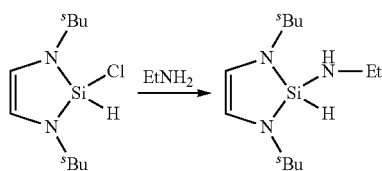

[Chem. 58]

In an argon atmosphere, 3.30 g (73.2 mmol) of ethylamine was dissolved in 30 mL of hexane, and a solution obtained by dissolving 6.21 g (26.7 mmol) of Si($^s$BuNCHCHN$^s$Bu)(H)Cl in 5 mL of hexane was added thereto at −20° C. After stirring at room temperature for 2 hours, insoluble matters produced were separated by filtration, and the solvent was removed by distillation from the filtrate under atmospheric pressure. The obtained residue was distilled under reduced pressure (distillation temperature: 92-96° C./4.0×10$^2$ Pa) to obtain 1,3-di-sec-butyl-2-ethylamino-1,3-diaza-2-silacyclopent-4-ene (Si($^s$BuNCHCHN$^s$Bu)(H)NHEt) as a pale yellow liquid (yielded amount: 5.61 g, yield: 87%). This product was a mixture of a plurality of isomers differing in the steric configuration from each other.

$^1$H NMR (500 MHz, C$_6$D$_6$, δ/ppm) 5.68 (s)/5.66 (s)/5.65 (s) (2H as the total of integrated intensities of three signals), 5.57 (s, 1H), 3.06 (sept, J=7 Hz, 2H), 2.76-2.69 (m, 2H), 1.69-1.59 (m, 2H), 1.51-1.33 (m, 2H), 1.21 (d, J=7 Hz)/1.20 (d, J=7 Hz) (6H as the total of integrated intensities of two signals), 1.00-0.88 (m, 10H).

$^{13}$C NMR (125 MHz, C$_6$D$_6$, δ/ppm) 114.3, 113.9, 113.2, 112.9, 54.1, 54.0, 53.4, 35.2, 31.9, 30.9, 22.9, 22.8, 22.1, 22.0, 20.3, 11.9, 11.74, 11.73.

Example-19

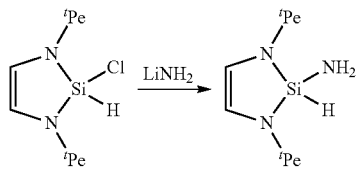

[Chem. 59]

In an argon atmosphere, 379 mg (purity: 95%, 15.7 mmol) of lithium amide was suspended in 10 mL of 1,2-dimethoxyethane and after adding 3.99 g (15.3 mmol) of Si($^t$PeNCHCHN$^t$Pe)(H)Cl, the mixture was stirred at room temperature for 3 hours. To the reaction mixture, 10 mL of hexane was added, and the mixture was stirred at room temperature for 10 minutes. Insoluble matters produced were separated by filtration, and the solvent was removed by distillation from the filtrate under atmospheric pressure. The obtained residue was distilled under reduced pressure (distillation temperature: 90° C./3.7×10$^2$ Pa) to obtain 2-amino-1,3-di-tert-pentyl-1,3-diaza-2-silacyclopent-4-ene (Si($^t$PeNCHCHN$^t$Pe)(H)NH$_2$) as a pale yellow liquid (yielded amount: 3.23 g, yield: 87%).

$^1$H NMR (500 MHz, C$_6$D$_6$, δ/ppm) 5.72 (d, J=1 Hz, 2H), 5.69 (t, J=5 Hz, 1H), 1.56 (dq, J=14 Hz, 7 Hz, 2H), 1.48 (dq, J=14 Hz, 7 Hz, 2H), 1.26 (s, 6H), 1.25 (s, 6H), 0.87 (t, J=7 Hz, 6H), 0.85 (br, 2H).

$^{13}$C NMR (125 MHz, C$_6$D$_6$, δ/ppm) 111.7, 54.0, 35.6, 29.3, 28.7, 9.1.

Example-20

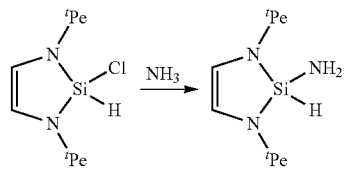

[Chem. 60]

In an argon atmosphere, 6.18 g (23.7 mmol) of Si($^t$PeNCHCHN$^t$Pe)(H)Cl was dissolved in 20 mL of hexane. The resulting solution was deaerated by Freeze-Pump-Thaw cycling and after creating an ammonia atmosphere in the reaction vessel by connecting thereto a balloon having an internal volume of 5 L and being filled with ammonia, the solution was stirred at room temperature for 6 hours. Insoluble matters produced were separated by filtration, and the solvent was removed by distillation from the filtrate under atmospheric pressure. The obtained residue was distilled under reduced pressure (distillation temperature: 90° C./3.7×10$^2$ Pa) to obtain 2-amino-di-1,3-tert-pentyl-1,3-diaza-2-silacyclopent-4-ene (Si($^t$PeNCHCHN$^t$Pe)(H)NH$_2$) as a pale yellow liquid (yielded amount: 5.36 g, yield: 94%). The thus-obtained Si($^t$PeNCHCHN$^t$Pe)(H)NH$_2$ was measured for the $^1$H and $^{13}$C NMR spectra, as a result, these spectra agreed with spectra of that obtained in Example-19.

Example-21

[Chem. 61]

In an argon atmosphere, 5.24 g (20.1 mmol) of Si($^t$PeNCHCHN$^t$Pe)(H)Cl was dissolved in 20 mL of hexane and after adding 24.0 mL (46.8 mmol) of a tetrahydrofuran solution (concentration: 1.95 mol/L) of methylamine, the mixture was stirred at room temperature for 3 hours. Insoluble matters produced were separated by filtration, and the solvent was removed by distillation from the filtrate under atmospheric pressure. The obtained residue was distilled under reduced pressure (distillation temperature: 104° C./3.8×10$^2$ Pa) to obtain 2-methylamino-1,3-di-tert-pentyl-1,3-diaza-2-silacyclopent-4-ene (Si($^t$PeNCHCHN$^t$Pe)(H)NHMe) as a pale yellow liquid (yielded amount: 4.71 g, yield: 92%).

$^1$H NMR (500 MHz, C$_6$D$_6$, δ/ppm) 5.73 (d, J=1 Hz, 2H), 5.62 (s, 1H), 2.34 (d, J=7 Hz, 3H), 1.58 (dq, J=14 Hz, 7 Hz, 2H), 1.48 (dq, J=14 Hz, 7 Hz, 2H), 1.25 (s, 6H), 1.24 (s, 6H), 0.88 (t, J=7 Hz, 6H), 0.64 (br, 1H).

$^{13}$C NMR (125 MHz, C$_6$D$_6$, δ/ppm) 111.8, 53.8, 35.6, 29.2, 28.4, 26.4, 9.2.

Example-22

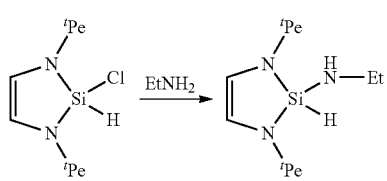

[Chem. 62]

In an argon atmosphere, 6.80 g (151 mmol) of ethylamine was dissolved in 25 mL of hexane, and a solution obtained by dissolving 6.96 g (26.7 mmol) of Si($^r$PeNCHCHN$^r$Pe)(H)Cl in 5 mL of hexane was added thereto at −20° C. After stirring at room temperature for 3 hours, insoluble matters produced were separated by filtration, and the solvent was removed by distillation from the filtrate under atmospheric pressure. The obtained residue was distilled under reduced pressure (distillation temperature: 110° C./1.5×10$^2$ Pa) to obtain 2-ethylamino-1,3-di-tert-pentyl-1,3-diaza-2-silacyclopent-4-ene (Si($^r$PeNCHCHN$^r$Pe)(H)NHEt) as a pale yellow liquid (yielded amount: 6.63 g, yield: 92%).

$^1$H NMR (500 MHz, C$_6$D$_6$, δ/ppm) 5.72 (d, J=1 Hz, 2H), 5.64 (s, 1H), 2.73 (quint, J=7 Hz, 2H), 1.60 (dq, J=14 Hz, 7 Hz, 2H), 1.48 (dq, J=14 Hz, 7 Hz, 2H), 1.27 (s, 6H), 1.25 (s, 6H), 0.94 (t, J=7 Hz, 3H), 0.89 (t, J=7 Hz, 6H), 0.83 (br, 1H).

$^{13}$C NMR (125 MHz, C$_6$D$_6$, δ/ppm) 111.8, 53.9, 35.7, 35.2, 29.3, 28.3, 19.9, 9.2.

Example-23

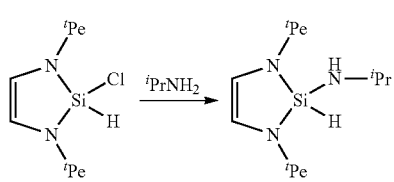

[Chem. 63]

In an argon atmosphere, 6.49 g (24.9 mmol) of Si($^r$PeNCHCHN$^r$Pe)(H)Cl was dissolved in 25 mL of hexane and after adding 2.96 g (50.1 mmol) of isopropylamine, the mixture was stirred at room temperature for 3 hours. Insoluble matters produced were separated by filtration, and the solvent was removed by distillation from the filtrate under atmospheric pressure. The obtained residue was sublimated (heating temperature: 160° C./70 Pa) to obtain 2-isopropylamino-1,3-di-tert-pentyl-1,3-diaza-2-silacyclopent-4-ene (Si($^r$PeNCHCHN$^r$Pe)(H)NH$^i$Pr) as a white solid (yielded amount: 6.77 g, yield: 96%).

$^1$H NMR (500 MHz, C$_6$D$_6$, δ/ppm) 5.73 (s, 2H), 5.66 (s, 1H), 3.22 (m, 1H), 1.64 (dq, J=14 Hz, 7 Hz, 2H), 1.46 (dq, J=14 Hz, 7 Hz, 2H), 1.30 (s, 6H), 1.27 (s, 6H), 1.00 (d, J=7 Hz, 6H), 0.90 (t, J=7 Hz, 6H), 0.86 (br, 1H).

$^{13}$C NMR (125 MHz, C$_6$D$_6$, δ/ppm) 111.8, 42.3, 35.7, 29.4, 28.0, 27.5, 9.1.

Example-24

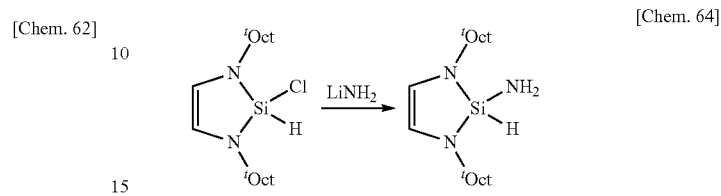

[Chem. 64]

In an argon atmosphere, 439 mg (purity: 95%, 18.2 mmol) of lithium amide was suspended in 20 mL of 1,2-dimethoxyethane and after adding 6.07 g (17.6 mmol) of Si($^t$Oct-NCHCHN$^t$Oct)(H)Cl, the mixture was stirred at room temperature for 4 hours. To the reaction mixture, 20 mL of hexane was added, and the mixture was stirred at room temperature for 10 minutes. Insoluble matters produced were separated by filtration, and the solvent was removed by distillation from the filtrate under atmospheric pressure. The obtained residue was distilled under reduced pressure (distillation temperature: 116° C./1.3×10$^2$ Pa) to obtain 2-amino-1,3-bis(1,1,3,3-tetramethylbutyl)-1,3-diaza-2-silacyclopent-4-ene (Si($^t$Oct-NCHCHN$^t$Oct)(H)NH$_2$) as a pale yellow liquid (yielded amount: 4.99 g, yield: 87%).

$^1$H NMR (500 MHz, C$_6$D$_6$, δ/ppm) 5.73 (d, J=1 Hz, 2H), 5.70 (s, 1H), 1.63 (d, J=15 Hz, 2H), 1.46 (d, J=15 Hz, 2H), 1.41 (s, 6H), 1.35 (s, 6H), 1.05 (s, 18H), 0.88 (br, 2H).

$^{13}$C NMR (125 MHz, C$_6$D$_6$, δ/ppm) 111.9, 55.2, 54.2, 32.8, 32.1, 32.0, 31.2.

Example-25

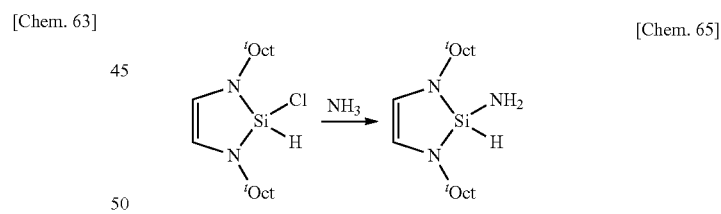

[Chem. 65]

In an argon atmosphere, 5.42 g (15.7 mmol) of Si($^t$Oct-NCHCHN$^t$Oct)(H)Cl was dissolved in 20 mL of hexane. The resulting solution was deaerated by Freeze-Pump-Thaw cycling and after creating an ammonia atmosphere in the reaction vessel by connecting thereto a balloon having an internal volume of 5 L and being filled with ammonia, the solution was stirred at room temperature for 41 hours. Insoluble matters produced were separated by filtration, and the solvent was removed by distillation from the filtrate under atmospheric pressure. The obtained residue was distilled under reduced pressure (distillation temperature: 115° C./1.2×10$^2$ Pa) to obtain 2-amino-1,3-bis(1,1,3,3-tetramethylbutyl)-1,3-diaza-2-silacyclopent-4-ene (Si($^t$Oct-NCHCHN$^t$Oct)(H)NH$_2$) as a pale yellow liquid (yielded amount: 4.52 g, yield: 88%). The thus-obtained Si($^t$Oct- NCHCHN'Oct)(H)NH₂ was measured for the ¹H and ¹³C NMR spectra, as a result, these spectra agreed with spectra of that obtained in Example-24.

Example-26

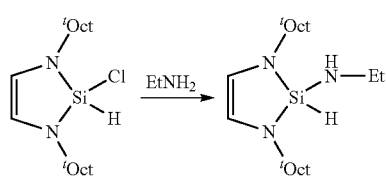

In an argon atmosphere, 6.80 g (151 mmol) of ethylamine was dissolved in 20 mL of hexane, and a solution obtained by dissolving 5.26 g (15.2 mmol) of Si('OctNCHCHN'Oct)(H)Cl in 10 mL of hexane was added thereto at −20° C. After stirring at room temperature for 12 hours, insoluble matters produced were separated by filtration, and the solvent was removed by distillation from the filtrate under atmospheric pressure. The obtained residue was distilled under reduced pressure (distillation temperature: 128° C./1.4×10² Pa) to obtain 1,3-bis(1,1,3,3-tetramethylbutyl)-2-ethylamino-1,3-diaza-2-silacyclopent-4-ene (Si('OctNCHCHN'Oct)(H)NHEt) as a pale yellow liquid (yielded amount: 5.22 g, yield: 97%).

¹H NMR (500 MHz, C₆D₆, δ/ppm) 5.74 (s, 2H), 5.64 (s, 1H), 2.73 (quint, J=7 Hz, 2H), 1.72 (d, J=15 Hz, 2H), 1.45 (s, 6H), 1.43 (d, J=15 Hz, 2H), 1.33 (s, 6H), 1.06 (s, 18H), 0.95 (t, J=7 Hz, 3H), 0.83 (br, 1H).

¹³C NMR (125 MHz, C₆D₆, δ/ppm) 111.9, 55.2, 54.3, 35.5, 33.0, 32.1, 32.0, 30.5, 19.9.

Example-27

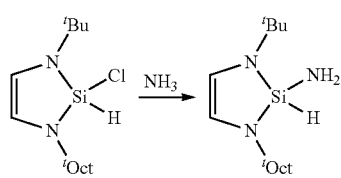

In an argon atmosphere, 4.87 g (16.9 mmol) of Si('BuNCHCHN'Oct)(H)Cl was dissolved in 20 mL of hexane. The resulting solution was deaerated by Freeze-Pump-Thaw cycling and after creating an ammonia atmosphere in the reaction vessel by connecting thereto a balloon having an internal volume of 5 L and being filled with ammonia, the solution was stirred at room temperature for 19 hours. Insoluble matters produced were separated by filtration, and the solvent was removed by distillation from the filtrate under atmospheric pressure. The obtained residue was distilled under reduced pressure (distillation temperature: 114° C./3.3×10² Pa) to obtain 2-amino-3-tert-butyl-1-1,1,3,3-tetramethylbutyl-1,3-diaza-2-silacyclopent-4-ene (Si('BuNCHCHN'Oct)(H)NH₂) as a pale yellow liquid (yielded amount: 4.02 g, yield: 88%).

¹H NMR (500 MHz, C₆D₆, δ/ppm) 5.79 (dd, J=4 Hz, 1 Hz, 1H), 5.74 (dd, J=4 Hz, 1 Hz, 1H), 5.69 (t, J=5 Hz, 1H), 1.65 (d, J=15 Hz, 1H), 1.46 (d, J=15 Hz, 1H), 1.41 (s, 3H), 1.35 (s, 3H), 1.28 (s, 9H), 1.05 (s, 9H), 0.85 (br, 2H).

¹³C NMR (125 MHz, C₆D₆, δ/ppm) 112.4, 111.4, 55.2, 54.4, 51.4, 32.8, 32.1, 32.0, 31.4, 31.1.

Example-28

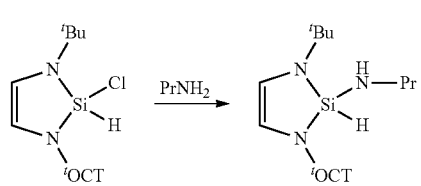

In an argon atmosphere, 4.82 g (16.9 mmol) of Si('BuNCHCHN'Oct)(H)Cl was dissolved in 40 mL of hexane and after adding 2.02 g (34.2 mmol) of propylamine, the mixture was stirred at room temperature for 3 hours. Insoluble matters produced were separated by filtration, and the solvent was removed by distillation from the filtrate under atmospheric pressure. The obtained residue was distilled under reduced pressure (distillation temperature: 106° C./97 Pa) to obtain 1-1,1,3,3-tetramethylbutyl-3-tert-butyl-2-propylamino-1,3-diaza-2-silacyclopent-4-ene (Si('BuNCHCHN'Oct)(H)NHPr) as a pale yellow liquid (yielded amount: 4.53 g, yield: 87%).

¹H NMR (500 MHz, C₆D₆, δ/ppm) 5.80 (dd, J=4 Hz, 1 Hz, 2H), 5.75 (dd, J=4 Hz, 1 Hz, 2H), 5.67 (s, 1H), 2.66 (q, J=7 Hz, 2H), 1.73 (d, J=15 Hz, 1H), 1.46 (s, 3H), 1.43 (d, J=15 Hz, 1H), 1.33 (s, 3H), 1.32 (sext, J=7 Hz, 2H), 1.30 (s, 9H), 1.06 (s, 9H), 0.96 (br, 1H), 0.77 (t, J=7 Hz, 3H).

¹³C NMR (125 MHz, C₆D₆, δ/ppm) 112.4, 111.5, 55.1, 54.5, 51.3, 42.8, 33.1, 32.1, 32.0, 31.3, 30.4, 27.7, 11.9.

Example-29

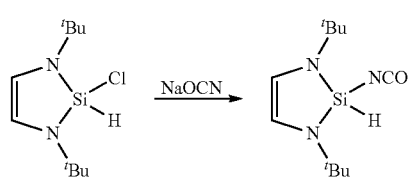

In an argon atmosphere, 7.69 g (33.0 mmol) of Si('BuNCHCHN'Bu)(H)Cl was dissolved in 30 mL of tetrahydrofuran and after adding 2.58 g (purity: 90%, 35.7 mmol) of sodium cyanate, the mixture was stirred for 8 hours under heating and refluxing. Insoluble matters produced were separated by filtration, and the solvent was removed by distillation from the filtrate under atmospheric pressure. The obtained residue was distilled under reduced pressure (distillation temperature: 85° C./3.3×10² Pa) to obtain 1,3-di-tert-butyl-2-isocyanato-1,3-diaza-2-silacyclopent-4-ene (Si('BuNCHCHN'Bu)(H)NCO) as a colorless liquid (yielded amount: 7.09 g, yield: 90%).

¹H NMR (500 MHz, C₆D₆, δ/ppm) 5.68 (s, 2H), 5.63 (s, 1H), 1.12 (s, 18H).

$^{13}$C NMR (125 MHz, C$_6$D$_6$, δ/ppm) 125.0, 112.7, 51.4, 30.9.

Example-30

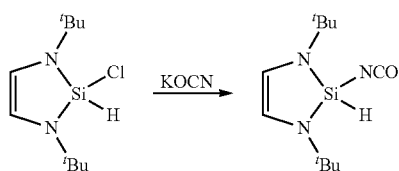
[Chem. 70]

In an argon atmosphere, 8.33 g (35.8 mmol) of Si($^t$BuNCHCHN$^t$Bu)(H)Cl was dissolved in 30 mL of tetrahydrofuran and after adding 3.19 g (purity: 96%, 37.8 mmol) of potassium cyanate, the mixture was stirred for 15 hours under heating and refluxing. Insoluble matters produced were separated by filtration, and the solvent was removed by distillation from the filtrate under atmospheric pressure. The obtained residue was distilled under reduced pressure (distillation temperature: 85° C./3.3×10$^2$ Pa) to obtain 1,3-di-tert-butyl-2-isocyanato-1,3-diaza-2-silacyclopent-4-ene (Si($^t$BuNCHCHN$^t$Bu)(H)NCO) as a colorless liquid (yielded amount: 7.07 g, yield: 83%). The thus-obtained Si($^t$BuNCHCHN$^t$Bu)(H)NCO was measured for the $^1$H and $^{13}$C NMR spectra, as a result, these spectra agreed with spectra of that obtained in Example-29.

Example-31

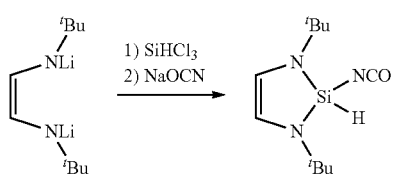
[Chem. 71]

In an argon atmosphere, a dilithium(N,N'-di-tert-butyl-1,2-vinylenediaminide) solution prepared by using 32.16 g of $^t$BuNCHCHN$^t$Bu, 250 mL of tetrahydrofuran and 2.67 g of lithium according to the procedure described in Reference Example-9 was added to a hexane (30 mL) solution containing 25.12 g (185.5 mmol) of trichlorosilane, and the mixture was stirred at room temperature for 3 hours. To this reaction mixture, 14.47 g (purity: 96%, 213.7 mmol) of sodium cyanate was added, and the mixture was stirred for 4 hours under heating an refluxing. Insoluble matters produced were separated by filtration, and the solvent was removed by distillation from the filtrate under atmospheric pressure. The obtained residue was distilled under reduced pressure (distillation temperature: 85° C./3.3×10$^2$ Pa) to obtain 1,3-di-tert-butyl-2-isocyanato-1,3-diaza-2-silacyclopent-4-ene (Si($^t$BuNCHCHN$^t$Bu)(H)NCO) as a colorless liquid (yielded amount: 35.44 g, yield: 80%). The thus-obtained Si($^t$BuNCHCHN$^t$Bu)(H)NCO was measured for the $^1$H and $^{13}$C NMR spectra, as a result, these spectra agreed with spectra of those obtained in Example-29 and Example-30.

Example-32

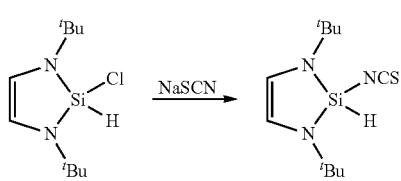
[Chem. 72]

In an argon atmosphere, 6.10 g (26.2 mmol) of Si($^t$BuNCHCHN$^t$Bu)(H)Cl was dissolved in 20 mL of tetrahydrofuran and after adding 2.15 g (purity: 99%, 26.3 mmol) of sodium thiocyanate, the mixture was stirred at room temperature for 14 hours. Insoluble matters produced were separated by filtration, and the solvent was removed by distillation from the filtrate under atmospheric pressure. The obtained residue was distilled under reduced pressure (distillation temperature: 108° C./3.3×10$^2$ Pa) to obtain 1,3-di-tert-butyl-2-thioisocyanato-1,3-diaza-2-silacyclopent-4-ene (Si($^t$BuNCHCHN$^t$Bu)(H)NCS) as a pale yellow liquid (yielded amount: 6.05 g, yield: 90%).

$^1$H NMR (500 MHz, C$_6$D$_6$, δ/ppm) 5.63 (d, J=2 Hz, 2H), 5.52 (s, 1H), 1.10 (s, 18H).

$^{13}$C NMR (125 MHz, C$_6$D$_6$, δ/ppm) 144.1, 112.8, 51.5, 30.8.

Example-33

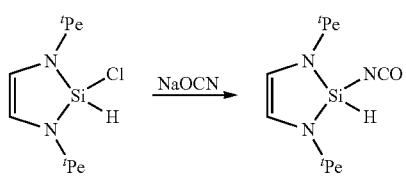
[Chem. 73]

In an argon atmosphere, 11.3 g (43.3 mmol) of Si($^t$PeNCHCHN$^t$Pe)(H)Cl was dissolved in 80 mL of tetrahydrofuran and after adding 2.81 g (purity: 96%, 41.6 mmol) of sodium cyanate, the mixture was stirred for 18.5 hours under heating and refluxing. Insoluble matters produced were separated by filtration, and the solvent was removed by distillation from the filtrate under reduced pressure. The obtained residue was distilled under reduced pressure (86° C./9.6×10$^2$ Pa) to obtain 2-isocyanato-1,3-di-tert-pentyl-1,3-diaza-2-silacyclopent-4-ene (Si($^t$PeNCHCHN$^t$Pe)(H)NCO) as a colorless liquid (yielded amount: 9.37 g, yield: 84%).

$^1$H NMR (500 MHz, C$_6$D$_6$, δ/ppm) 5.68 (s, 1H), 5.62 (s, 1H), 5.61 (s, 1H), 1.36 (q, J=8 Hz, 2H), 1.35 (q, J=8 Hz, 2H), 1.10 (s, 6H), 1.09 (s, 6H), 0.76 (t, J=8 Hz, 6H).

$^{13}$C NMR (125 MHz, C$_6$D$_6$, δ/ppm) 125.3, 112.1, 53.8, 34.9, 28.3, 28.2, 8.59.

$^{13}$C NMR (125 MHz, C$_6$D$_6$, δ/ppm) 112.0, 51.1, 35.6, 31.0.

Example-34

Example-36

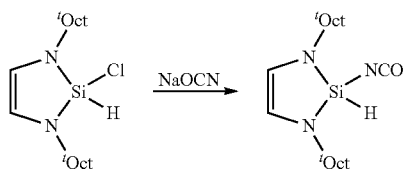

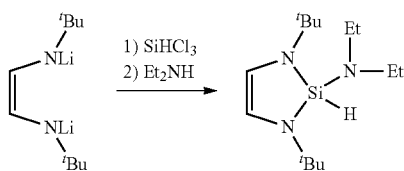

In an argon atmosphere, 7.57 g (22.0 mmol) of Si($^t$Oct-NCHCHN$^t$Oct)(H)Cl was dissolved in 30 mL of tetrahydrofuran and after adding 2.14 g (purity: 96%, 31.6 mmol) of sodium cyanate, the mixture was stirred for 18 hours under heating and refluxing. Insoluble matters produced were separated by filtration, and the solvent was removed by distillation from the filtrate under atmospheric pressure. The obtained residue was distilled under reduced pressure (distillation temperature: 117° C./73 Pa) to obtain 2-isocyanato-1,3-bis(1,1,3,3-tetramethylbutyl)-1,3-diaza-2-silacyclopent-4-ene (Si($^t$OctNCHCHN$^t$Oct)(H)NCO) as a colorless liquid (yielded amount: 6.91 g, yield: 89%).

$^1$H NMR (500 MHz, C$_6$D$_6$, δ/ppm) 5.70 (s, 1H), 5.63 (s, 2H), 1.51 (d, J=14 Hz, 2H), 1.30 (d, J=14 Hz, 2H), 1.28 (s, 6H), 1.19 (s, 6H), 0.95 (s, 18H).

$^{13}$C NMR (125 MHz, C$_6$D$_6$, δ/ppm) 125.1, 112.6, 55.2, 53.7, 32.6, 31.9, 31.8, 30.5.

In an argon atmosphere, a dilithium(N,N'-di-tert-butyl-1,2-vinylenediaminide) solution prepared by using 32.00 g of $^t$BuNCHCHN$^t$Bu, 50 mL of tetrahydrofuran, 150 mL of hexane and 2.67 g of lithium according to the procedure described in Reference Example-9 was added to a hexane (120 mL) solution containing 25.20 g (186.0 mmol) of trichlorosilane, and the mixture was stirred at room temperature for 4 hours. To this reaction mixture, 30.00 g (410.2 mmol) of diethylamine was added, and the mixture was stirred at room temperature for 5 hours. Insoluble matters produced were separated by filtration, and the solvent was removed by distillation from the filtrate under atmospheric pressure. The obtained residue was distilled under reduced pressure (distillation temperature: 102° C./4.0×10$^2$ Pa) to obtain 1,3-di-tert-butyl-2-diethylamino-1,3-diaza-2-silacyclopent-4-ene (Si($^t$BuNCHCHN$^t$Bu)(H)NEt$_2$) as a pale yellow liquid (yielded amount: 30.29 g, yield: 60%).

$^1$H NMR (500 MHz, C$_6$D$_6$, δ/ppm) 5.82 (s, 2H), 5.69 (s, 1H), 2.85 (q, J=7 Hz, 4H), 1.26 (s, 18H), 1.00 (t, J=7 Hz, 6H).

$^{13}$C NMR (125 MHz, C$_6$D$_6$, δ/ppm) 112.1, 51.3, 38.6, 31.2, 15.1.

Example-35

Example-37

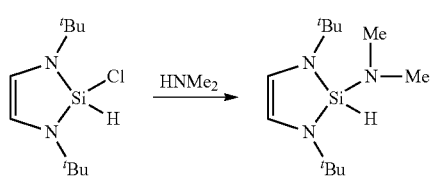

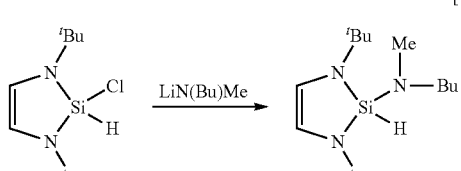

In an argon atmosphere, 3.98 g (17.1 mmol) of Si($^t$BuNCHCHN$^t$Bu)(H)Cl was dissolved in 20 mL of hexane. The resulting solution was deaerated by Freeze-Pump-Thaw cycling and after creating a dimethylamine atmosphere in the reaction vessel by connecting thereto a balloon having an internal volume of 5 L and being filled with dimethylamine, the solution was stirred at room temperature for 20 hours. Insoluble matters produced were separated by filtration, and the solvent was removed by distillation from the filtrate under atmospheric pressure. The obtained residue was distilled under reduced pressure (distillation temperature: 84° C./4.7×10$^2$ Pa) to obtain 1,3-di-tert-butyl-2-dimethylamino-1,3-diaza-2-silacyclopent-4-ene (Si($^t$BuNCHCHN$^t$Bu)(H) NMe$_2$) as a colorless liquid (yielded amount: 3.76 g, yield: 91%).

$^1$H NMR (500 MHz, C$_6$D$_6$, δ/ppm) 5.83 (s, 2H), 5.63 (s, 1H), 2.38 (s, 6H), 1.22 (s, 18H).

In an argon atmosphere, 5.50 g (23.6 mmol) of Si($^t$BuNCHCHN$^t$Bu)(H)Cl was dissolved in 10 mL of hexane and after adding a lithium butyl(methyl)amide solution (prepared by mixing 14.2 mL of 1.67 mol/L butyllithium hexane solution, 15 mL of tetrahydrofuran and 2.07 g of N-butyl-N-methylamine and stirring the mixture at room temperature for 1 hour), the mixture was stirred at room temperature for 20 hours. Insoluble matters produced were separated by filtration, and the solvent was removed by distillation from the filtrate under atmospheric pressure. The obtained residue was distilled under reduced pressure (distillation temperature: 109° C./3.3×10$^2$ Pa) to obtain 1,3-di-tert-butyl-2-butylmethylamino-1,3-diaza-2-silacyclopent-4-ene (Si($^t$BuNCHCHN$^t$Bu)(H)NBuMe) as a colorless liquid (yielded amount: 5.67 g, yield: 85%).

$^1$H NMR (500 MHz, C$_6$D$_6$, δ/ppm) 5.85 (s, 2H), 5.68 (s, 1H), 2.75 (m, 2H), 2.40 (s, 3H), 1.46 (m, 2H), 1.26 (s, 18H), 1.21 (m, 2H), 0.88 (t, J=7 Hz, 3H).
$^{13}$C NMR (125 MHz, C$_6$D$_6$, δ/ppm) 112.1, 51.2, 48.7, 32.7, 31.6, 31.1, 21.1, 14.6.

Example-38

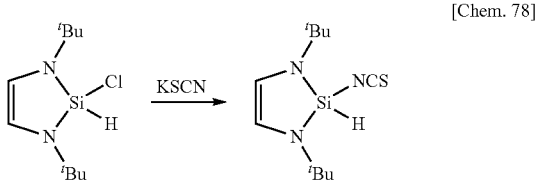

[Chem. 78]

In an argon atmosphere, 3.36 g (14.4 mmol) of Si($^t$BuNCHCHN$^t$Bu)(H)Cl was dissolved in 20 mL of tetrahydrofuran and after adding 1.47 g (purity: 98%, 14.8 mmol) of potassium cyanate, the mixture was stirred at room temperature for 18 hours. Insoluble matters produced were separated by filtration, and the solvent was removed by distillation from the filtrate under atmospheric pressure. The obtained residue was distilled under reduced pressure (distillation temperature: 108° C./3.3×10$^2$ Pa) to obtain 1,3-di-tert-butyl-2-thioisocyanato-1,3-diaza-2-silacyclopent-4-ene (Si($^t$BuNCHCHN$^t$Bu)(H)NCS) as a pale yellow liquid (yielded amount: 3.28 g, yield: 89%). The thus-obtained Si($^t$BuNCHCHN$^t$Bu)(H)NCS was measured for the $^1$H and $^{13}$C NMR spectra, as a result, these spectra agreed with spectra of that obtained in Example-32.

Thin Film Production Examples

Example-39 to Example-47 and Comparative Example-1 to Comparative Example-3

Silicon-containing thin films were produced by thermal CVD method using the hydrosilane derivative of the present invention or SiH(NMe$_2$)$_3$ (TDMAS) as the material. FIG. 1 schematically shows the apparatus used for thin film production. The deposition conditions were as shown in Table 1. Incidentally, sccm is the unit showing the flow rate of a gas, and 1 sccm indicates that a gas is moving at a speed of 2.68 mmol/h in terms of ideal gas. The feed rate of the material to the reaction chamber can be determined according to the calculation formula of (flow rate of carrier gas×vapor pressure of material÷total pressure in material vessel), and, for example, the material vessel temperature or the carrier gas (argon) flow rate was adjusted so as to make the material feed rate uniform as much as possible throughout all deposition examples of Example-39 to Example-47 and Comparative Example-1 to Comparative Example-3. Also, in addition to the material and the carrier gas, an oxygen gas was introduced into the reaction chamber at a flow rate of 60 sccm. Furthermore, the amount of the diluent gas (argon) introduced was adjusted so as to make uniform the oxygen concentration in the reaction chamber and the total gas flow rate (linear velocity) throughout all deposition examples of Example-39 to Example-47 and Comparative Example-1 to Comparative Example-3. That is, the pressure in the reaction chamber was adjusted to 1.3 kPa by introducing the diluent gas at a flow rate of 220 sccm in Example-39 to Example-47 and at a flow rate of 230 sccm in Comparative Example-1 to Comparative Example-3. The substrate material used was sapphire, and the deposition time was 1 hour. In all of Example-39 to Example-47 and Comparative Example-1 to Comparative Example-3, when the film produced was confirmed by X-ray fluorescence analysis, a characteristic X-ray based on silicon was detected. The film thickness computed from the intensity of the detected X-ray is shown in Table 1. As apparent from Table 1, in Comparative Example-1 to Comparative Example-3, where production of a silicon dioxide thin film by the CVD method using TDMAS and an oxygen gas was tried, it was confirmed that deposition of a film scarcely proceeds at a substrate temperature of 500° C. or less. With respect to Example-39, Example-41, Example-44 and Example-46, the film composition was confirmed by X-ray photoelectron spectroscopy, as a result, the film was revealed to be a silicon dioxide film.

Example-48

A silicon-containing thin film was produced by the thermal CVD method using Si($^t$BuNCHCHN$^t$Bu)(H)NH$_2$ as the material. FIG. 1 schematically shows the apparatus used for thin film production. The deposition conditions were as follows: temperature of material vessel: 40° C., vapor pressure of material: 31 Pa, carrier gas (argon) flow rate: 20 sccm, total pressure in material vessel: 13.3 kPa, feed rate of material to reaction chamber: 0.13 mmol/h, diluent gas (argon) flow rate: 280 sccm, total pressure in reaction chamber: 1.3 kPa, and substrate temperature: 500° C. Feeding of an oxygen gas was not performed. The substrate material used was sapphire, and the deposition time was 1 hour. When the film produced was confirmed by X-ray fluorescence analysis, a characteristic X-ray based on silicon was detected. The film thickness was computed from the intensity of the detected X-ray and found to be 20 nm. Also, the film composition was confirmed by X-ray photoelectron spectroscopy, as a result, the film was revealed to be a film containing silicon and nitrogen.

Example-49

A silicon-containing thin film was produced by the thermal CVD method using Si($^t$BuNCHCHN$^t$Bu)(H)NH$_2$ as the material. FIG. 1 schematically shows the apparatus used for thin film production. The deposition conditions were the same as in Example-48 except that the substrate temperature was 475° C. When the film produced was confirmed by X-ray fluorescence analysis, a characteristic X-ray based on silicon was detected. The film thickness was computed from the intensity of the detected X-ray and found to be 10 nm.

Example-50

A silicon-containing thin film was produced by the thermal CVD method using Si($^t$BuNCHCHN$^t$Bu)(H)NH$_2$ as the material. FIG. 1 schematically shows the apparatus used for thin film production. The deposition conditions were as follows: temperature of material vessel: 40° C., vapor pressure of material: 31 Pa, carrier gas (argon) flow rate: 40 sccm, total pressure in material vessel: 13.3 kPa, feed rate of material to reaction chamber: 0.26 mmol/h, diluent gas (argon) flow rate: 60 sccm, total pressure in reaction chamber: 1.3 kPa, and substrate temperature: 500° C. Feeding of an oxygen gas was not performed. The substrate material used was sapphire, and the deposition time was 1 hour. When the film produced was confirmed by X-ray fluorescence analysis, a characteristic X-ray based on silicon was detected. The film thickness was computed from the intensity of the detected X-ray and found to be 131 nm. Also, the film composition was confirmed by X-ray photoelectron spectroscopy, as a result, the film was revealed to be a film containing silicon and nitrogen.

Example-51

A silicon-containing thin film was produced by the thermal CVD method using Si($^t$BuNCHCHN$^t$Bu)(H)NH$_2$ as the material. FIG. 1 schematically shows the apparatus used for thin film production. The deposition conditions were the same as in Example-50 except that the substrate temperature was 475° C. When the film produced was confirmed by X-ray fluorescence analysis, a characteristic X-ray based on silicon was detected. The film thickness was computed from the intensity of the detected X-ray and found to be 50 nm.

Example-52

A silicon-containing thin film was produced by the thermal CVD method using Si($^t$BuNCHCHN$^t$Bu)(H)NH$_2$ as the material. FIG. 1 schematically shows the apparatus used for thin film production. The deposition conditions were the same as in Example-50 except that the substrate temperature was 450° C. When the film produced was confirmed by X-ray fluorescence analysis, a characteristic X-ray based on silicon was detected. The film thickness was computed from the intensity of the detected X-ray and found to be 19 nm.

Comparative Example-4

Production of a silicon-containing thin film by the thermal CVD method using SiH(NMe$_2$)$_3$ (TDMAS) as the material was tried. FIG. 1 schematically shows the apparatus used for this test. The deposition conditions were as follows: temperature of material vessel: 1° C., vapor pressure of material: 125 Pa, carrier gas (argon) flow rate: 10 sccm, total pressure in material vessel: 26.7 kPa, feed rate of material to reaction chamber: 0.13 mmol/h, diluent gas (argon) flow rate: 290 sccm, total pressure in reaction chamber: 1.3 kPa, and substrate temperature: 500° C. Feeding of an oxygen gas was not performed. The substrate material used was sapphire, and the deposition time was 1 hour. The substrate surface was examined by X-ray fluorescence analysis so as to confirm the formation of a silicon-containing thin film on the substrate surface. As a result, a characteristic X-ray based on silicon was scarcely detected, and formation of a silicon-containing thin film was not confirmed.

Example-53

[Chem. 79]

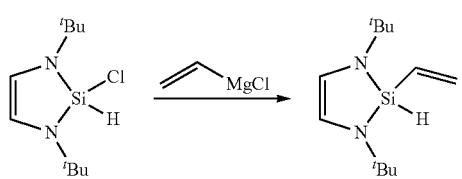

In an argon atmosphere, 6.54 g (28.1 mmol) of Si($^t$BuNCHCHN$^t$Bu)(H)Cl was dissolved in 20 mL of hexane and after adding a vinyl magnesium chloride tetrahydrofuran solution (1.61 mol/L, 34.5 mL, 55.5 mmol), the resulting solution was stirred at room temperature for 22 hours. Insoluble matters produced were separated by filtration, and the solvent was removed by distillation from the filtrate under atmospheric pressure. The obtained residue was distilled under reduced pressure (distillation temperature: 85° C./6.1× 10$^2$ Pa) to obtain 1,3-di-tert-butyl-2-vinyl-1,3-diaza-2-silacyclopent-4-ene (Si($^t$BuNCHCHN$^t$Bu)(H)CHCH$_2$) as a yellow liquid (yielded amount: 3.01 g, yield: 48%).

$^1$H NMR (500 MHz, C$_6$D$_6$, δ/ppm) 6.25 (ddd, J=20 Hz, 14 Hz, 5 Hz, 1H), 6.09 (d, J=5 Hz, 1H), 5.92 (dd, J=20 Hz, 3 Hz, 1H), 5.89 (dd, J=14 Hz, 3 Hz, 1H), 5.77 (s, 2H), 1.19 (s, 18H).

$^{13}$C NMR (125 MHz, C$_6$D$_6$, δ/ppm) 140.3, 133.9, 113.6, 51.5, 31.1.

Example-54

[Chem. 80]

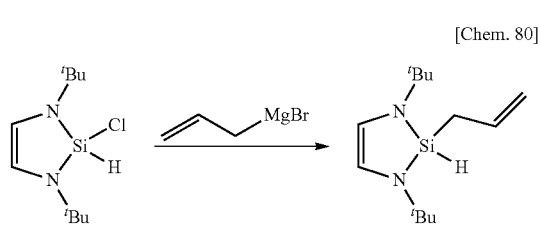

In an argon atmosphere, 8.39 g (36.0 mmol) of Si($^t$BuNCHCHN$^t$Bu)(H)Cl was dissolved in 17 mL of hexane and after adding a (prop-2-en-1-yl)magnesium bromide diethyl ether solution (0.99 mol/L, 38.0 mL, 37.6 mmol), the resulting solution was stirred at room temperature for 18 hours. Insoluble matters produced were separated by filtration, and the solvent was removed by distillation from the filtrate under atmospheric pressure. The obtained residue was distilled under reduced pressure (distillation temperature: 88° C./4.4×10$^2$ Pa) to obtain 1,3-di-tert-butyl-2-(prop-2-en-1-yl)-1,3-diaza-2-silacyclopent-4-ene (Si($^t$BuNCHCHN$^t$Bu)(H) CH$_2$CHCH$_2$) as a yellow liquid (yielded amount: 7.33 g, yield: 85%).

$^1$H NMR (500 MHz, C$_6$D$_6$, δ/ppm) 6.05 (s, 1H), 5.93-5.85 (m, 1H), 5.72 (s, 2H), 5.10-4.90 (m, 2H), 1.77 (dt, J=8 Hz, 1 Hz, 2H), 1.17 (s, 18H).

$^{13}$C NMR (125 MHz, C$_6$D$_6$, δ/ppm) 133.6, 115.0, 113.9, 51.1, 31.2, 31.1.

Example-55

[Chem. 81]

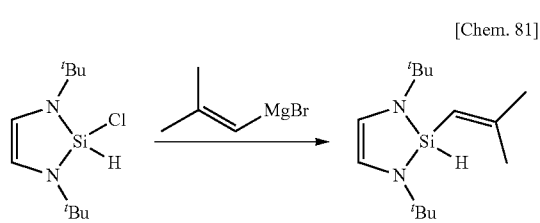

In an argon atmosphere, 8.44 g (36.2 mmol) of Si($^t$BuNCHCHN$^t$Bu)(H)Cl was dissolved in 17 mL of hexane and after adding a (2-methylprop-1-en-1-yl)magnesium bromide tetrahydrofuran solution (0.56 mol/L, 68.0 mL, 38.1 mmol), the resulting solution was stirred at room temperature for 18 hours. Insoluble matters produced were separated by filtration, and the solvent was removed by distillation from the filtrate under atmospheric pressure. The obtained residue was distilled under reduced pressure (distillation temperature: 90° C./3.5×10² Pa) to obtain 1,3-di-tert-butyl-2-(2-methylprop-1-en-1-yl)-1,3-diaza-2-silacyclopent-4-ene (Si(ʹBuNCHCHNʹBu)(H)CHC(CH₃)₂) as a yellow liquid (yielded amount: 6.30 g, yield: 69%).

¹H NMR (500 MHz, C₆D₆, δ/ppm) 6.19 (s, 1H), 5.77 (s, 2H), 5.40 (s, 1H), 1.78 (s, 3H), 1.70 (s, 3H), 1.22 (s, 18H).

¹³C NMR (125 MHz, C₆D₆, δ/ppm) 156.7, 126.7, 112.8, 51.2, 31.0, 29.5, 23.8.

Example-56

[Chem. 82]

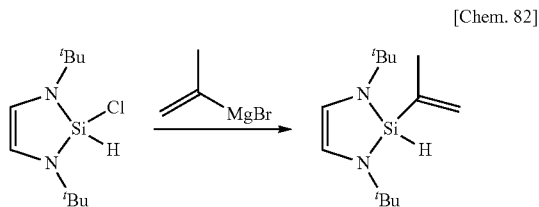

In an argon atmosphere, 8.71 g (37.4 mmol) of Si(ʹBuNCHCHNʹBu)(H)Cl was dissolved in 20 mL of hexane and after adding a (prop-1-en-2-yl)magnesium bromide tetrahydrofuran solution (0.57 mol/L, 69.0 mL, 39.3 mmol), the resulting solution was refluxed for 14 hours. Insoluble matters produced were separated by filtration, and the solvent was removed by distillation from the filtrate under atmospheric pressure. The obtained residue was distilled under reduced pressure (distillation temperature: 80° C./4.3×10² Pa) to obtain 1,3-di-tert-butyl-2-(prop-1-en-2-yl)-1,3-diaza-2-silacyclopent-4-ene (Si(ʹBuNCHCHNʹBu)(H)C(CH₃)CH₂) as a yellow liquid (yielded amount: 4.18 g, yield: 47%).

¹H NMR (500 MHz, C₆D₆, δ/ppm) 6.12 (s, 1H), 5.79 (s, 2H), 5.69 (s, 1H), 5.62 (s, 1H), 1.93 (s, 31-1), 1.11 (s, 18H).

¹³C NMR (125 MHz, C₆D₆, δ/ppm) 149.3, 127.8, 113.8, 51.4, 31.0, 20.6.

Example-57

A silicon-containing thin film was produced by the thermal CVD method using Si(ʹBuNCHCHNʹBu)(H)CH₂CHCH₂ as the material. FIG. 1 schematically shows the apparatus used for thin film production. The deposition conditions were as follows: temperature of material vessel: 43° C., vapor pressure of material: 31 Pa, carrier gas (argon) flow rate: 20 sccm, total pressure in material vessel: 13.3 kPa, feed rate of material to reaction chamber: 0.13 mmol/h, oxygen gas flow rate: 60 sccm, diluent gas (argon) flow rate: 220 sccm, total pressure in reaction chamber: 1.3 kPa, and substrate temperature: 500° C. The substrate material used was sapphire, and the deposition time was 1 hour. When the film produced was confirmed by X-ray fluorescence analysis, a characteristic X-ray based on silicon was detected. The film thickness was computed from the intensity of the detected X-ray and found to be 123 nm. Also, the film composition was confirmed by X-ray photoelectron spectroscopy, as a result, the film was revealed to be a silicon dioxide film.

Example-58

A silicon-containing thin film was produced by the thermal CVD method using Si(ʹBuNCHCHNʹBu)(H)CH₂CHCH₂ as the material. FIG. 1 schematically shows the apparatus used for thin film production. The deposition conditions were the same as in Example-57 except that the substrate temperature was 475° C. When the film produced was confirmed by X-ray fluorescence analysis, a characteristic X-ray based on silicon was detected. The film thickness was computed from the intensity of the detected X-ray and found to be 91 nm.

Example-59

A silicon-containing thin film was produced by the thermal CVD method using Si(ʹBuNCHCHNʹBu)(H)CH₂CHCH₂ as the material. FIG. 1 schematically shows the apparatus used for thin film production. The deposition conditions were the same as in Example-57 except that the substrate temperature was 450° C. When the film produced was confirmed by X-ray fluorescence analysis, a characteristic X-ray based on silicon was detected. The film thickness was computed from the intensity of the detected X-ray and found to be 47 nm.

Example-60

A silicon-containing thin film was produced by the thermal CVD method using Si(ʹBuNCHCHNʹBu)(H)CH₂CHCH₂ as the material. FIG. 1 schematically shows the apparatus used for thin film production. The deposition conditions were as follows: temperature of material vessel: 43° C., vapor pressure of material: 31 Pa, carrier gas (argon) flow rate: 20 sccm, total pressure in material vessel: 13.3 kPa, feed rate of material to reaction chamber: 0.13 mmol/h, diluent gas (argon) flow rate: 280 sccm, total pressure in reaction chamber: 1.3 kPa, and substrate temperature: 500° C. Feeding of an oxygen gas was not performed. The substrate material used was sapphire, and the deposition time was 1 hour. When the film produced was confirmed by X-ray fluorescence analysis, a characteristic X-ray based on silicon was detected. The film thickness was computed from the intensity of the detected X-ray and found to be 74 nm. Also, the film composition was confirmed by X-ray photoelectron spectroscopy, as a result, the film was revealed to be a film containing silicon and nitrogen.

Example-61

A silicon-containing thin film was produced by the thermal CVD method using Si(ʹBuNCHCHNʹBu)(H)CH₂CHCH₂ as the material. FIG. 1 schematically shows the apparatus used for thin film production. The deposition conditions were the same as in Example-60 except that the substrate temperature was 475° C. When the film produced was confirmed by X-ray fluorescence analysis, a characteristic X-ray based on silicon was detected. The film thickness was computed from the intensity of the detected X-ray and found to be 44 nm.

Example-62

A silicon-containing thin film was produced by the thermal CVD method using Si(ʹBuNCHCHNʹBu)(H)CH₂CHCH₂ as the material. FIG. 1 schematically shows the apparatus used for thin film production. The deposition conditions were the same as in Example-60 except that the substrate temperature was 450° C. When the film produced was confirmed by X-ray fluorescence analysis, a characteristic X-ray based on silicon was detected. The film thickness was computed from the intensity of the detected X-ray and found to be 14 nm.

Example-63

A silicon-containing thin film was produced by the thermal CVD method using Si($^t$BuNCHCHN$^t$Bu)(H)CH$_2$CHCH$_2$ as the material. FIG. 1 schematically shows the apparatus used for thin film production. The deposition conditions were as follows: temperature of material vessel: 43° C., vapor pressure of material: 31 Pa, carrier gas (argon) flow rate: 40 sccm, total pressure in material vessel: 13.3 kPa, feed rate of material to reaction chamber: 0.26 mmol/h, diluent gas (argon) flow rate: 60 sccm, total pressure in reaction chamber: 1.3 kPa, and substrate temperature: 500° C. Feeding of an oxygen gas was not performed. The substrate material used was sapphire, and the deposition time was 1 hour. When the film produced was confirmed by X-ray fluorescence analysis, a characteristic X-ray based on silicon was detected. The film thickness was computed from the intensity of the detected X-ray and found to be 277 nm. Also, the film composition was confirmed by X-ray photoelectron spectroscopy, as a result, the film was revealed to be a film containing silicon and nitrogen.

Example-64

A silicon-containing thin film was produced by the thermal CVD method using Si($^t$BuNCHCHN$^t$Bu)(H)CH$_2$CHCH$_2$ as the material. FIG. 1 schematically shows the apparatus used for thin film production. The deposition conditions were the same as in Example-63 except that the substrate temperature was 475° C. When the film produced was confirmed by X-ray fluorescence analysis, a characteristic X-ray based on silicon was detected. The film thickness was computed from the intensity of the detected X-ray and found to be 177 nm.

Example-65

A silicon-containing thin film was produced by the thermal CVD method using Si($^t$BuNCHCHN$^t$Bu)(H)CH$_2$CHCH$_2$ as the material. FIG. 1 schematically shows the apparatus used for thin film production. The deposition conditions were the same as in Example-63 except that the substrate temperature was 450° C. When the film produced was confirmed by X-ray fluorescence analysis, a characteristic X-ray based on silicon was detected. The film thickness was computed from the intensity of the detected X-ray and found to be 77 nm.

A: Material, B: temperature of material vessel [° C.], C: vapor pressure of material [Pa], D: carrier gas flow rate [sccm], E: total pressure in material vessel [kPa], F: feed rate of material to reaction chamber [mmol/h], G: diluent gas (argon) flow rate [sccm], H: total pressure in reaction chamber [kPa], I: substrate temperature [° C.], J: film thickness [nm].

Note 1: sccm is the unit indicating the volume of gas flowed per unit time, and 1 [sccm]=2.68 [mmol/h].

Note 2: The feed rate of material to reaction chamber [mmol/h] can be determined according to the calculation formula of 2.68 [mmol/h/sccm]×(carrier gas flow rate [sccm])×(vapor pressure of material [Pa])÷(total pressure in material vessel [Pa]).

Test Example

Thermogravimetric analysis (TG) and differential scanning calorimetry (DSC) of the hydrosilane derivative of the present invention were performed. In TG, the sample was placed in a measuring apparatus where argon was flowing at a constant rate of 400 ml/min, the decrease in weight due to vaporization when raising the temperatures of the sample and argon at a constant rate of 10° C./min was observed, and the temperature giving a 50% weight loss of sample was recorded. In DSC, the sample was sealed in a stainless steel-made measurement container under an argon atmosphere, heat generation based on pyrolysis of the sample when raising the temperature of the container at a constant rate of 10° C./min was observed, and the temperature at which heat generation started occurring was recorded. A list of these records is shown in Table 2. Also, FIG. 2 to FIG. 32 show the TG and DSC charts of respective samples. In these charts, the abscissa is the centigrade temperature, the left-side ordinate is the percentage of decrease in weight of TG, and the right-side ordinate is the calorific value of DSC.

TABLE 1

| | A | B | C | D [Note-1] | E | F [Note-2] | G | H | I | J |
|---|---|---|---|---|---|---|---|---|---|---|
| Example-39 | Si($^t$BuNCHCHN$^t$Bu)(H)NEt$_2$ | 57 | 31 | 20 | 13.3 | 0.13 | 220 | 1.3 | 500 | 72 |
| Example-40 | | | | | | | | | 475 | 31 |
| Example-41 | Si($^t$BuNCHCHN$^t$Bu)(H)NH$_2$ | 40 | 31 | 20 | 13.3 | 0.13 | 220 | 1.3 | 500 | 121 |
| Example-42 | | | | | | | | | 475 | 70 |
| Example-43 | | | | | | | | | 450 | 30 |
| Example-44 | Si($^t$BuNCHCHN$^t$Bu)(H)NHPr | 60 | 30 | 20 | 13.3 | 0.12 | 220 | 1.3 | 500 | 84 |
| Example-45 | | | | | | | | | 475 | 46 |
| Example-46 | Si($^t$BuNCHCHN$^t$Bu)(H)NCO | 46 | 31 | 20 | 13.3 | 0.13 | 220 | 1.3 | 500 | 59 |
| Example-47 | | | | | | | | | 475 | 21 |
| Comparative Example-1 | TDMAS | 1 | 125 | 10 | 26.7 | 0.13 | 230 | 1.3 | 500 | 6 |
| Comparative Example-2 | | | | | | | | | 475 | 5 |
| Comparative Example-3 | | | | | | | | | 450 | 3 |

TABLE 2

| a | b | c | d | e | f | g |
|---|---|---|---|---|---|---|
| 2 | Si($^i$PrNCHCHN$^i$Pr)(H)NHEt | 28.3 | 157 | 5.9 | 336 | 2 |
| 3 | Si($^i$PrNCHCHN$^i$Pr)(H)NH$^i$Pr | 26.5 | 162 | 6.8 | 326 | 3 |
| 4 | Si($^t$BuNCHCHN$^t$Bu)(H)NH$_2$ | 31.8 | 158 | 5.6 | 320 | 4 |
| 7 | Si($^t$BuNCHCHN$^t$Bu)(H)NHMe | 25.3 | 162 | 5.2 | 342 | 5 |
| 8 | Si($^t$BuNCHCHN$^t$Bu)(H)NHEt | 27.2 | 169 | 9.0 | 335 | 6 |
| 9 | Si($^t$BuNCHCHN$^t$Bu)(H)NH$^n$Pr | 28.4 | 185 | 5.6 | 330 | 7 |
| 10 | Si($^t$BuNCHCHN$^t$Bu)(H)NH$^i$Pr | 26.9 | 169 | 7.8 | 343 | 8 |
| 11 | Si($^t$BuNCHCHN$^t$Bu)(H)NHPr | 23.5 | 181 | 6.5 | 340 | 9 |
| 13 | Si($^t$BuNCHCHN$^t$Bu)(H)NH$^s$Bu | 30.8 | 186 | 7.6 | 340 | 10 |
| 14 | Si($^t$BuNCHCHN$^t$Bu)(H)NH$^t$Bu | 24.3 | 178 | 9.6 | 336 | 11 |
| 15 | Si($^t$BuNCHCHN$^t$Bu)(H)NHCy | 20.7 | 214 | 9.9 | 341 | 12 |
| 16 | Si($^t$BuNCHCHN$^t$Bu)(H)NH$^t$Oct | 16.6 | 205 | 6.6 | 343 | 13 |
| 17 | Si($^t$BuNCHCHN$^t$Bu)(H)NHCH$_2$CF$_3$ | 25.3 | 163 | 11.2 | 340 | 14 |
| 18 | Si($^s$BuNCHCHN$^s$Bu)(H)NHEt | 27.9 | 178 | 6.3 | 330 | 15 |
| 19 | Si($^t$PeNCHCHN$^t$Pe)(H)NH$_2$ | 30.0 | 185 | 7.6 | 315 | 16 |
| 21 | Si($^t$PeNCHCHN$^t$Pe)(H)NHMe | 27.3 | 189 | 5.1 | 336 | 17 |
| 22 | Si($^t$PeNCHCHN$^t$Pe)(H)NHEt | 27.4 | 193 | 5.5 | 341 | 18 |
| 24 | Si($^t$OctNCHCHN$^t$Oct)(H)NH$_2$ | 21.5 | 231 | 5.8 | 300 | 19 |
| 26 | Si($^t$OctNCHCHN$^t$Oct)(H)NHEt | 31.9 | 241 | 6.1 | 317 | 20 |
| 27 | Si($^t$BuNCHCHN$^t$Oct)(H)NH$_2$ | 28.4 | 203 | 7.0 | 283 | 21 |
| 28 | Si($^t$BuNCHCHN$^t$Oct)(H)NHPr | 32.1 | 217 | 6.2 | 292 | 22 |
| 29 | Si($^t$BuNCHCHN$^t$Bu)(H)NCO | 33.4 | 168 | 8.2 | 300 | 23 |
| 32 | Si($^t$BuNCHCHN$^t$Bu)(H)NCS | 26.9 | 195 | 6.3 | 265 | 24 |
| 33 | Si($^t$PeNCHCHN$^t$Pe)(H)NCO | 25.9 | 193 | 9.3 | 303 | 25 |
| 34 | Si($^t$OctNCHCHN$^t$Oct)(H)NCO | 28.9 | 238 | 10.0 | 279 | 26 |
| 36 | Si($^t$BuNCHCHN$^t$Bu)(H)NEt$_2$ | 26.4 | 180 | 7.8 | 315 | 27 |
| 37 | Si($^t$BuNCHCHN$^t$Bu)(H)NBuMe | 30.2 | 193 | 6.9 | 347 | 28 |
| 53 | Si($^t$BuNCHCHN$^t$Bu)(H)CHCH$_2$ | 30.4 | 161 | 8.2 | 256 | 29 |
| 54 | Si($^t$BuNCHCHN$^t$Bu)(H)CH$_2$CHCH$_2$ | 29.9 | 170 | 6.4 | 249 | 30 |
| 55 | Si($^t$BuNCHCHN$^t$Bu)(H)CHC(CH$_3$)$_2$ | 32.0 | 178 | 7.2 | 321 | 31 |
| 56 | Si($^t$BuNCHCHN$^t$Bu)(H)C(CH$_3$)CH$_2$ | 29.9 | 166 | 4.5 | 274 | 32 | a: No. of synthesis example, b: material, c: sample amount by TG measurement [mg], d: temperature at 50% weight loss [° C.], e: sample amount by DSC measurement [mg], f: decomposition temperature [° C.], g: No. of figure.

While the invention has been described in detail and with reference to specific embodiments thereof, it will be apparent to one skilled in the art that various changes and modifications can be made therein without departing from the spirit and scope of the invention.

This application is based on Japanese Patent Application (Patent Application No. 2010-132539) filed on Jun. 10, 2010, Japanese Patent Application (Patent Application No. 2010-200542) filed on Sep. 8, 2010, Japanese Patent Application (Patent Application No. 2010-259888) filed on Nov. 22, 2010, and Japanese Patent Application (Patent Application No. 2011-112373) filed on May 19, 2011, the contents of which are incorporated herein by way of reference.

INDUSTRIAL APPLICABILITY

By virtue of using the hydrosilane derivative (1') of the present invention as the material, a silicon-containing thin film such as silicon dioxide or silicon nitride can be efficiently produced even at a low temperature of 500° C. or less without using a plasma or ozone. Accordingly, the present invention has a remarkable industrial value.

DESCRIPTION OF REFERENCE NUMERALS AND SIGNS

1 Material vessel
2 Constant temperature bath
3 Reaction chamber
4 Substrate
5 Oxygen gas
6 Diluent gas
7 Carrier gas
8 Mass flow controller
9 Mass flow controller
10 Mass flow controller
111 Oil-sealed rotary pump
12 Exhaust

The invention claimed is:

1. A hydrosilane derivative having the structure of formula (1):

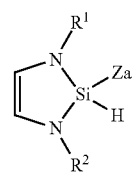

(1)

wherein each of $R^1$ and $R^2$ independently represents an alkyl group having a carbon number of 3 to 12, Za represents an isocyanato group, an isothiocyanato group, an unsubstituted amino group, a mono substituted amino group represented by $NHR^3$, an N-methylalkylamino group represented by $N(CH_3)R^4$, or an alkenyl group having a carbon number of 2 to 6, $R^3$ represents an alkyl group having a carbon number of 1 to 12, which may be substituted with a fluorine atom, and $R^4$ represents an alkyl group having a carbon number of 1 to 4.

2. The hydrosilane derivative as claimed in claim 1, wherein each of $R^1$ and $R^2$ is independently an alkyl group having a carbon number of 3 to 8, Za is an isocyanato group, an unsubstituted amino group, a monosubstituted amino group represented by $NHR^3$, or an alkenyl group having a carbon number of 2 to 4, and $R^3$ is an alkyl group having a carbon number of 1 to 8, which may be substituted with a fluorine atom.

3. The hydro silane derivative as claimed in claim 1, wherein each of $R^1$ and $R^2$ is independently a tert-butyl group or a tert-pentyl group, Za is an unsubstituted amino group or a monosubstituted amino group represented by $NHR^3$, and $R^3$ is an alkyl group having a carbon number of 1 to 4.

4. A method for producing a hydrosilane derivative, comprising reacting a chlorosilane derivative having the structure of formula (3):

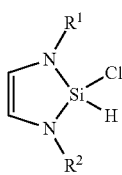
(3)

wherein each of $R^1$ and $R^2$ independently represents an alkyl group having a carbon number of 3 to 12 with a compound having the structure of formula (4):

$M^2Z$ (4)

wherein Z represents an isocyanato group, an isothiocyanato group, an unsubstituted amino group, a monosubstituted amino group represented by $NHR^3$, a disubstituted amino group represented by $NR^4R^5$, or an alkenyl group having a carbon number of 2 to 6, $R^3$ represents an alkyl group having a carbon number of 1 to 12, which may be substituted with a fluorine atom, each of $R^4$ and $R^5$ independently represents an alkyl group having a carbon number of 1 to 4, $M^2$ represents a sodium atom or a potassium atom when Z is an isocyanato group or an isothiocyanato group, $M^2$ represents a hydrogen atom or a lithium atom when Z is an amino group, a monosubstituted amino group represented by $NHR^3$ or a disubstituted amino group represented by $NR^4R^5$, and $M^2$ represents a magnesium halide group when Z is an alkenyl group having a carbon number of 2 to 6 to produce a hydro silane derivative having the structure of formula (1'):

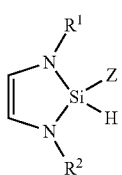
(1')

wherein each of $R^1$ and $R^2$ independently represents an alkyl group having a carbon number of 3 to 12, Z represents an isocyanato group, an isothiocyanato group, an unsubstituted amino group, a monosubstituted amino group represented by $NHR^3$, a disubstituted amino group represented by $NR^4R^5$, or an alkenyl group having a carbon number of 2 to 6, $R^3$ represents an alkyl group having a carbon number of 1 to 12, which may be substituted with a fluorine atom, and each of $R^4$ and $R^5$ independently represents an alkyl group having a carbon number of 1 to 4.

5. The production method as claimed in claim 4, wherein Z is an isocyanato group, an unsubstituted amino group, a monosubstituted amino group represented by $NHR^3$, or an alkenyl group having a carbon number of 2 to 4, each of $R^1$ and $R^2$ is independently an alkyl group having a carbon number of 3 to 8, and $R^3$ is an alkyl group having a carbon number of 1 to 8, which may be substituted with a fluorine atom.

6. The production method as claimed in claim 4, wherein Z is an unsubstituted amino group or a monosubstituted amino group represented by $NHR^3$, $M^2$ is a hydrogen atom, each or $R^1$ and $R^2$ is independently a tert-butyl group or a tert-pentyl group, and $R^3$ is an alkyl group having a carbon number of 1 to 4.

7. A method for producing a hydro silane derivative, comprising reacting a vinylenediaminide alkali salt having the structure of formula (2):

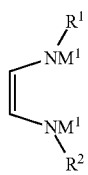
(2)

wherein each of $R^1$ and $R^2$ independently represents an alkyl group having a carbon number of 3 to 12, and $M^1$ represents a lithium atom or a sodium atom with trichlorosilane to produce a chlorosilane derivative having the structure of formula (3):

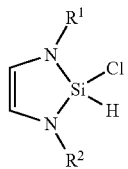
(3)

wherein each of $R^1$ and $R^2$ independently represents an alkyl group having a carbon number of 3 to 12, and further reacting the chlorosilane derivative (3) with a compound having the structure of formula (4):

$M^2Z$ (4)

wherein Z represents an isocyanato group, an isothiocyanato group, an unsubstituted amino group, a monosubstituted amino group represented by $NHR^3$, a disubstituted amino group represented by $NR^4R^5$, or an alkenyl group having a carbon number of 2 to 6, $R^3$ represents an alkyl group having a carbon number of 1 to 12, which may be substituted with a fluorine atom, each of $R^4$ and $R^5$ independently represents an alkyl group having a carbon number of 1 to 4, $M^2$ represents a sodium atom or a potassium atom when Z is an isocyanato group or an isothiocyanato group, $M^2$ represents a hydrogen atom or a lithium atom when Z is an unsubstituted amino group, a monosubstituted amino group represented by $NHR^3$ or a disubstituted amino group represented by $NR^4R^5$, and $M^2$ represents a magnesium halide group when Z is an alkenyl group having a carbon number of 2 to 6 to produce a hydro silane derivative having the structure of formula (1'):

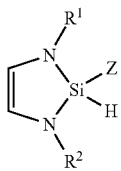

(1')

wherein each of $R^1$ and $R^2$ independently represents an alkyl group having a carbon number of 3 to 12, Z represents an isocyanato group, an isothiocyanato group, an amino group, a monosubstituted amino group represented by $NHR^3$, a disubstituted amino group represented by $NR^4R^5$, or an alkenyl group having a carbon number of 2 to 6, $R^3$ represents an alkyl group having a carbon number of 1 to 12, which may be substituted with a fluorine atom, and each of $R^4$ and $R^5$ independently represents an alkyl group having a carbon number of 1 to 4.

8. A method for producing a silicon-containing thin film, comprising using, as the material, a hydrosilane derivative having the structure of formula (1'):

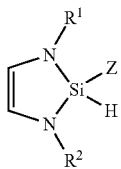

(1')

wherein each of $R^1$ and $R^2$ independently represents an alkyl group having a carbon number of 3 to 12, Z represents an isocyanato group, an isothiocyanato group, an unsubstituted amino group, a monosubstituted amino group represented by $NHR^3$, a disubstituted amino group represented by $NR^4R^5$, or an alkenyl group having a carbon number of 2 to 6, $R^3$ represents an alkyl group having a carbon number of 1 to 12, which may be substituted with a fluorine atom, and each of $R^4$ and $R^5$ independently represents an alkyl group having a carbon number of 1 to 4.

9. The production method as claimed in claim 8, wherein Z is an unsubstituted amino group or a monosubstituted amino group represented by $NHR^3$ and $R^3$ is an alkyl group having a carbon number of 1 to 4.

10. The hydro silane derivative as claimed in claim 2, wherein each of $R^1$ and $R^2$ is independently a tert-butyl group or a tert-pentyl group, Za is an unsubstituted amino group or a monosubstituted amino group represented by $NHR^3$, and R is an alkyl group having a carbon number of 1 to 4.

11. The production method as claimed in claim 5, wherein Z is an unsubstituted amino group or a monosubstituted amino group represented by $NHR^3$, $M^2$ is a hydrogen atom, each or $R^1$ and $R^2$ is independently a tert-butyl group or a tert-pentyl group, and $R^3$ is an alkyl group having a carbon number of 1 to 4.

* * * * *

UNITED STATES PATENT AND TRADEMARK OFFICE
CERTIFICATE OF CORRECTION

PATENT NO.         : 9,120,825 B2
APPLICATION NO.    : 13/702723
DATED              : September 1, 2015
INVENTOR(S)        : Tada et al.

It is certified that error appears in the above-identified patent and that said Letters Patent is hereby corrected as shown below:

In the Claims

Column 55, line 44 (claim 4, line 24) please change "a hydro silane" to -- a hydrosilane --

Column 56, line 10 (claim 6, line 3) please change "each or" to -- each of --

Column 56, line 14 (claim 7, line 1) please change "a hydro silane" to -- a hydrosilane --

Column 56, line 66 (claim 7, line 30) please change "a hydro silane" to -- a hydrosilane --

Column 57, lines 13, 14 (claim 7, lines 34, 35) please change "an amino group" to -- an unsubstituted amino group --

Column 58, line 21 (claim 10, line 4) please change "and R" to -- and R3 --

Column 58, line 26 (claim 11, line 4) please change "each or" to -- each of --

Signed and Sealed this
Fifteenth Day of March, 2016

Michelle K. Lee
*Director of the United States Patent and Trademark Office*